US007830521B2

(12) United States Patent
Yamamoto et al.

(10) Patent No.: US 7,830,521 B2
(45) Date of Patent: Nov. 9, 2010

(54) DETECTION APPARATUS, DETECTION METHOD, AND OPTICALLY TRANSPARENT MEMBER

(75) Inventors: Hiroaki Yamamoto, Kanagawa (JP); Toshihito Kimura, Kanagawa (JP); Hitoshi Shimizu, Kanagawa (JP); Masashi Hakamata, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 430 days.

(21) Appl. No.: 11/864,711

(22) Filed: Sep. 28, 2007

(65) Prior Publication Data

US 2008/0079951 A1    Apr. 3, 2008

(30) Foreign Application Priority Data

Sep. 29, 2006  (JP)  ............................. 2006-269112
Jul. 20, 2007   (JP)  ............................. 2007-189521

(51) Int. Cl.
*G01N 21/00* (2006.01)

(52) U.S. Cl. ...................................................... 356/445
(58) Field of Classification Search .......... 356/445–448
See application file for complete search history.

(56) References Cited

U.S. PATENT DOCUMENTS

| 4,844,613    | A  | 7/1989 | Batchelder et al. |
| 2002/0033943 | A1 | 3/2002 | Clauberg et al.   |
| 2004/0090630 | A1 | 5/2004 | Tittel et al.     |
| 2004/0194039 | A1 | 9/2004 | Lutz et al.       |
| 2005/0110989 | A1 | 5/2005 | Schermer et al.   |
| 2006/0066860 | A1* | 3/2006 | Sato ........................... 356/445 |
| 2006/0159591 | A1 | 7/2006 | Ohtsuka |
| 2007/0054415 | A1* | 3/2007 | Muraishi .................... 436/518 |

FOREIGN PATENT DOCUMENTS

| GB | 2 197 065 A    | 5/1988 |
| JP | 2003-014623    | 1/2003 |
| JP | 2006-098369    | 4/2006 |
| WO | 02/25251 A2    | 3/2002 |
| WO | WO 02/39095 A1 | 5/2002 |

OTHER PUBLICATIONS

Nenninger et al., "Data analysis for optical sensors based on spectroscopy of surface plasmons," Measurement Science and Technology, vol. 13, No. 12, Dec. 1, 2002, pp. 2038-2046.

* cited by examiner

*Primary Examiner*—Michael P Stafira
(74) *Attorney, Agent, or Firm*—Sughrue Mion, PLLC

(57) ABSTRACT

Provided are a detection apparatus, a detection method and an optically transparent member, which can detect a decrease in a precision. A convolution is performed by a convolution portion 80 contained in an image processing portion 38, to acquire the distribution information indicating the light intensity distribution of a light beam, which is totally reflected at the interface and which is incident at a plurality of angles to an dielectric block 52 so as to be totally reflected at the interface of the dielectric block 52. A spatial frequency resolution is performed on the light intensity distribution indicated by the distribution information acquired, by a detection precision evaluating portion 86 contained in the image processing portion 38, to thereby derive the light intensity distribution of each spatial frequency of the light beam. The precision is detected by comparing the light intensity distribution derived, with a threshold value predetermined for each spatial frequency.

40 Claims, 45 Drawing Sheets

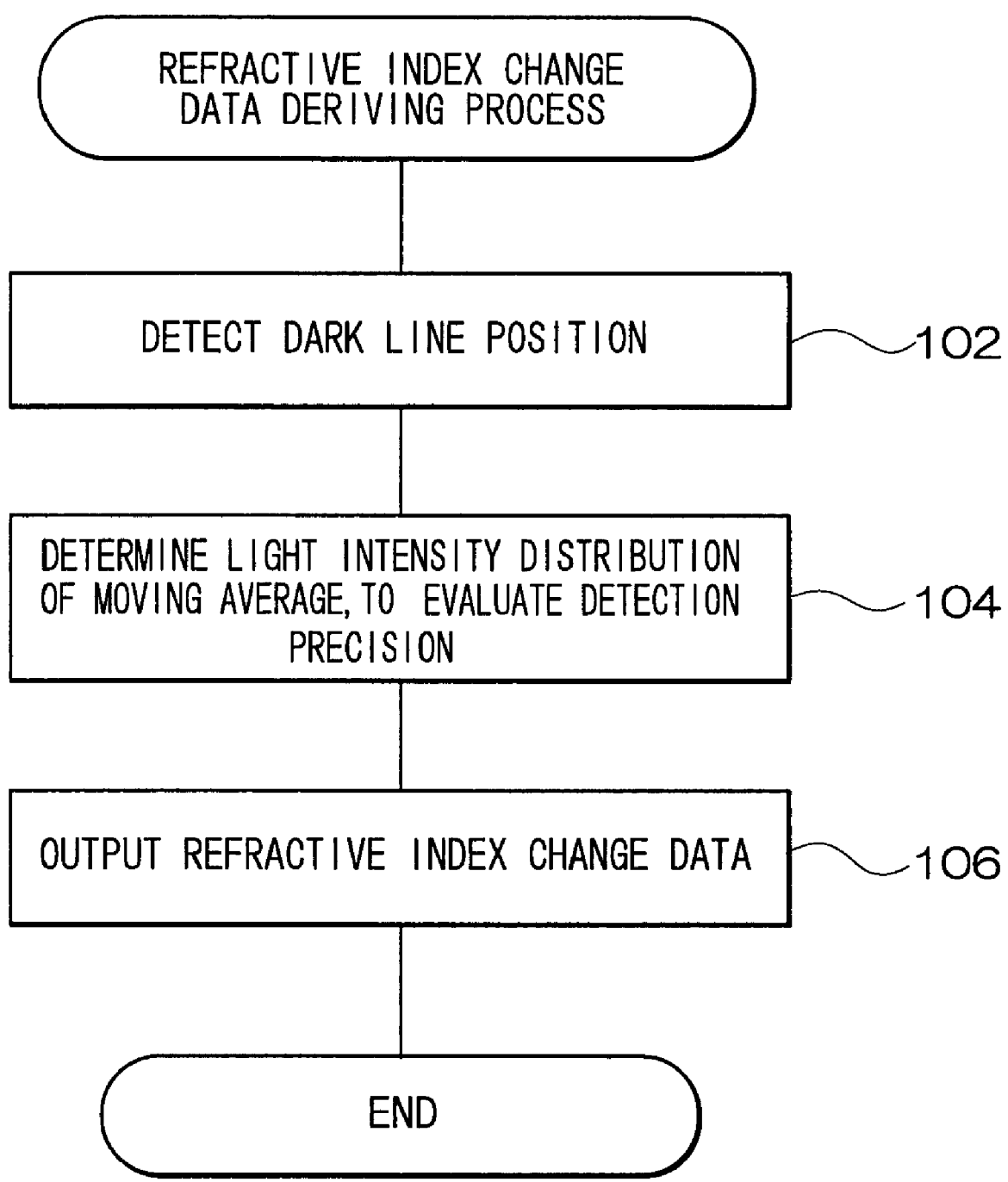

FIG. 14A  (1) LIGHT INTENSITY DISTRIBUTION INDICATED BY INTENSITY DISTRIBUTION INFORMATION

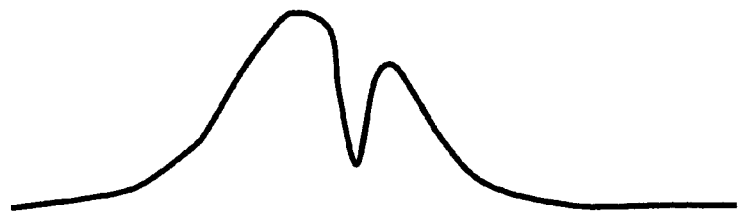

FIG. 14B  (2) SMOOTHED LIGHT INTENSITY DISTRIBUTION OF (1)

FIG. 14C  (3) DIFFERENTIAL INTENSITY DISTRIBUTION = (1) - (2)

FIG. 14D  (4) DIFFERENTIAL INTENSITY DISTRIBUTION + THRESHOLD VALUE (ADD THRESHOLD VALUE AS A WHOLE)

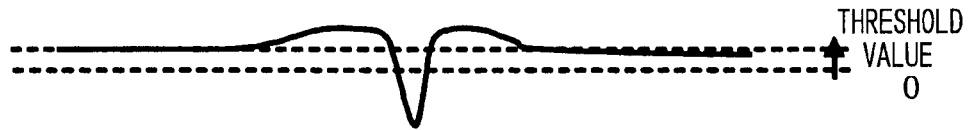

FIG. 14E  (5) SPECIFY PORTION OF THE 0 OR LESS INTENSITY OF (4)

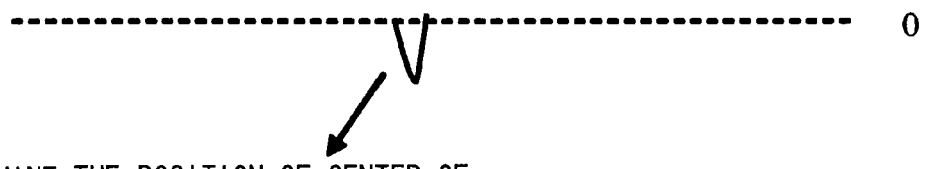

DETERMINE THE POSITION OF CENTER OF GRAVITY BY CENTROID METHOD

FIG. 24A  WIDTH DEPENDENCY (AMPLITUDE: 1000 digits, NOISE POSITION: 520 pixels)
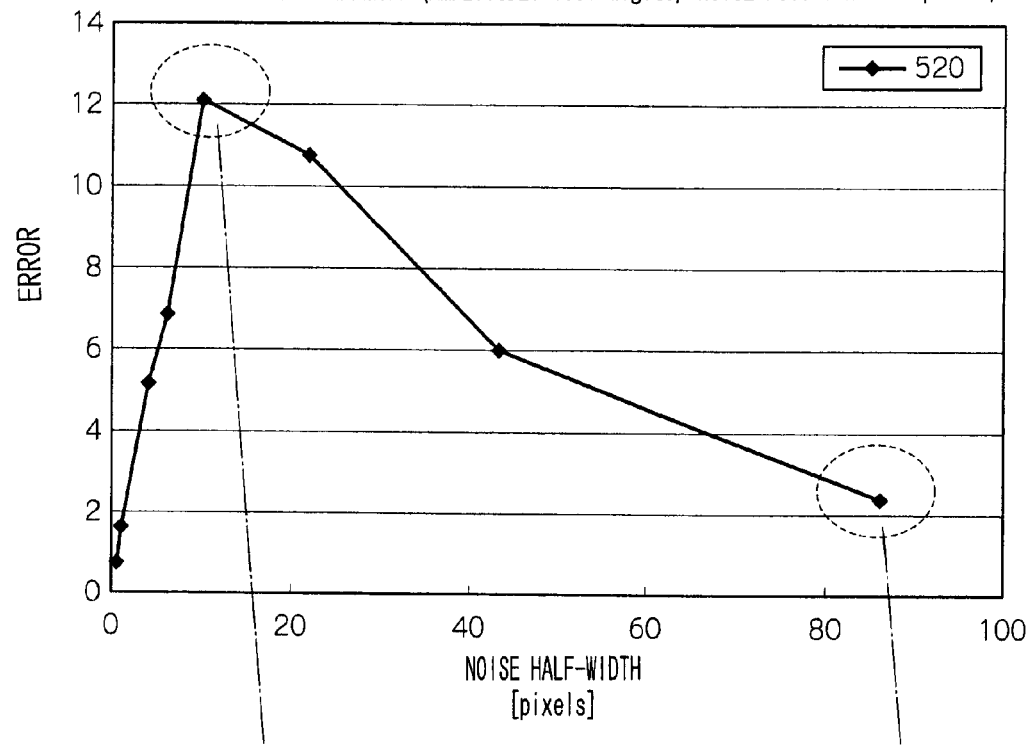
FIG. 24B
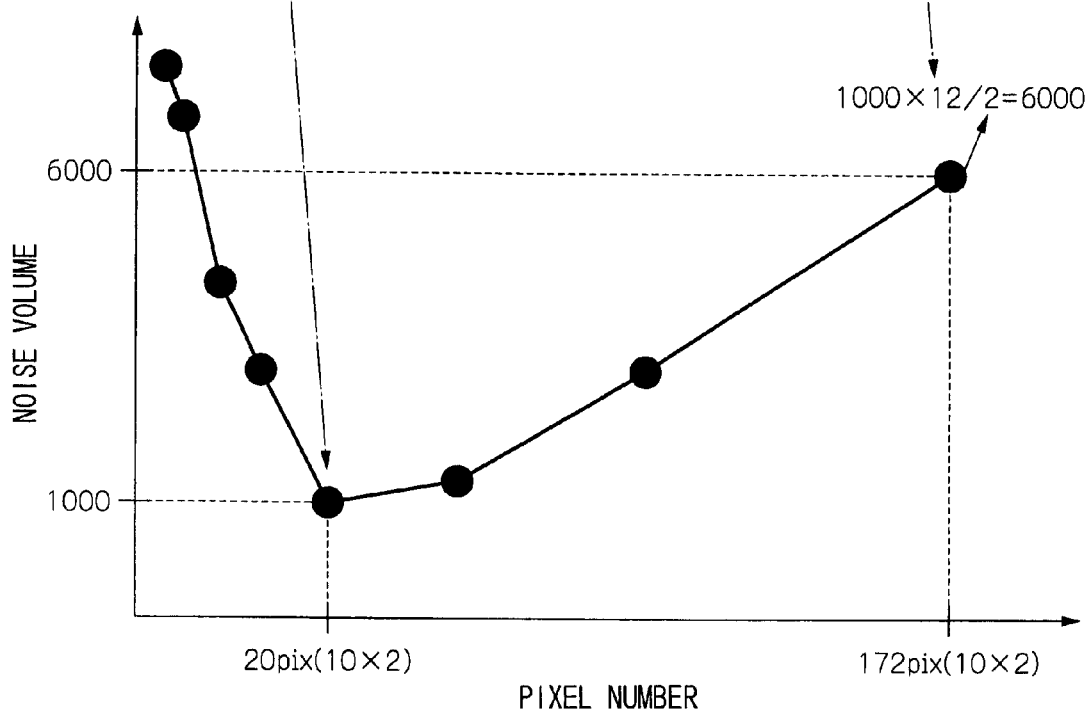

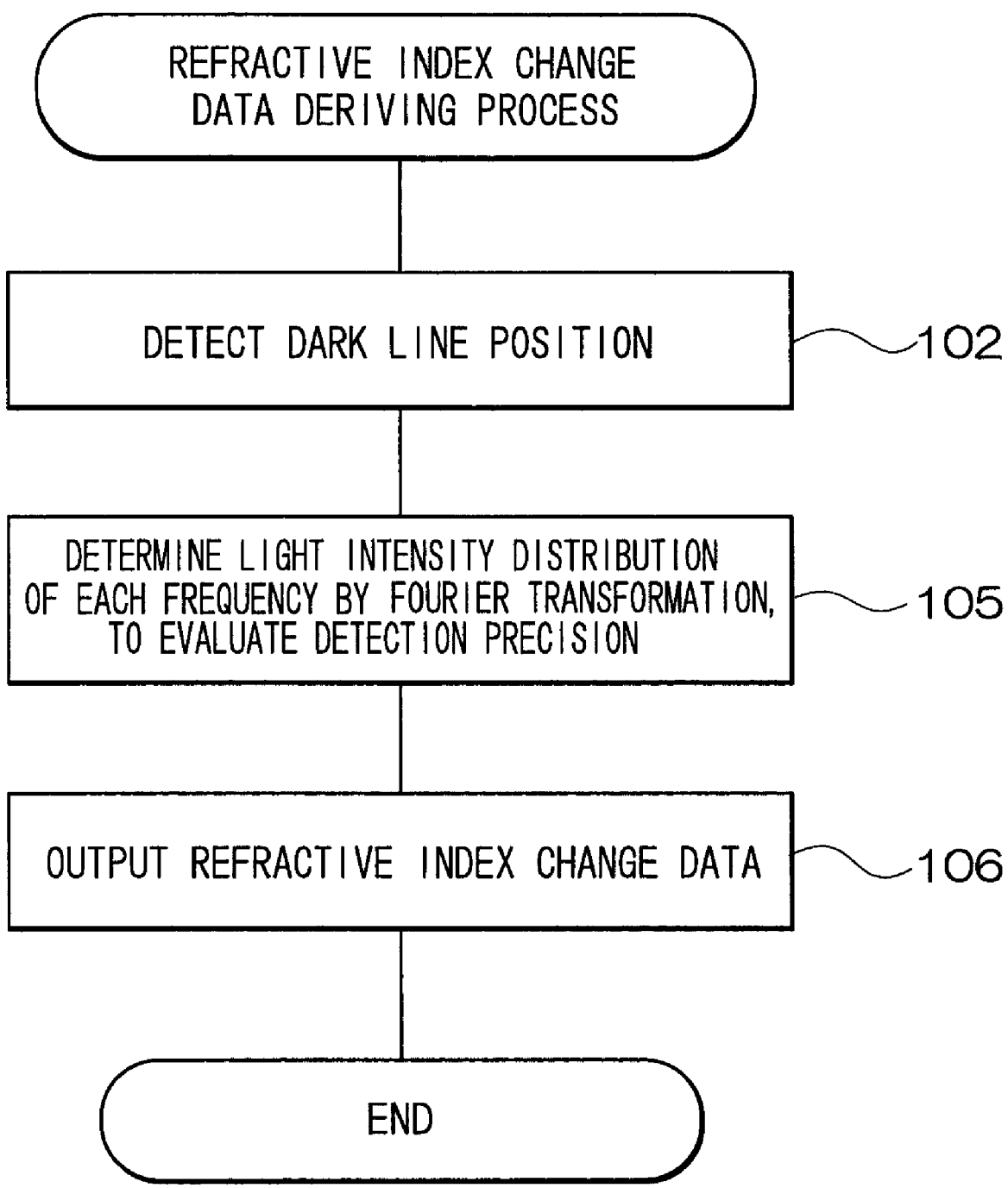

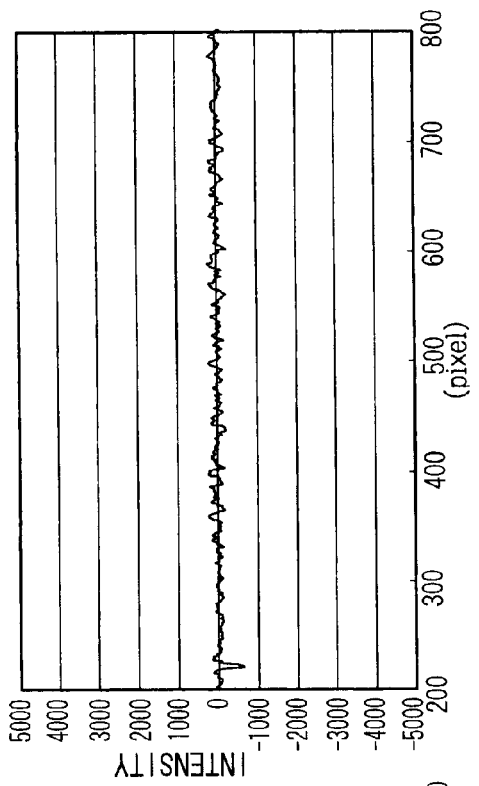
FIG. 39A  AVERAGED BY 5 pixels
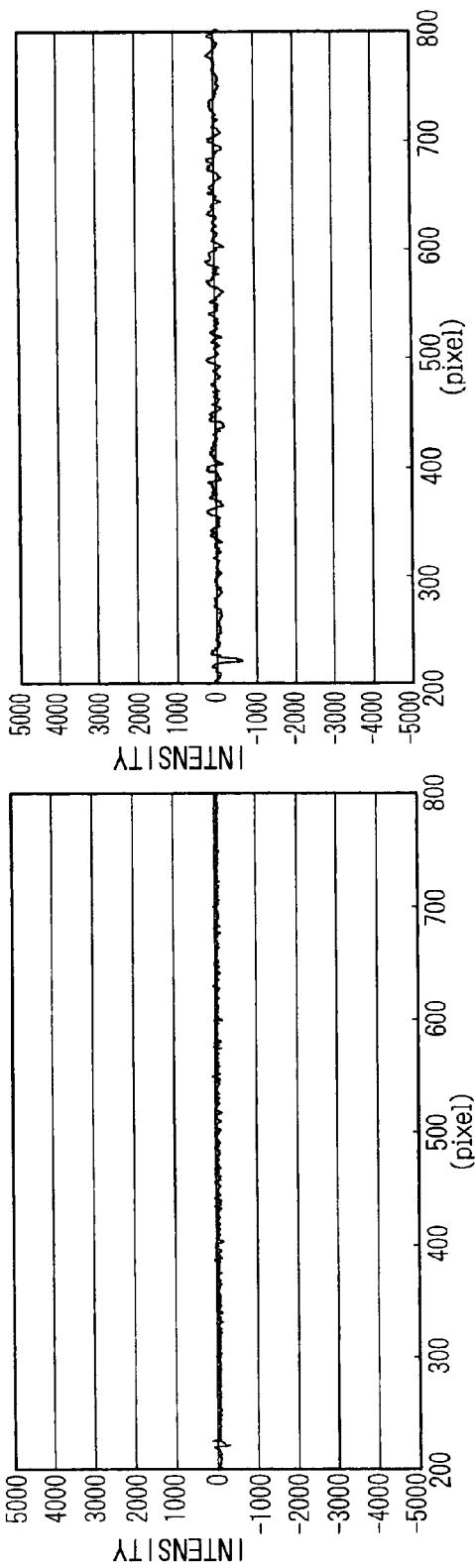
FIG. 39B  AVERAGED BY 21 pixels
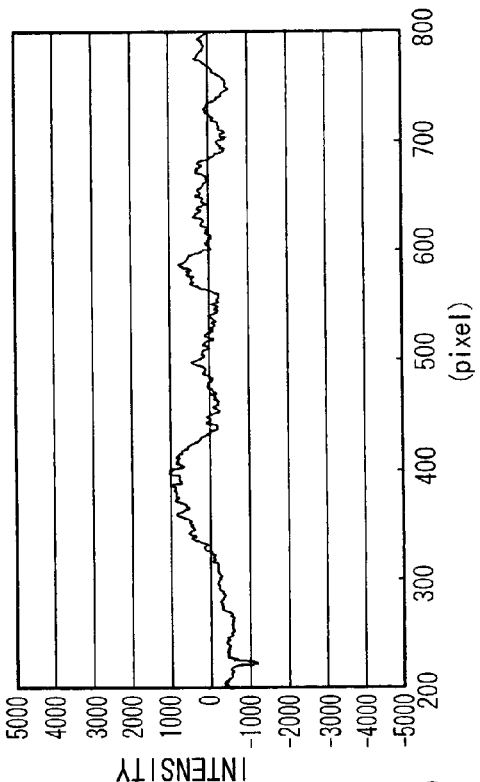
FIG. 39C  AVERAGED BY 45 pixels
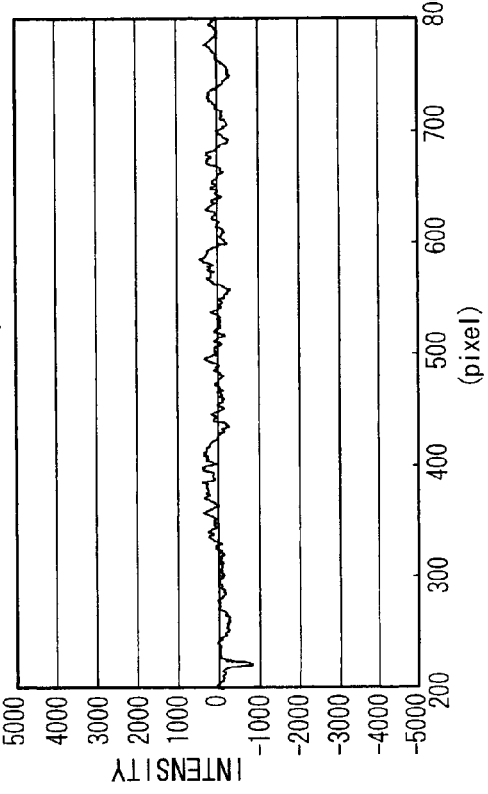
FIG. 39D  AVERAGED BY 87 pixels

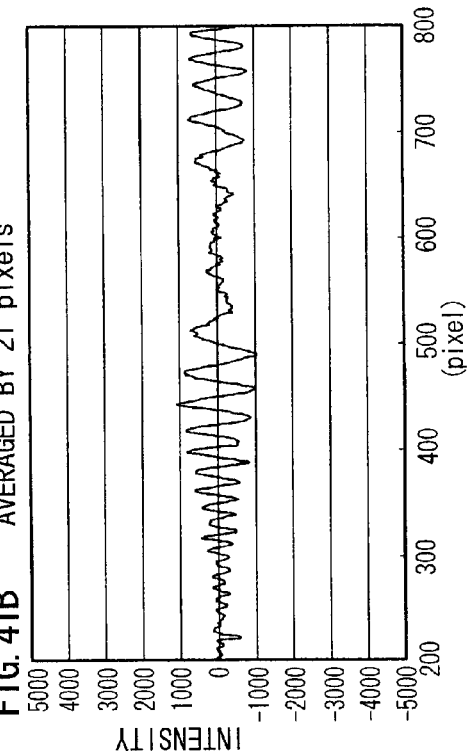
FIG. 41A AVERAGED BY 5 pixels
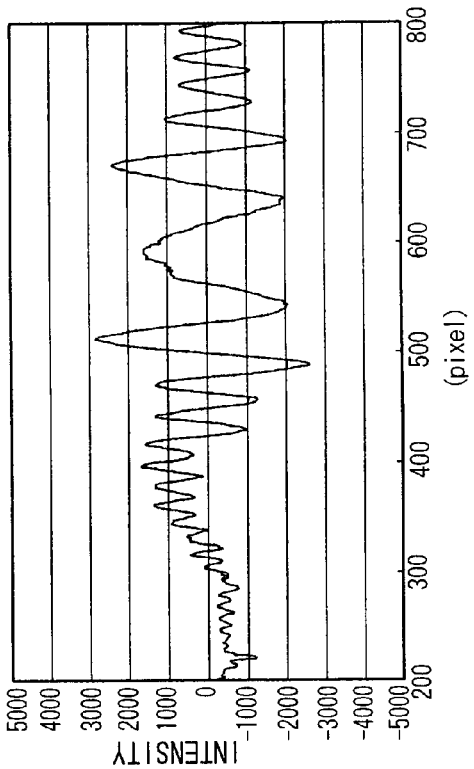
FIG. 41B AVERAGED BY 21 pixels
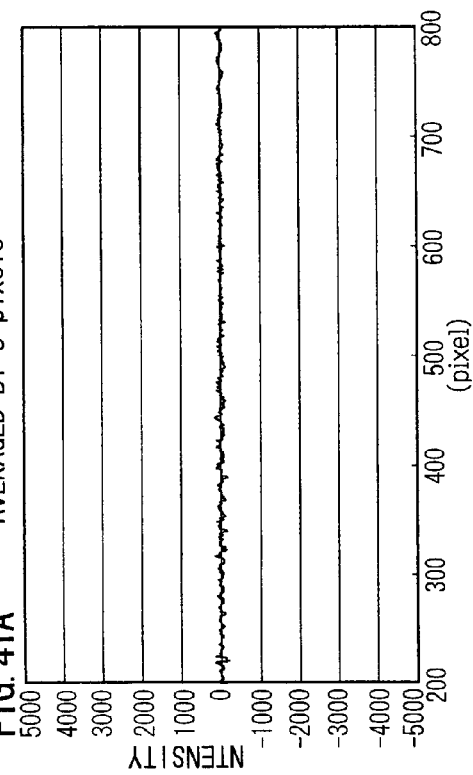
FIG. 41C AVERAGED BY 45 pixels
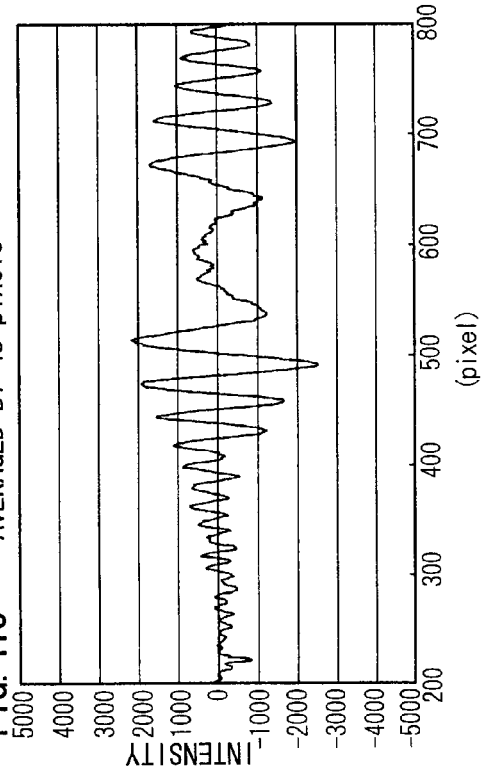
FIG. 41D AVERAGED BY 87 pixels

DETECTION APPARATUS, DETECTION METHOD, AND OPTICALLY TRANSPARENT MEMBER

CROSS-REFERENCE TO RELATED APPLICATION

This application claims priority under 35 USC 119 from Japanese Patent Application No. 2006-269112 and No. 2007-189521, the disclosures of which are incorporated by reference herein.

BACKGROUND OF THE INVENTION

1. Field of the Invention

The present invention relates to a detection apparatus and, more particularly, to a detection apparatus for detecting the characteristics of a sample by making use of a surface plasmon resonance.

2. Description of the Related Art

Conventionally, a surface plasmon sensor is known as a detection apparatus for detecting the characteristics of a sample by making use of the surface plasmon resonance (SPR). Generally, the surface plasmon sensor is constituted by: a prism; a metallic thin film layer arranged on a surface of the prism for fixing a physiologically active substance as the sample; a light source for emitting a light beam; an optical system for making the light beam incident at various angles to the prism so that total reflection conditions may be satisfied on the interface between the prism and the thin film layer; and a photodetector for detecting the light intensity distribution of the light beam totally reflected at the interface. The characteristics of the physiologically active substance are analyzed by detecting the position, at which the dark line is formed by the total reflection attenuation due to the surface plasmon resonance, from the light intensity distribution detected by the photodetector.

As a technique for detecting the position of the dark line, in Japanese Patent Application Laid-Open (JP-A) No. 2006-98369, a technique is disclosed for detecting the position of the dark line highly precisely by storing in advance the light intensity distribution of a light beam having no total reflection attenuation itself, as a reference light intensity distribution, detecting the light intensity distribution of the light beam totally reflected at the interface, and dividing the detected light intensity distribution for each distribution value by the reference light intensity distribution, so that the influence of the dispersion of the light intensity distribution of the light beam is offset.

In JP-A No. 2003-14623, a technique is disclosed for detecting the position of a total reflection attenuation angle highly precisely by storing in advance an equation of a plasmon resonance curve expressing the relation between a reflectance and an incidence angle, and by fitting the plasmon resonance curve, as expressed by the equation, for the light intensity distribution of the light beam detected.

Here in a detection apparatus of this type, noise is generated in the light beam due to dust stuck to the prism or by flaws in the optical paths of the optical system. This results in a decrease in the precision of detection of the dark line position.

However, in the techniques thus far described, the situation in which noise occurs in the light beam has not been taken into consideration and there is the problem that it is impossible to detect the decrease in the precision of detection of the dark line position.

SUMMARY OF THE INVENTION

The present invention has been made in view of the above circumstances, and provides a detection apparatus, a detection method and an optically transparent member.

A first aspect of the present invention provides a detection apparatus comprising: an acquisition unit that acquires distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member; a derivation unit that performs a spatial frequency resolution on the light intensity distribution indicated by the distribution information acquired by the acquisition unit, to thereby derive the light intensity distribution of each spatial frequency of the light beam; and a detection unit that compares the light intensity distribution derived by the derivation unit, with a threshold value predetermined for each spatial frequency, to thereby detect a detection precision of a dark line position.

A second aspect of the present invention provides a detection method comprising: acquiring distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member; performing a spatial frequency resolution on the light intensity distribution indicated by the distribution information acquired, to thereby derive the light intensity distribution of each spatial frequency of the light beam; and comparing the light intensity distribution derived, with a threshold value predetermined for each spatial frequency, to thereby detect a detection precision of a dark line position.

A third aspect of the present invention provides an optically transparent member having transparency to a light beam, wherein: distribution information indicating a light intensity distribution of the light beam which is totally reflected at an interface, and which is incident at a plurality of angles so as to be totally reflected at the interface, is acquired; a spatial frequency resolution is performed on the light intensity distribution indicated by the distribution information so that the light intensity distribution of each spatial frequency of the light beam is derived; and the light intensity distribution is compared with a threshold value predetermined for each spatial frequency so that a detection precision of a dark line position is detected.

BRIEF DESCRIPTION OF THE DRAWINGS

Embodiments of the present invention will be described in detail based on the following figures, wherein:

FIG. 13 is a flow chart showing a flow of a refractive index change data deriving process according to the first embodiment;

FIG. 14A is a view showing a flow at the time when a dark line is derived;

FIG. 14B is a view showing a flow at the time when the dark line is derived;

FIG. 14C is a view showing a flow at the time when the dark line is derived;

FIG. 14D is a view showing a flow at the time when the dark line is derived;

FIG. 14E is a view showing a flow at the time when the dark line is derived;

FIG. 24A is a graph presenting a relation between the half-width of noises and the error;

FIG. 24B is a graph presenting the threshold values of every pixel numbers at the time of averaging;

FIG. 25 is a flow chart showing a flow of a refractive index change data deriving process according to the second embodiment;

FIG. 39A is a graph presenting a differential intensity distribution of the light intensity distribution presented in FIG. 38;

FIG. 39B is a graph presenting a differential intensity distribution of the light intensity distribution presented in FIG. 38;

FIG. 39C is a graph presenting a differential intensity distribution of the light intensity distribution presented in FIG. 38;

FIG. 39D is a graph presenting a differential intensity distribution of the light intensity distribution presented in FIG. 38;

FIG. 41A is a graph presenting a differential intensity distribution of the light intensity distribution presented in FIG. 40;

FIG. 41B is a graph presenting a differential intensity distribution of the light intensity distribution presented in FIG. 40;

FIG. 41C is a graph presenting a differential intensity distribution of the light intensity distribution presented in FIG. 40;

FIG. 41D is a graph presenting a differential intensity distribution of the light intensity distribution presented in FIG. 40;

DETAILED DESCRIPTION OF THE INVENTION

Figure 1:
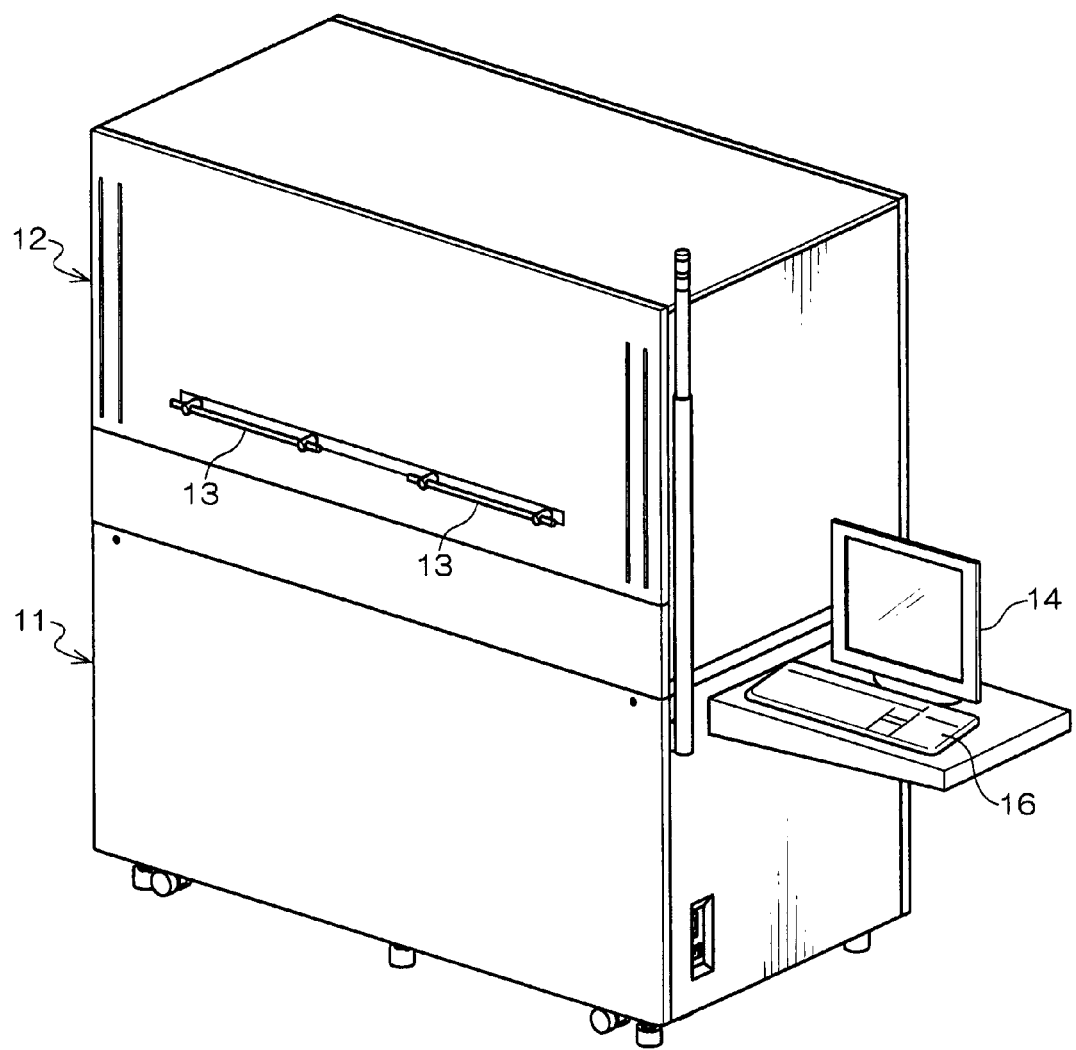
FIG. 1 is a perspective view of an entire biosensor according to the first and second embodiments of the present invention.

Herebelow, an example of an exemplary embodiment of the present invention will be described in detail with reference to the drawings.

First Embodiment

A biosensor 10 serving as a detection apparatus according to the first embodiment is a so-called surface plasmon sensor which measures an interaction between protein Ta and a sample A by using surface plasmon resonance generated on a surface of a metal film.

As shown in FIGS. 1 to 4, the biosensor 10 includes a lower housing 11 and an upper housing 12. The upper housing 12 consists of a heat insulating material and covers an entire upper half of the biosensor 10. The interior of the upper housing 12 is heat-insulated from the outside and the interior of the lower housing 11. A front side of the upper housing 12 can be open upward. A grip 13 is attached to the front side. A display 14 and an input portion 16 are installed outside the upper housing 12.

Figure 2:
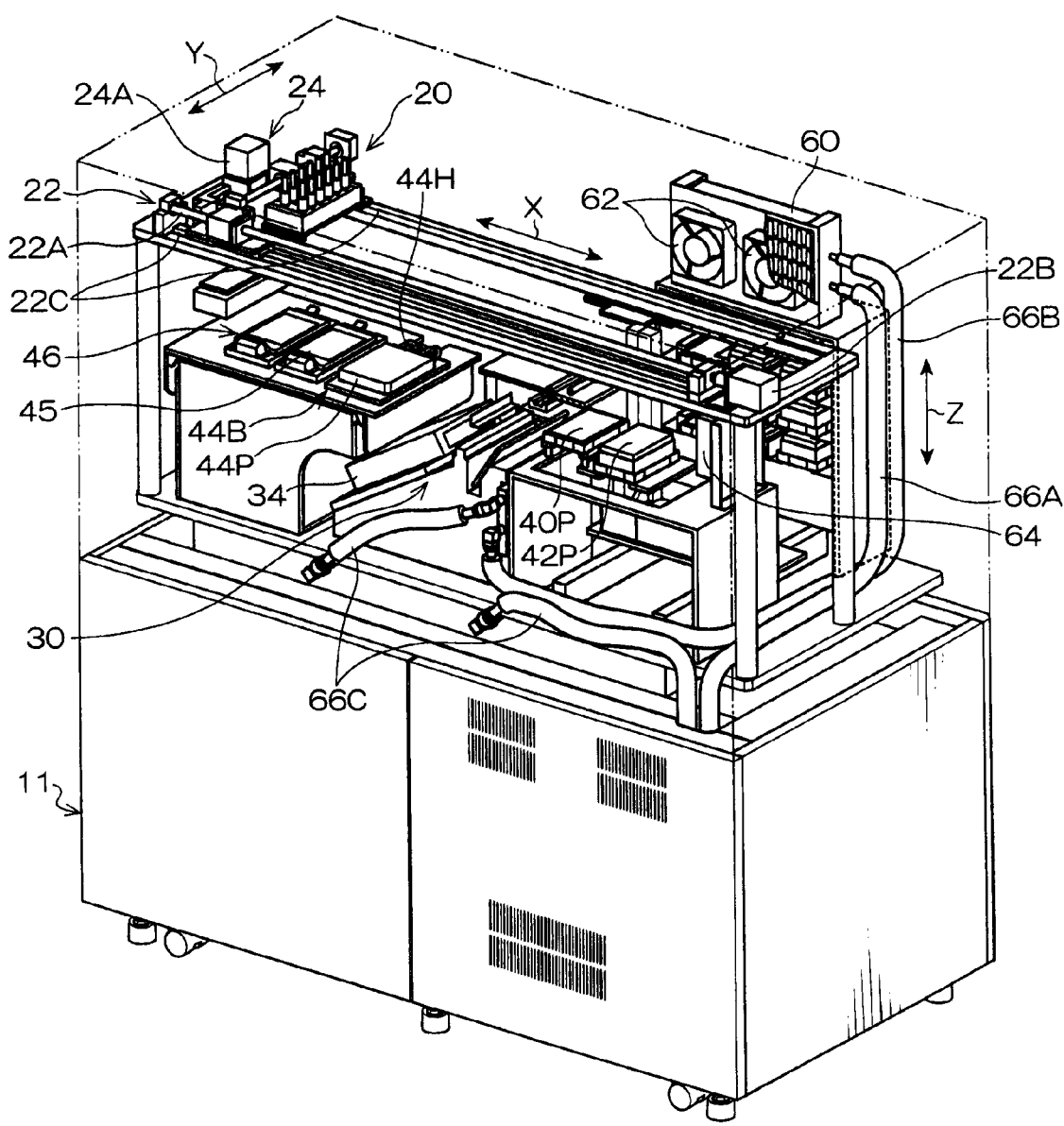
FIG. 2 is a perspective view of an interior of the biosensor according to the first and second embodiments of the present invention.
Figure 3:
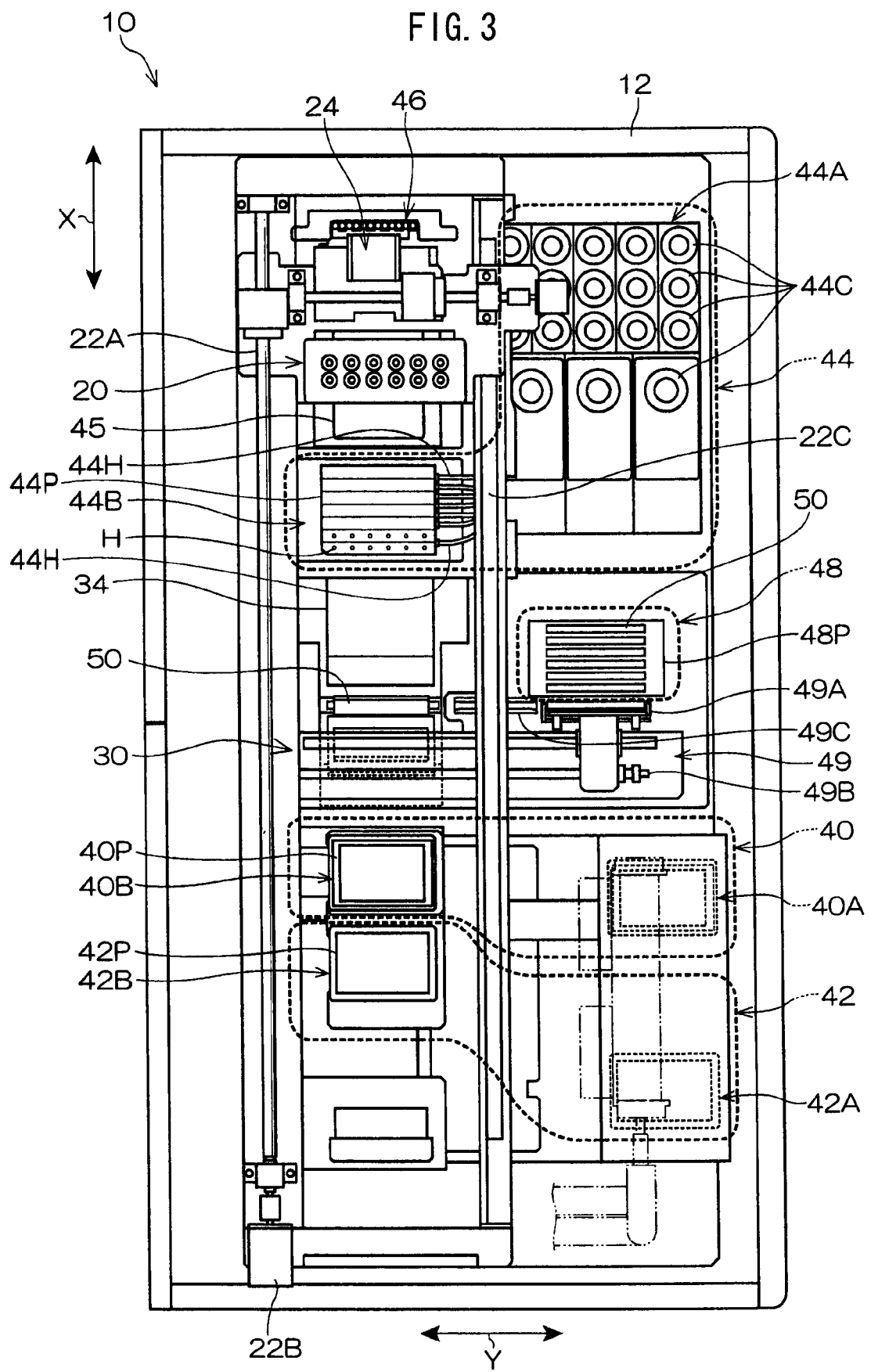
FIG. 3 is a top view of the interior of the biosensor according to the first and second embodiments of the present invention.
Figure 4:
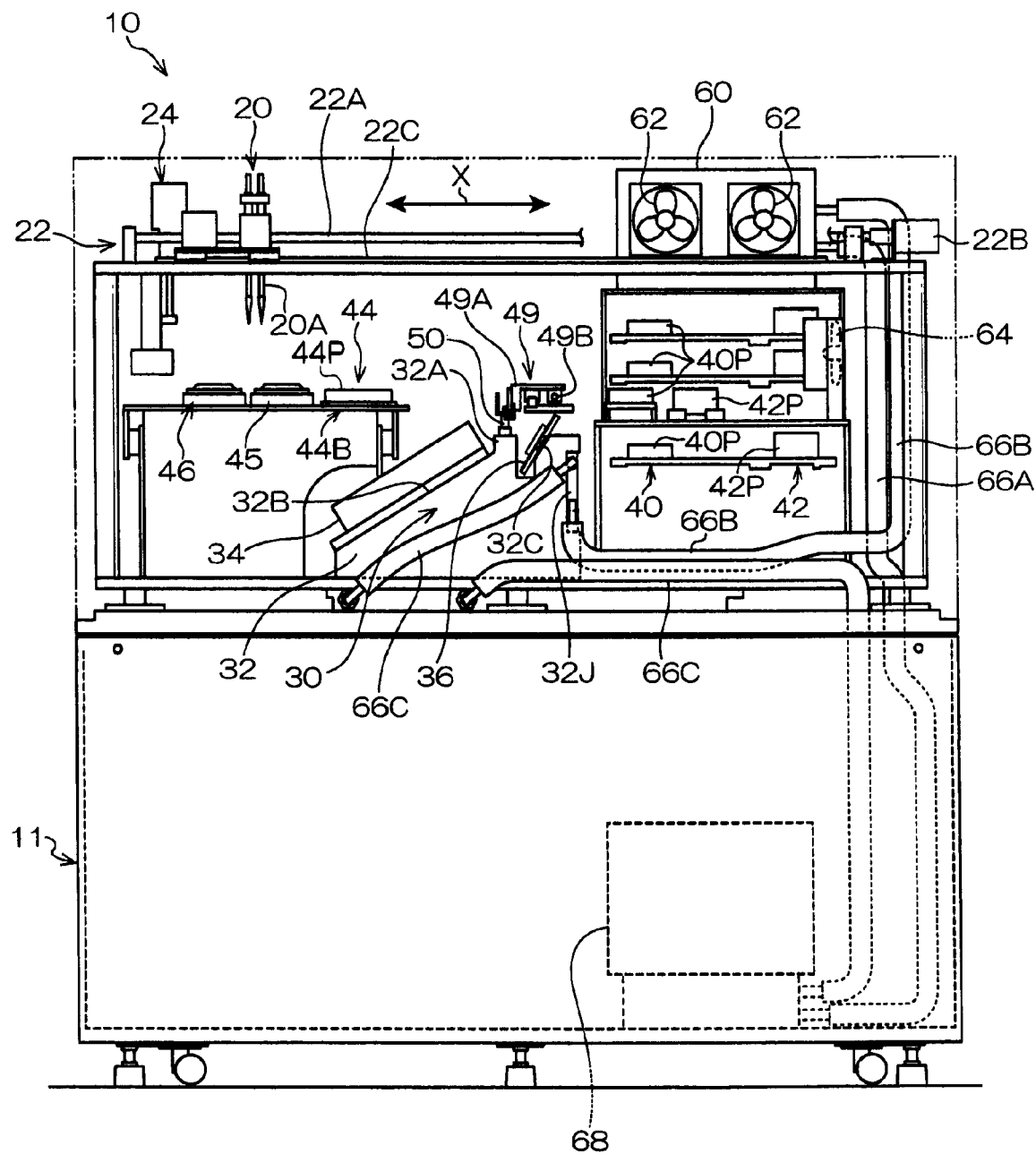
FIG. 4 is a side view of the interior of the biosensor according to the first and second embodiments of the present invention.

FIG. 2 is a view showing the interior of the biosensor 10 from which the upper housing 12 is removed when viewed from a side opposing the view side of FIG. 1. FIG. 3 is a view of the interior of the housing when viewed from the top surface, and FIG. 4 is a side view of the interior when viewed from the front side in FIG. 2.

In the upper housing 12, a dispensing head 20, a measurement portion 30, a sample stock portion 40, a pipet chip stock portion 42, a buffer stock portion 44, a cold insulation portion 46, a measurement chip stock portion 48, a radiator 60, a radiator blowing fan 62, and a horizontal blowing fan 64.

The sample stock portion 40 is constituted by a sample stacking portion 40A and a sample setting portion 40B. In the sample stacking portion 40A, sample plates 40P on which different analyte solutions serving as sample to be measured are stocked in respective cells are stacked in a Z direction (vertical direction) and accommodated. In the sample setting portion 40B, one sample plate 40P is conveyed by a conveying mechanism (not shown) from the sample stacking portion 40A and set.

The pipet chip stock portion 42 is constituted by a pipet chip stacking portion 42A and a pipet chip setting portion 42B. In the pipet chip stacking portion 42A, pipet chip stockers 42P which hold a plurality of pipet chips are stacked in the Z direction and accommodated. In the pipet chip setting portion 42B, one pipet chip stocker 42P is conveyed by a conveying mechanism (not shown) from the pipet chip stacking portion 42A and set.

The buffer stock portion 44 is constituted by a bottle accommodation portion 44A and a buffer supply portion 44B. In the bottle accommodation portion 44A, a plurality of bottles 44C in which buffer liquid serving as reference sample to be a reference in measurement is reserved is accommodated. In the buffer supply portion 44B, a buffer plate 44P is set. The buffer plate 44P is partitioned into a plurality of stripes. Buffer liquids having different concentrations are reserved in the partitions, respectively. In addition, holes H into which the pipet chips CP are inserted when the dispensing head 20 accesses the buffer plate 44P are formed in the upper part of the buffer plate 44P. The buffer liquid is supplied by hoses 44H from the bottles 44C to the buffer plate 44P.

A correcting plate 45 is arranged next to the buffer supply portion 44B, and a cold insulation portion 46 is arranged next to the correcting plate 45. The correcting plate 45 is a plate to perform concentration adjustment of the buffer liquid and has a plurality of cells arranged in the form of a matrix. In the cold insulation portion 46, samples which need to be cooled is arranged. The temperature of the cold insulation portion 46 is low and the temperature of the sample is kept to be low on the cold insulation portion 46.

A measurement chip accommodation plate 48P is set in the measurement chip stock portion 48. A plurality of measurement chips 50 is accommodated in the measurement chip accommodation plate 48P.

A measurement chip conveying mechanism 49 is arranged between the measurement chip stock portion 48 and the measurement portion 30. The measurement chip conveying mechanism 49 includes a holding arm 49A which sandwiches the measurement chip 50 from both sides to hold the measurement chip 50, a ball screw 49B which moves the holding arm 49A in a Y direction by rotation, and a conveying rail 49C arranged in the Y direction on which the measurement chip 50 is placed. In measurement, one measurement chip 50 is placed from the measurement chip accommodation plate 48P onto the conveying rail 49C by the measurement chip conveying mechanism 49, and moved and set in the measurement portion 30 while being held by the holding arm 49A.

Figure 5:
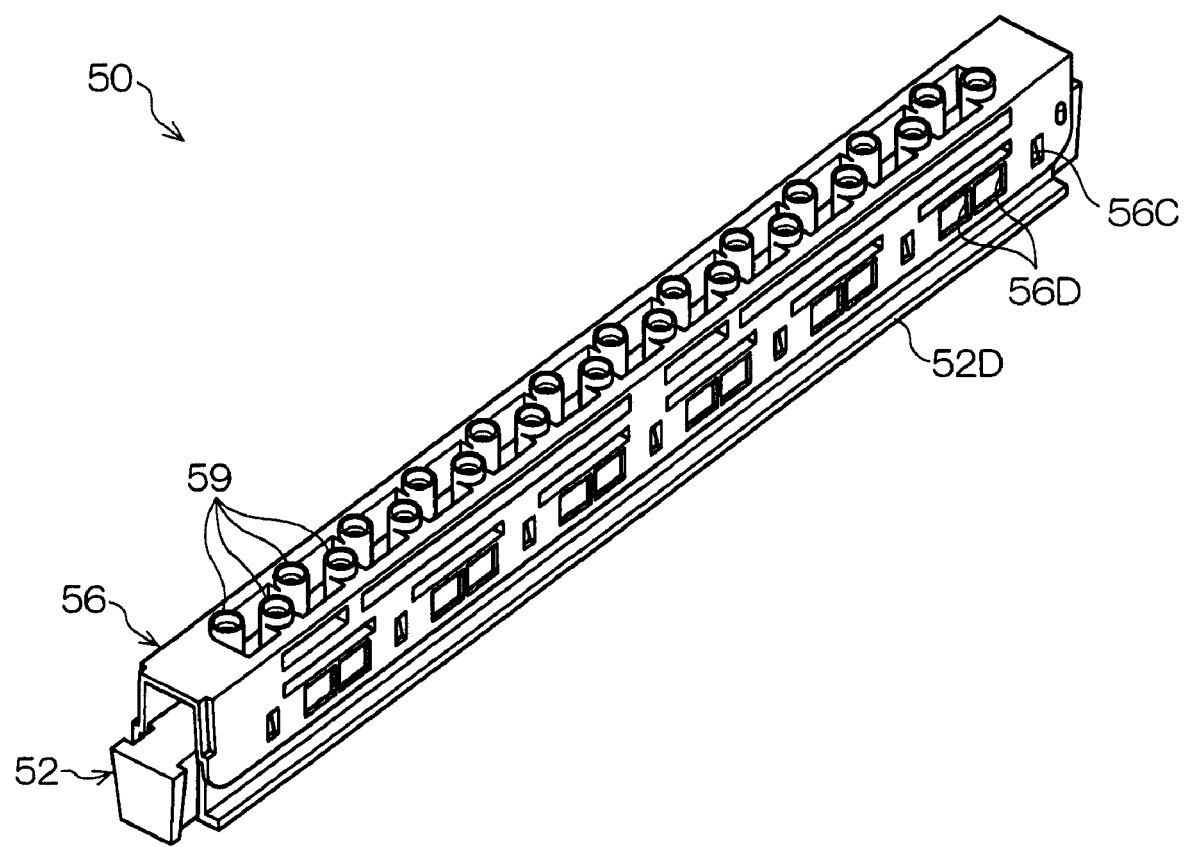
FIG. 5 is a perspective view of a measurement chip according to the first and second embodiments of the present invention.
Figure 6:
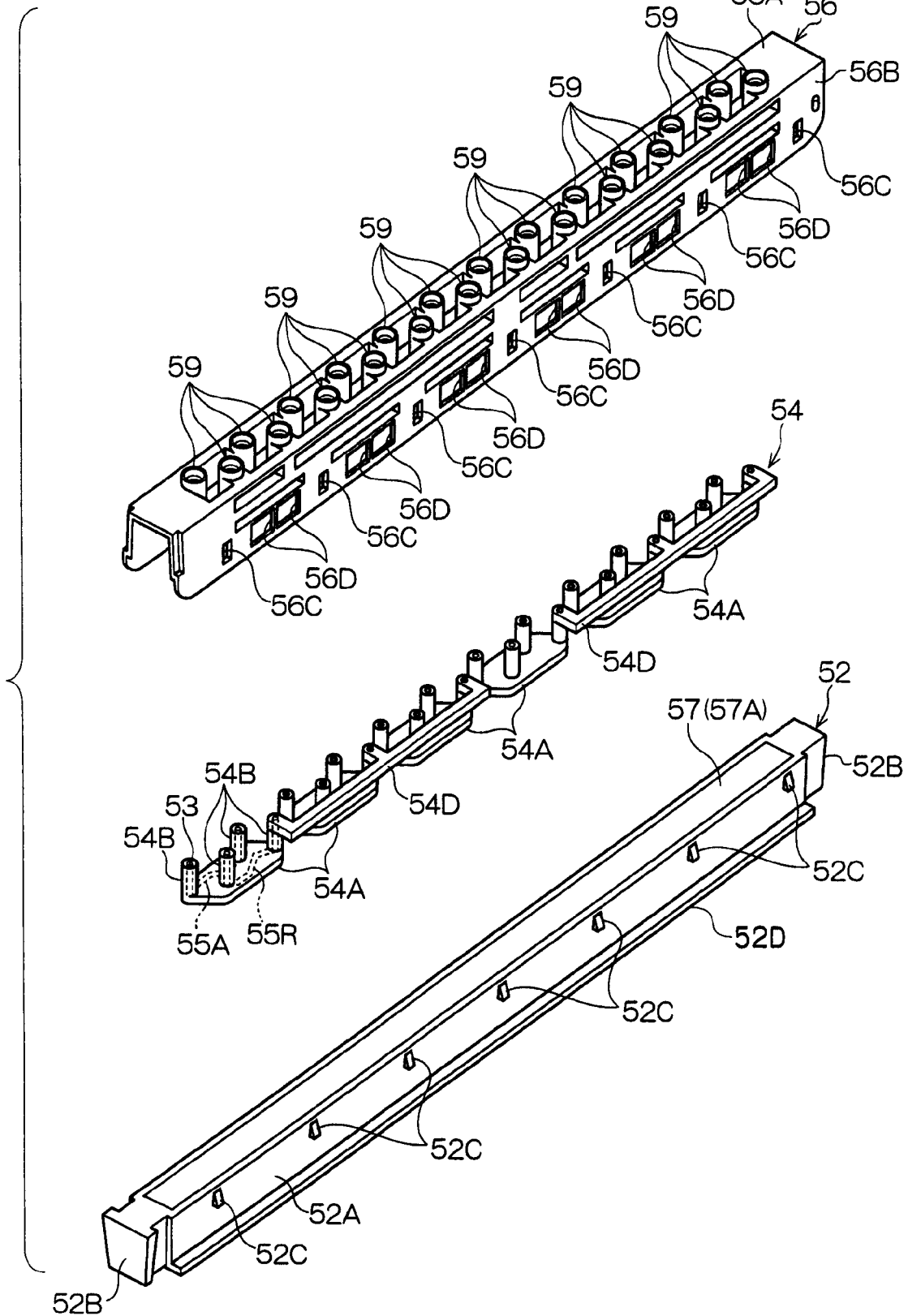
FIG. 6 is an exploded perspective view of the measurement chip according to the first and second embodiments of the present invention.

The measurement chips 50, as shown in FIGS. 5 and 6, is constituted by a dielectric block 52, a flow path member 54, and a holding member 56.

The dielectric block 52 consists of a transparent resin being transparent to a light beam and the like, and has a prism portion 52A of bar-like shape having a trapezoidal section, and held portions 52B which are integrated with the prism portion 52A at both the ends thereof. A thin film 57 is formed on an upper surface of a larger one of two faces which are parallel to each other of the prism portion 52A. The dielectric block 52 functions as a so-called prism. In measurement by the biosensor 10, a light beam is incident from one of two opposing side faces which are not parallel to each other of the prism portion 52A, and a light beam totally reflected at an interface of the thin film 57 is emitted from the other side face.

A linker layer 57A to fix protein Ta on the thin film 57 is formed on the surface of the thin film 57. The protein Ta is fixed on the linker layer 57A.

Engagement convex portions 52C engaged with the holding member 56 are formed on both side faces of the prism portion 52A along an upper side edge. A flange portion 52D engaged with the conveying rail 49C is formed on the lower side of the prism portion 52A along a side edge.

As shown in FIG. 6, the flow path member 54 has six base portions 54A, and four cylindrical members 54B are upright formed on each of the base portions 54A. For every three base portions 54A, the base portions 54A are connected at an upper part of one of the upright formed cylindrical members 54B by the connecting member 54D. The flow path member 54 consists of a soft, elastic, and flexible material, for example, amorphous polyolefin elastomer.

Figure 7:
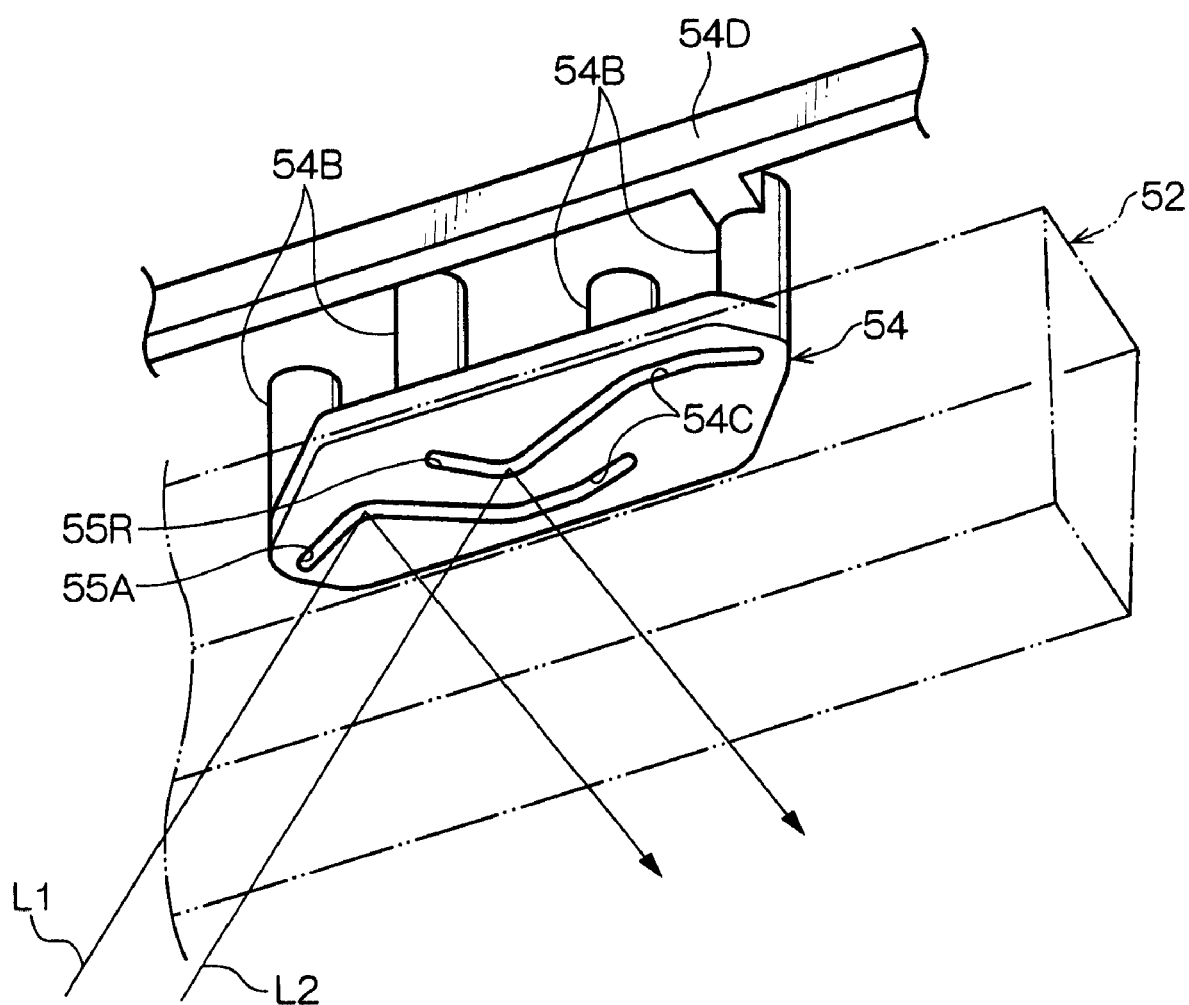
FIG. 7 is a view showing a state in which a light beam is incident to a measurement region and a reference region of the measurement chip according to the first and second embodiments of the present invention.

In the base portion 54A, as shown in FIG. 7, two approximately S-shaped flow path grooves 54C are formed on the bottom side. The flow path groove 54C has end portions each communicating with a hollow portion of one of the cylindrical members 54B. The base portions 54A has a bottom surface which is brought into tight contact with an upper surface of the dielectric block 52, a space constituted between the flow path groove 54C and the upper surface of the dielectric block 52 and the hollow portion constitute a liquid flow path 55. Two liquid flow paths 55 are formed in one of the base portions 54A. In each of the liquid flow paths 55, an inlet/outlet port 53 of the liquid flow path 55 is formed in an upper end face of the cylindrical members 54B.

Figure 8:
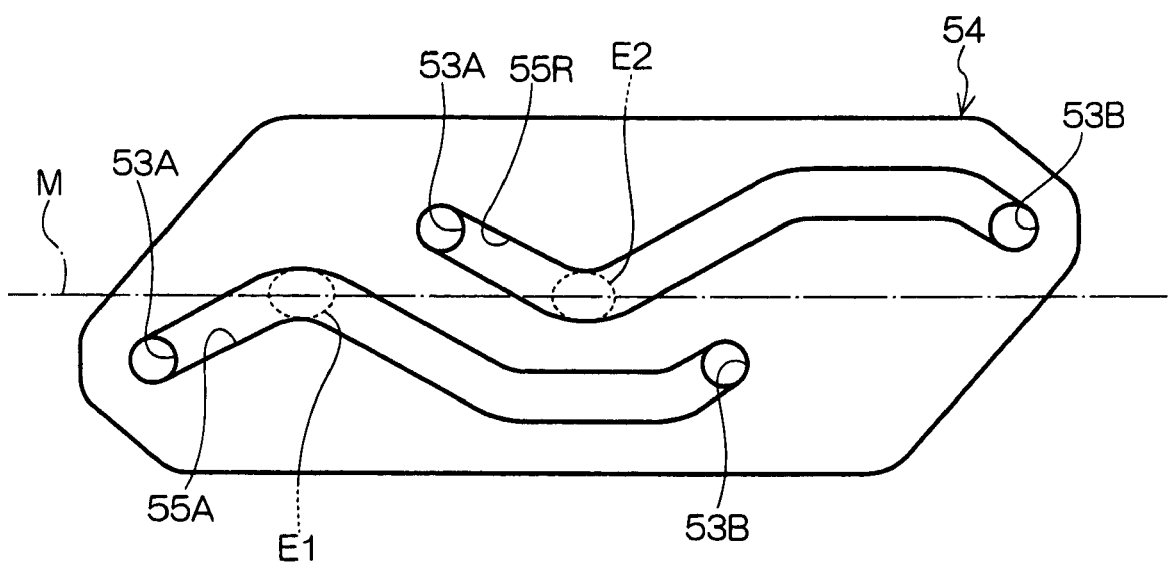
FIG. 8 is a view of a flow path member of the measurement chip according to the first and second embodiments of the present invention when viewed from bottom.

In this case, one of the two liquid flow paths 55 is used as a measurement flow path 55A, and the other is used as a reference flow path 55R. Measurement is performed in the state such that protein Ta is fixed on the thin film 57 (on the linker layer 57A) of the measurement flow path 55A, and no protein Ta is fixed on the thin film 57 (on the linker layer 57A) of the reference flow path 55R. Light beams L1 and L2 are incident to the measurement flow path 55A and the reference flow path 55R respectively, as shown in FIG. 7. The light beams L1 and L2, as shown in FIG. 8, irradiate the S-shaped curved portions arranged on a center line M of the base portion 54A. An irradiation region of the light beam L1 in the measurement flow path 55A is called a measurement region E1, and an irradiation region of the light beam L2 in the reference flow path 55R is called a reference region E2. The reference region E2 is a region in which measurement is performed to correct data obtained from the measurement region E1 on which the protein Ta is fixed.

The holding member 56 (refer to FIG. 6) of the measurement chip 50 has a large length and a shape obtained by forming an upper surface member 56A and two side face plates 56B like a lid. On the side face plate 56B, engagement holes 56C engaged with the engagement convex portions 52C of the dielectric block 52, and windows 56D at positions corresponding to the optical paths of the light beams L1 and L2 are formed. The holding member 56 is attached to the dielectric block 52 such that the engagement holes 56C and the engagement convex portions 52C are engaged with each other. The flow path member 54 is integrated with the holding member 56 and arranged between the holding member 56 and the dielectric block 52.

On the upper surface member 56A, receiving portions 59 are formed at positions corresponding to the cylindrical members 54B of the flow path member 54. Each of the receiving portions 59 is approximately cylindrical.

The dispensing head 20, as shown in FIG. 2, is arranged in an upper part in the upper housing 12, and can be moved in a direction of an arrow X by a horizontal drive mechanism 22. The horizontal drive mechanism 22 is constituted by a ball screw 22A, a motor 22B, and a guide rail 22C. The ball screw 22A and the guide rail 22C are arranged in the X direction. As the guide rail 22C, two guide rails are parallel arranged. One of the guide rails 22C is arranged below the ball screw 22A with a predetermined interval. The dispensing head 20 is moved in the X direction along the guide rail 22C by rotation of the ball screw 22A.

Figure 9:
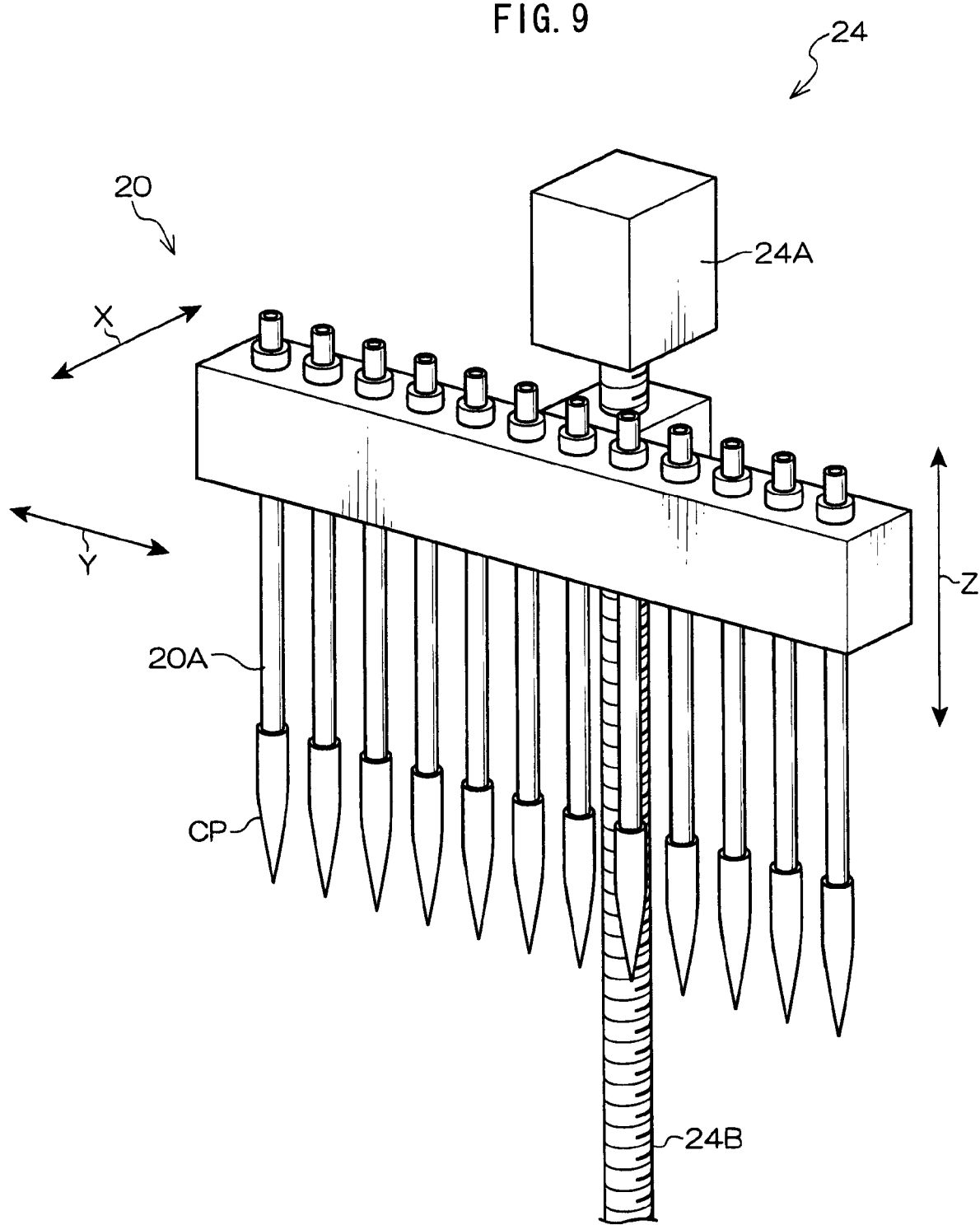
FIG. 9 is a perspective view showing a vertical drive mechanism of a dispensing head of the biosensor according to the first and second embodiments of the present invention.

A vertical drive mechanism 24 which moves the dispensing head 20 in a direction of an arrow Z is arranged for the dispensing head 20. The vertical drive mechanism 24, as shown in FIG. 9, includes a motor 24A and a drive shaft 24B arranged in the Z direction to move the dispensing head 20 in the Z direction. As shown in FIG. 3, the cold insulation portion 46, the correcting plate 45, the buffer supply portion 44B (buffer plate 44P), the measurement portion 30 (measurement chip 50), the sample setting portion 40B (sample plate 40P), and the pipet chip setting portion 42B (pipet chip stocker 42P), which are accessed by the dispensing head 20 to supply liquid, are arranged in the order named in the X direction (moving direction of the dispensing head 20).

As shown in FIG. 9, the dispensing head 20 has 12 dispensing pipes 20A. The dispensing pipes 20A are arranged in a line along a direction of an arrow Y orthogonal to the X direction. The two adjacent dispensing pipes 20A constitute one pair. One of the pair is to supply liquid, and the other is to discharge liquid. A pipet chip CP is attached to the distal end of the dispensing pipe 20A. The pipet chips CP are stoked in the pipet chip stocker 42P and can be exchanged as needed.

In measurement, a sample and buffer liquid are supplied to the measurement chips 50 by the dispensing pipes 20A. The supply of these liquids is performed as follows. More specifically, the dispensing head 20 is moved above the cold insulation portion 46, the sample setting portion 40B, and the buffer supply portion 44B. The sample and the buffer liquid are absorbed by the pipet chips CP attached to the six dispensing pipes 20A for supplying liquid. Amounts of absorption are amounts to be supplied into two flow paths. The pipet chips CP on the six dispensing pipes 20A which absorb the sample and the buffer liquid are inserted into one inlet/outlet ports 53 (to be referred to as "supply ports 53A" hereinafter) on the measurement flow path 55A side of the measurement chip 50, and the pipet chips CP attached to the six dispensing pipes 20A for discharging are inserted into the other inlet/outlet ports 53 (to be referred to as "discharge ports 53B" hereinafter). A half of the amount of liquid is supplied by the dispensing pipes 20A on the supply port 53A side, and the liquid is absorbed by the dispensing pipes 20A on the discharge port 53B. Subsequently, the other half of liquid in the pipet chips CP is similarly supplied to the reference flow path 55R.

The measurement portion 30, as shown in FIG. 4, includes an optical surface plate 32, a light-emitting portion 34, and a light-receiving portion 36. On the optical surface plate 32 in a side view, an upper part table 32A constituting a horizontal plane of the center of the upper part, a light-emitting slanted portion 32B which lowers in a direction away from the upper part table 32A, and a light-receiving slanted portion 32C arranged on the opposite side of the light-emitting slanted portion 32B through the upper part table 32A. On the upper part table 32A, the measurement chip 50 is set along the Y direction. On the light-emitting slanted portion 32B of the optical surface plate 32, a light-emitting portion 34 which emits the light beams L1 and L2 toward the measurement chip 50 is installed. The light-receiving portion 36 is installed on the light-receiving slanted portion 32C. A water-cooling jacket 32J which cools the optical surface plate 32 is arranged next to the optical surface plate 32.

Figure 10:
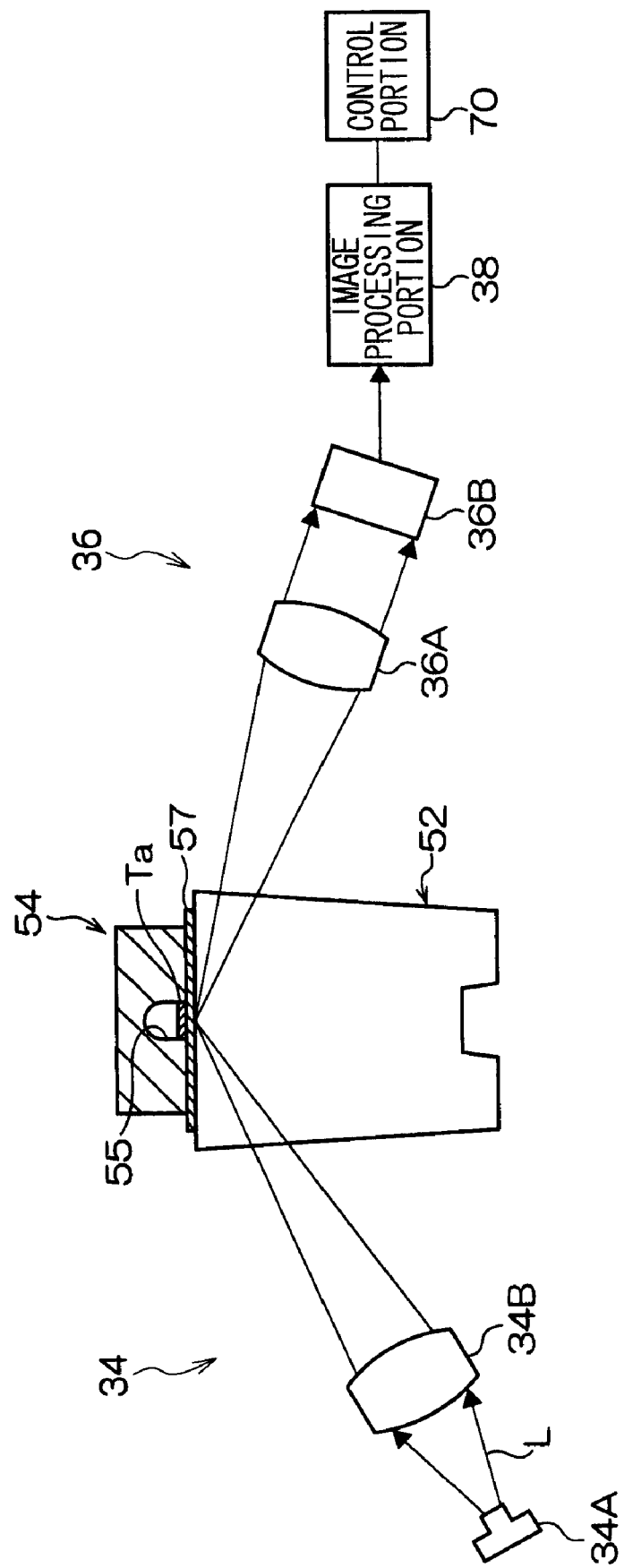
FIG. 10 is schematic view of the biosensor according to the first and second embodiments of the present invention near an optical measurement portion.

As shown in FIG. 10, the light-emitting portion 34 includes a light source 34A and a lens unit 34B. The light-receiving portion 36 includes a lens unit 36A and a CCD 36B. The CCD 36B is connected to an image processing portion 38 connected to a control portion 70 which controls the entire biosensor 10.

A diverged light beam L is emitted from the light source 34A. The lens unit 34B has a polarizing beam splitter for splitting the light beam L incident from the light source 34A into a P-polarized component and an S-polarized component and, further, the P-polarized component of the light beam L into two parallel, relatively thick, light beams L1 and L2 having a constant width in a Z-direction. The lens unit 34B makes the two parallel light beams L1 and L2 incident in a convergent light state to the measurement region E1 and the reference region E2 of the interface between the thin film 57 and the dielectric block 52 at various incidence angles equal to or larger than the total reflection angle with respect to the measurement range E1 and the reference range E2. As a result, the light beams L1 and L2 incident to the measurement region E1 and the reference region E2 are totally reflected at various reflection angles at the interface between the dielectric block 52 and the thin film 57. The light beams L1 and L2 thus totally reflected are imaged on the CCD 36B through the lens unit 36A. The CCD 36B is an area sensor having a light-receiving surface of such an area as can receive both of the two light beams L1 and L2 as totally reflected, and generates and outputs the image information indicating the image imaged on the light-receiving surface. The image information outputted is inputted to the image processing portion 38. The image processing portion 38 performs a predetermined processing on the basis of the image information inputted, and calculates and outputs to the control portion 70 the refractive index change data at the measurement region E1 and the reference region E2.

For the refractive index change data, the sample and the buffer liquid are individually supplied to the measurement chip 50, and the light beam L is emitted from the light-emitting portion 34 to irradiate the measurement region E1 and the reference region E2 respectively with the light beams L1 and L2, to thereby determine the dark line positions, at which the dark lines are generated in the light beams L1 and L2 totally reflected in the measurement region E1 and the reference region E2 respectively. In this case, the refractive index change data is determined on the basis of the difference between the difference in the dark line positions at which the dark line occurs in the measurement region E1 of the sample and the buffer liquid, and the difference in the dark line positions at which the dark line occurs in the reference region E2. The light beams L1 and L2, which are incident at specific incidence angles to the interface between the thin film 57 and the protein Ta, excite the surface plasmon at the interface. As a result, the reflected lights of the light beams L1 and L2 incident at the specific angles are sharply decreased in their intensities, and are observed as the dark lines. The incidence angles of the light beams L1 and L2 observed as the dark lines are total reflection attenuation angles $\theta_{SP}$, and the refractive index change data is determined on the basis of the change of the total reflection attenuation angles $\theta_{SP}$ depending on the reaction between the protein Ta and the sample A.

The control portion 70 measures, on the basis of the refractive index change data, the reaction between the protein Ta and the sample A, and displays the measurement result in the display 14.

Figure 11:
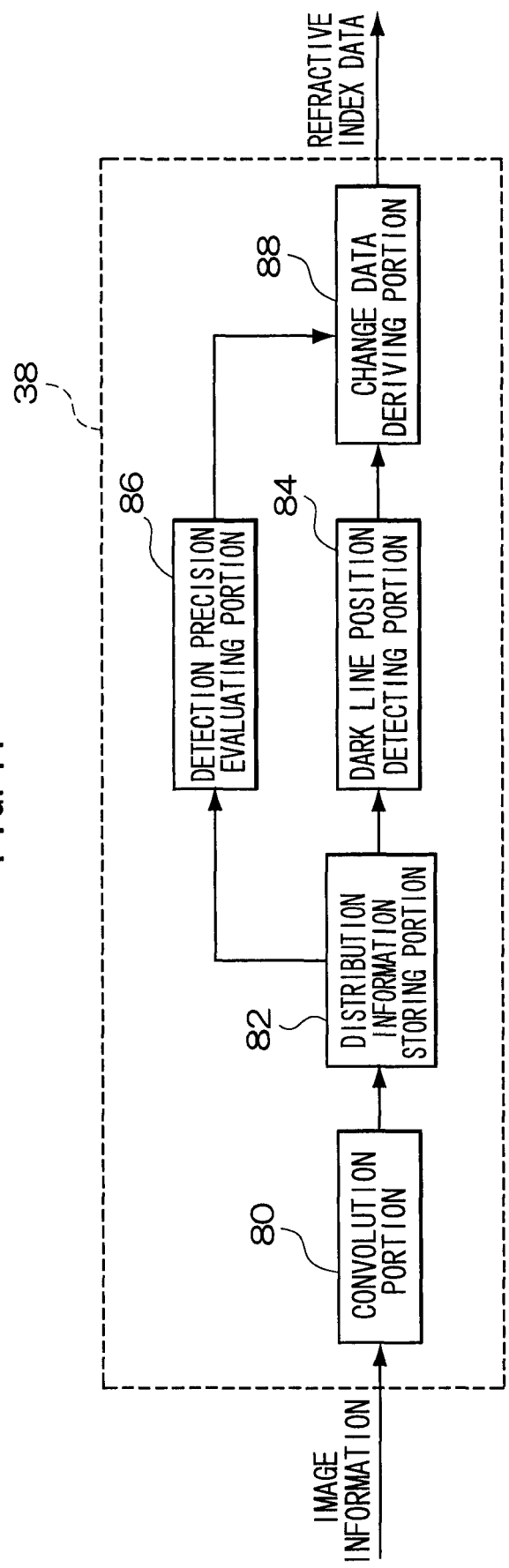
FIG. 11 is a block diagram showing a functional configuration of an image processing portion according to the first and second embodiments.

FIG. 11 is a functional block diagram showing a functional configuration of the image processing portion 38 according to this embodiment.

As shown in FIG. 11, the image processing portion 38 is constituted by: a convolution portion 80 for performing convolution of a two-dimensional image indicated by the image information, to thereby derive distribution information indicating one-dimensional light intensity distribution; a distribution information storing portion 82 for storing the distribution information derived; a dark line position detecting portion 84 for detecting the dark line position on the basis of the aforementioned distribution information; a detection precision evaluating portion 86 for detecting the detection precision of the dark line position, to thereby evaluate the detection precision; and a change data deriving portion 88 for deriving the refractive index change data on the basis of the dark line position detected by the dark line position detecting portion 84.

Here, the two-dimensional image indicated by the image information contains an image of the two light beams L1 and L2 totally reflected at the interface. Therefore, the convolution portion 80 according to this embodiment performs convolution of each region of the images of the light beams L1 and L2 of the two-dimensional image indicated by the image information, and derives the distribution information indicating the one-dimensional light intensity distributions of the light beams L1 and L2.

Next, the description is made on the operations of the biosensor 10 according to this embodiment when detecting the dark line positions.

In the case of deriving the refractive index change data, in the biosensor 10 according to this embodiment, the buffer liquid is supplied from the dispensing head 20 to the measurement chip 50 for the measurement first, and the measurement chip 50 is conveyed to the upper part table 32A by the measurement chip conveying mechanism 49, and the measurement region E1 of the measurement flow path 55A and the reference region E2 of the reference flow path 55R are arranged at the positions on which the light beams L1 and L2 are incident, respectively. Moreover, in the biosensor 10, the light beam is emitted from the light-emitting portion 34, to thereby irradiate the measurement region E1 and the reference region E2, respectively, with the light beams L1 and L2. The light beams L1 and L2 are totally reflected on the measurement region E1 and the reference region E2 and emitted, while being diverged, to the outside through the prism surface of the dielectric block 52. The light beams L1 and L2 thus emitted to the outside are imaged on the light-receiving surface of the CCD 36B through the lens unit 36A, so that the image information indicating the image imaged on the light-receiving surface is generated and outputted to the image processing unit 38.

Figure 12A:
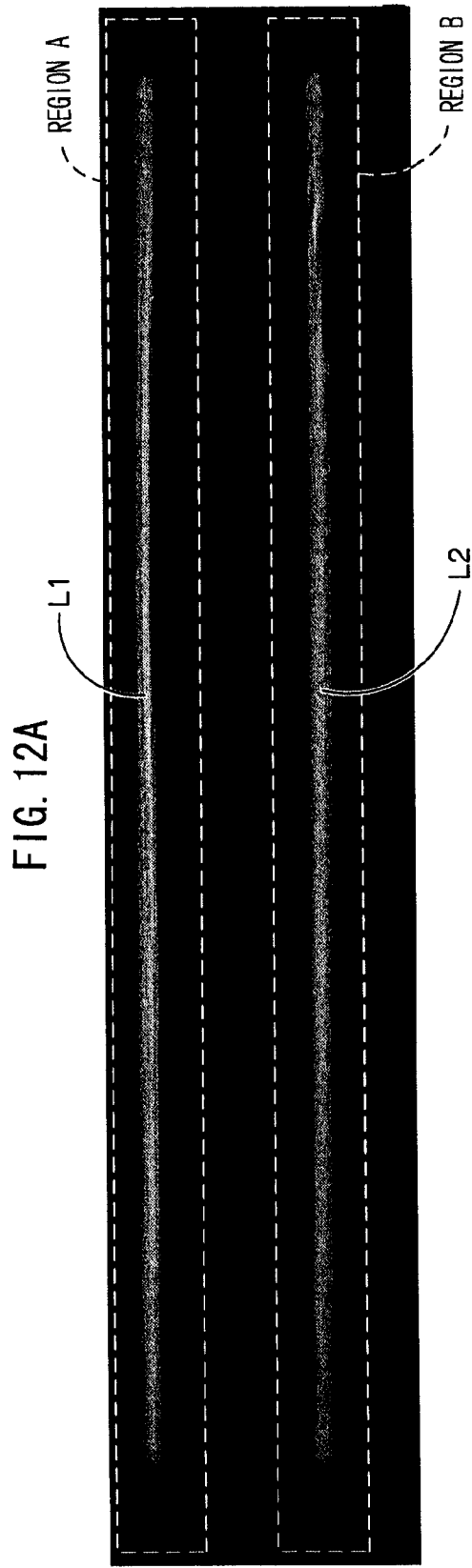
FIG. 12A is a view showing one example of an image containing two light beam images indicated by image information.

FIG. 12A shows one example of an image indicated by the image information.

As shown in FIG. 12A, the image indicated by the image information contains the images of the two light beams L1 and L2, which are totally reflected on the measurement region E1 and the reference region E2.

Figure 12B:
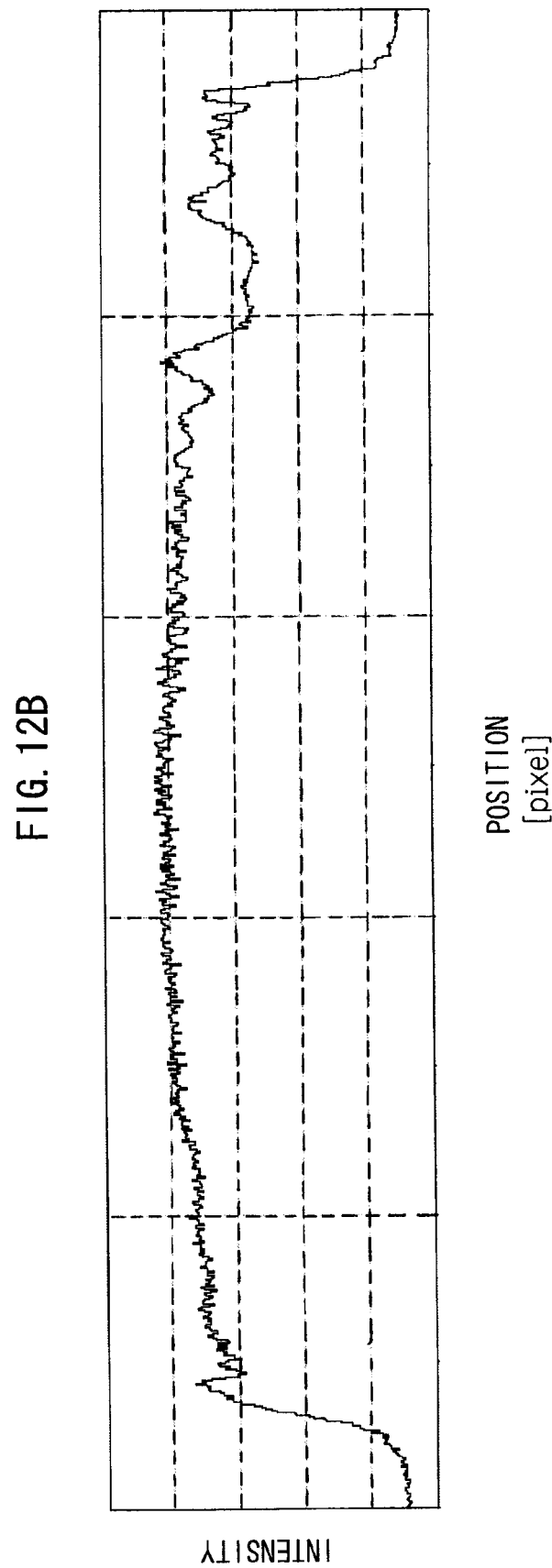
FIG. 12B is a graph presenting one example of the light intensity distribution of a light beam.

The convolution portion 80 (refer to FIG. 11) of the image processing portion 38 performs convolution of the image of a region A containing the image of the light beam L1 and the image of a region B containing the image of the light beam L2, of the image indicated by the input image information, respectively, and derives the distribution information indicating the one-dimensional light intensity distributions of the light beams L1 and L2, respectively. FIG. 12B shows the one-dimensional light intensity distribution of the light beam L2, as indicated by the distribution information derived through convolution of the image of the region B. Here in FIG. 12B, the abscissa indicates the reflection angle direction, and its individual positions correspond to the reflection angle.

The distribution information of the derived light beams L1 and L2 derived by the convolution portion 80 is stored in the distribution information storing portion 82.

Next, in the biosensor 10, the sample is supplied from the dispensing head 20 to the measurement chip 50 for the measurement. Like the aforementioned case of the buffer liquid, the measurement region E1 of the measurement flow path 55A for the measurement of the measurement chip 50 and the reference region E2 of the reference flow path 55R are arranged at the positions on which the light beams L1 and L2 are incident respectively. In the biosensor 10, moreover, the light beam is emitted from the light-emitting portion 34 to irradiate the measurement region E1 and the reference region E2 with the light beams L1 and L2, respectively. The light beams L1 and L2 are totally reflected on the measurement region E1 and the reference region E2, and are imaged on the light-receiving surface of the CCD 36B through the lens unit 36A so that the image information indicating the image imaged on the light-receiving surface is generated and outputted to the image processing portion 38.

The convolution portion 80, like the aforementioned case of the buffer liquid, performs convolution of the image of the region A containing the image of the light beam L1 and the image of the region B containing the image of the light beam L2, of the image indicated by the input image information, respectively, and derives the distribution information indicating the one-dimensional light intensity distributions of the light beams L1 and L2, respectively. The derived distribution information of the light beams L1 and L2 is stored in the distribution information storing portion 82.

As a result, the distribution information storing portion 82 stores the distribution information of the light beams L1 and L2, which are totally reflected in the measurement region E1 and the reference region E2 by supplying the sample and the buffer liquid individually to the measurement chip 50 for the measurement.

The image processing portion 38 performs the following refractive index change data deriving process to thereby derive the refractive index change data.

FIG. 13 is a flow chart showing a flow of the refractive index change data deriving process to be executed by the image processing portion 38 according to the first embodiment. The refractive index change data deriving process is described in the following with reference to FIG. 13.

At Step 102 of FIG. 13, the distribution information in the measurement region E1 and the reference region E2 at the time when the sample and the buffer liquid are individually supplied to the measurement chip 50 for the measurement is read out from the distribution information storing portion 82. At the Step 102, the dark line positions are individually detected from the light intensity distribution indicated by each distribution information.

Here at Step 102, the dark line positions are detected by performing the processing shown in FIG. 14A to FIG. 14E.

Specifically, at first, the light intensity distribution (FIG. 14A), as indicated by the read distribution information, is smoothed to determine the smoothed light intensity distribution (FIG. 14B). Next, the smoothed light intensity distribution is subtracted from the light intensity distribution indicated by the distribution information, to derive the differential intensity distribution (FIG. 14C). Then, a predetermined threshold value is added to each intensity indicated by the derived differential intensity distribution (FIG. 14D). Finally, the portion, where the intensity is zero or less in the differential intensity distribution having a predetermined threshold value added, is specified (FIG. 14E), and the dark line position is detected by determining the position of the center of gravity of the area of the portion where the intensity is zero or less.

At Step 102, moreover, the information indicating the detected dark line position is outputted to the change data deriving portion 88. Here, the processing of Step 102 corresponds to the processing of the dark line position detecting portion 84.

At next Step 104, the distribution information in the measurement region E1 and the reference region E2 at the time when the sample and the buffer liquid are individually supplied to the measurement chip 50 for the measurement is read from the distribution information storing portion 82. At Step 104, moreover, each light intensity distribution, as indicated by each read distribution information, is subject to the spatial frequency resolution to derive the light intensity distribution of each spatial frequency of the light beam, and the derived light intensity distribution is compared with each threshold value predetermined for each spatial frequency to thereby detect the detection precision of the dark line position.

At the Step 104, for each distribution information, the light intensity distribution of moving average of each predetermined width is determined from the light intensity distribution indicated by the distribution information, and the difference between the light intensity distribution of moving average and the corresponding light intensity distribution indicated by the distribution information is determined, so that the light intensity distribution of each spatial frequency is derived. After this, the difference between the maximum and the minimum of the difference is determined. These processings are performed several times while varying the width to thereby derive the noise volume of each spatial frequency contained in the light intensity distribution indicated by the distribution information.

Figure 15A:
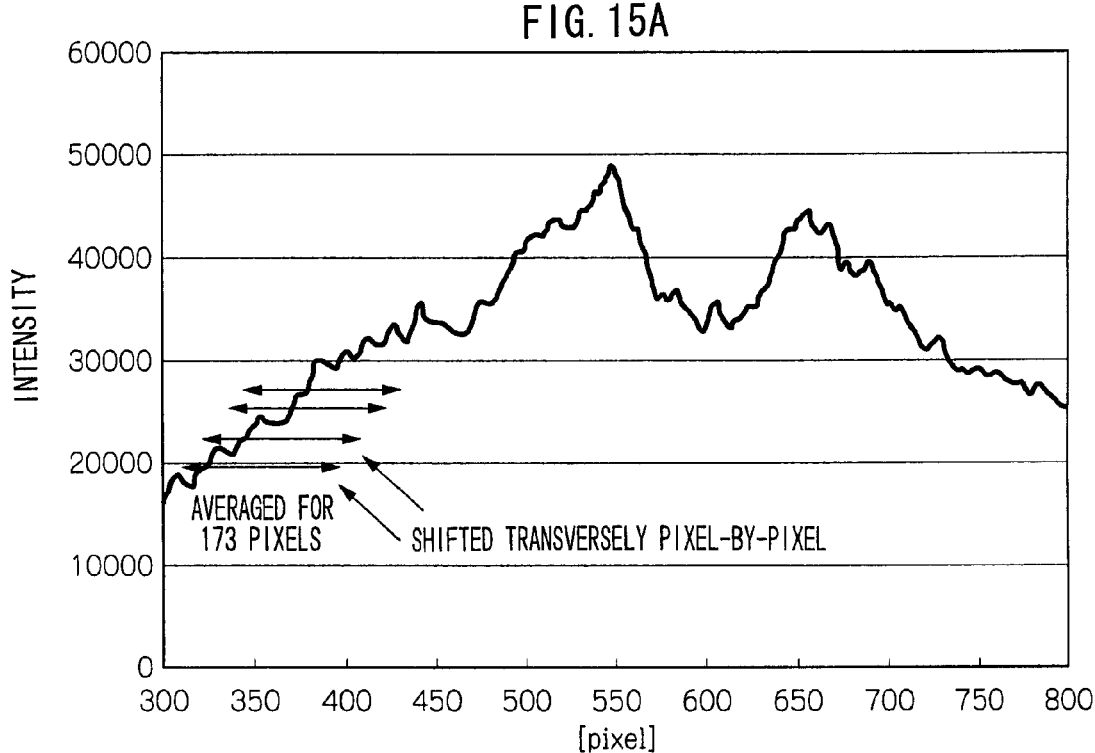
FIG. 15A is a graph presenting one example of the light intensity distribution of a light beam.
Figure 15B:
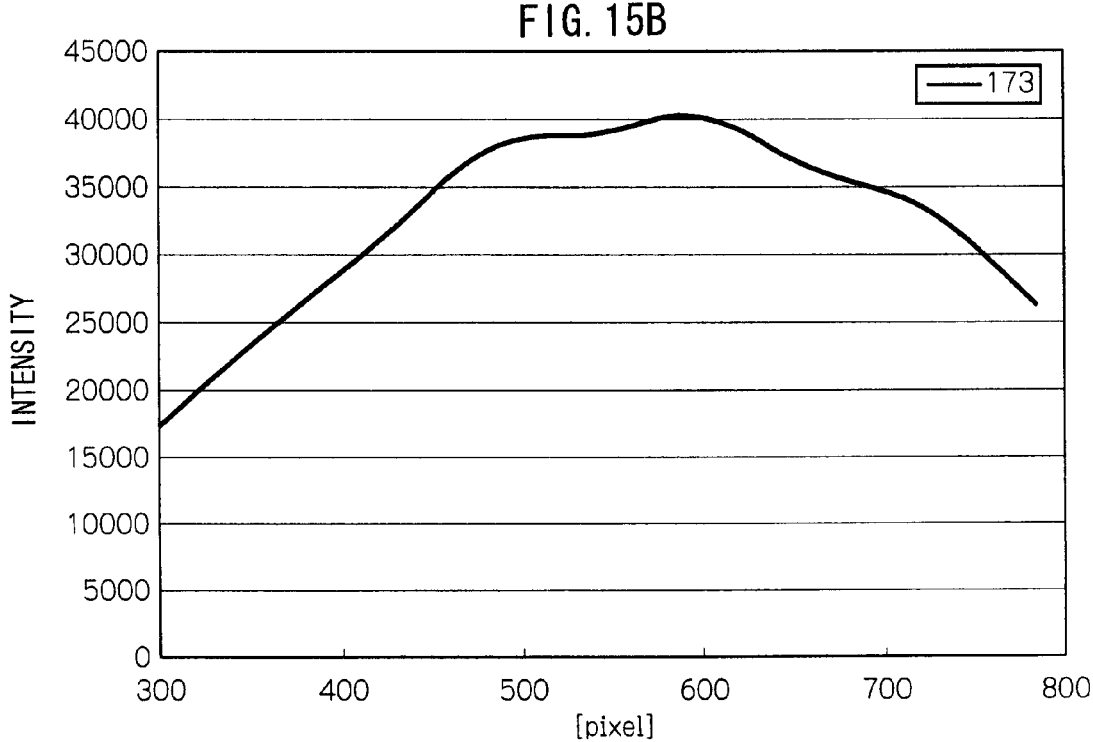
FIG. 15B is a graph presenting the light intensity distribution of a moving average.
Figure 16:
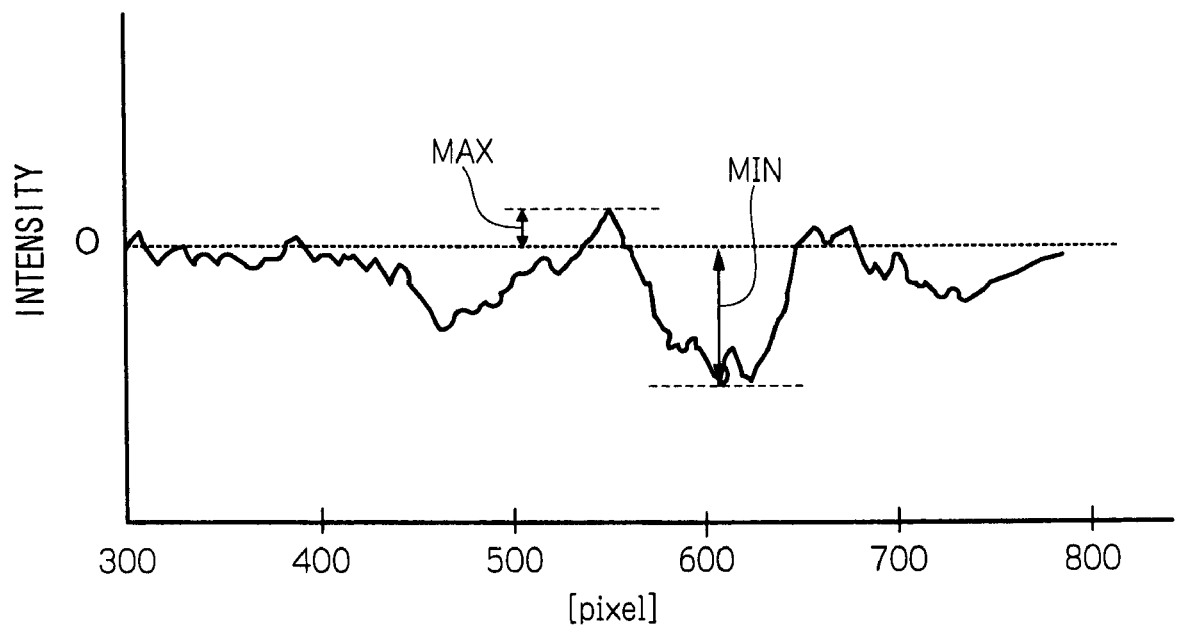
FIG. 16 is a graph presenting one example of the light intensity distribution.

For example, in the light intensity distribution indicated by the distribution information as shown in FIG. 15A, the individual intensity values are averaged by each predetermined width (e.g., a width of 86 pixels in either direction (or a width of 173 pixels total)) around each intensity value, and the averaged intensity values are plotted as the center value of the width, to thereby determine the light intensity distribution of the moving average, as shown in FIG. 15B. Next, the difference between the light intensity distribution of the moving average and the light intensity distribution indicated by the distribution information is determined to determine the differential intensity distribution, as shown in FIG. 16. Thereby, the high-frequency component due to the noise contained in the light intensity distribution indicated by the distribution information is extracted.

Then, the maximum noise volume is determined by subtracting the minimum MIN from the maximum MAX of the differential intensity distribution, as shown in FIG. 16. The more the noise contained in the light beams L1 and L2 is increased due to dust sticking to the dielectric block 52 or flaws occurring in the optical paths of the lens unit 34B or the lens unit 36A, the larger the maximum noise volume becomes.

These processings are performed several times while varying the aforementioned predetermined width, to determine the noise volume of the high-frequency component contained in the light intensity distribution indicated by the distribution information for each step.

At Step 104, the maximum noise volume of each width is compared with the threshold value predetermined for each width to thereby evaluate the detection precision of the dark line positions.

Figure 17A:
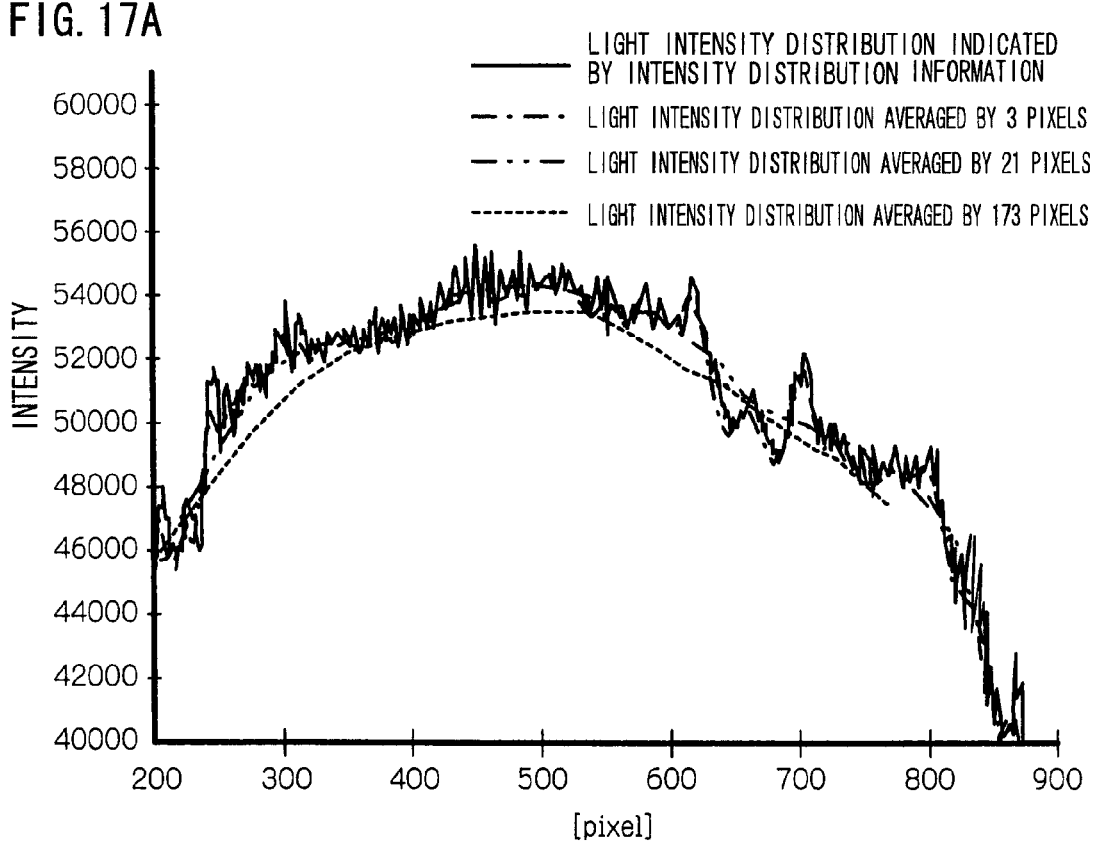
FIG. 17A is a graph presenting one example of the light intensity distribution of a light beam having low noise.
Figure 18A:
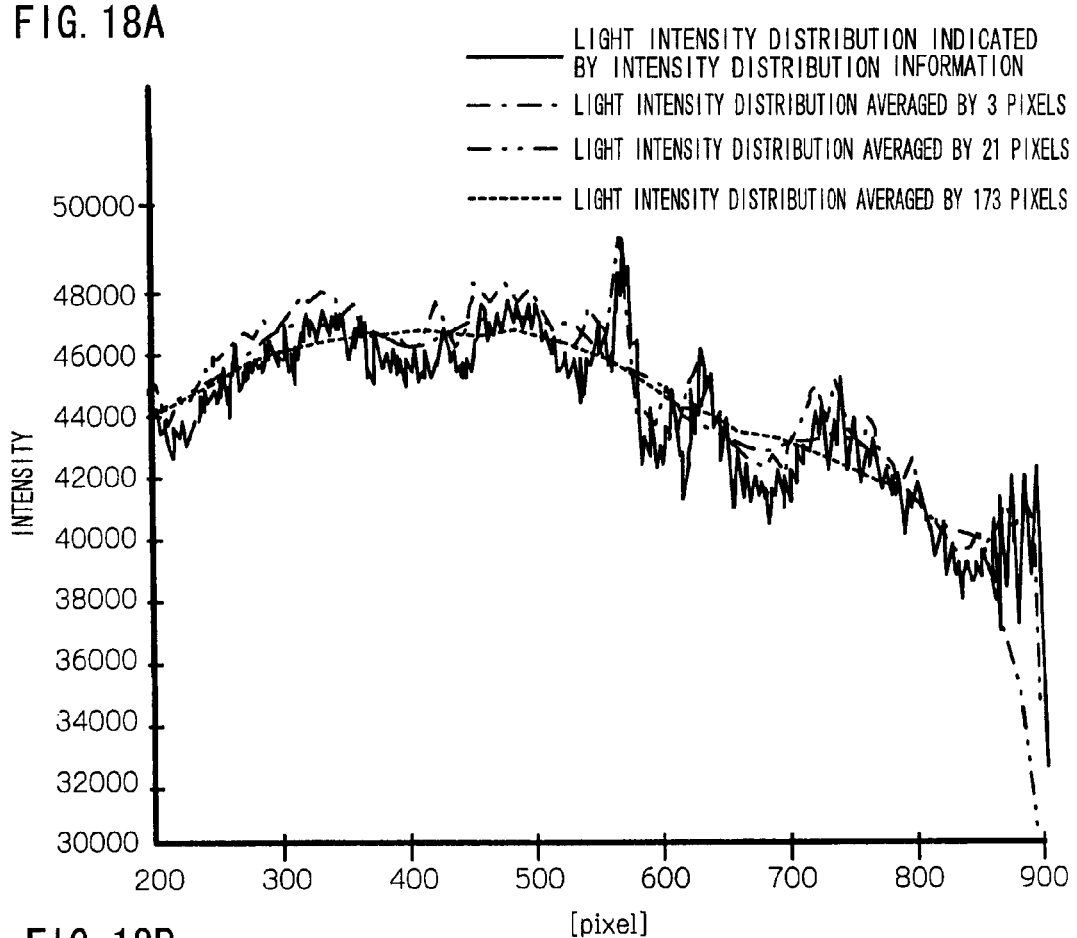
FIG. 18A is a graph presenting one example of the light intensity distribution of a light beam having high noise.

In each of FIG. 17A and FIG. 18A, a solid line indicates one example of the light intensity distribution indicated by the distribution information. In each of FIG. 17A and FIG. 18A, moreover, a long-dashed-short-dashed line, a long-dashed-double-short-dashed line, and a dashed line indicate, respectively, the light intensity distributions of the moving average, which are obtained by averaging the individual intensity values by 3 pixels, 21 pixels and 173 pixels before and after each intensity value of the light intensity distribution and by plotting the averaged intensity values as the center values of the widths.

Figure 17B:
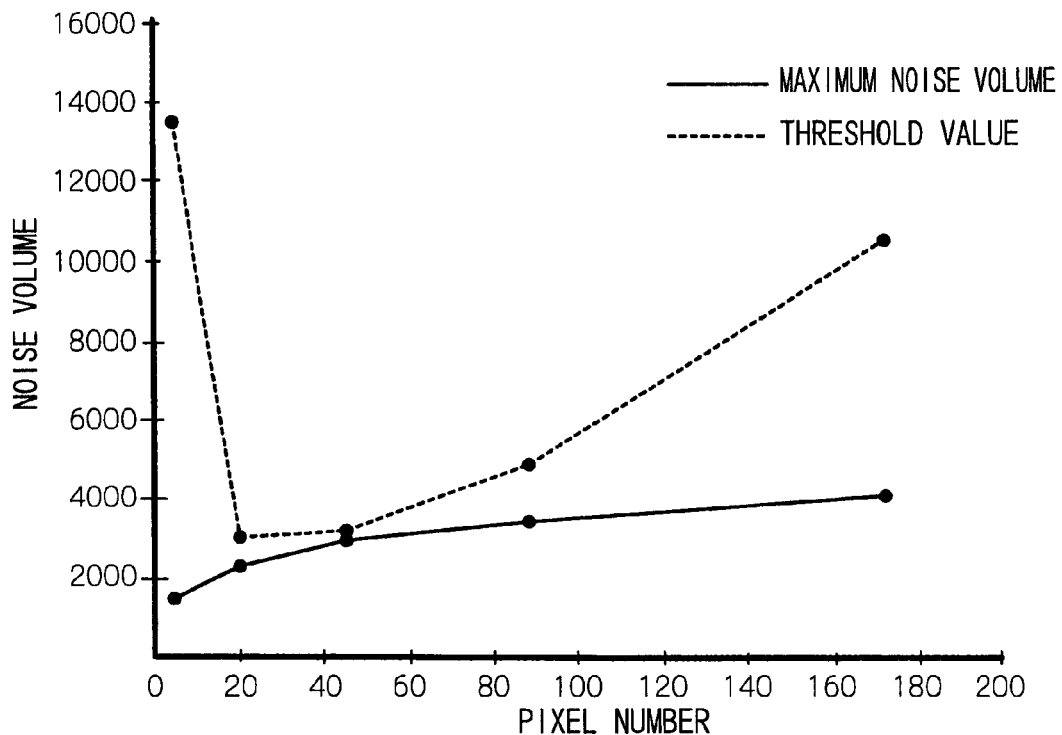
FIG. 17B is a graph presenting the comparison results of the maximum noise volume and the threshold value.

In FIG. 17B, a solid line indicates a graph plotting the maximum noise volume, which is determined by determining the difference between the light intensity distribution of each moving average, as shown in FIG. 17A, and the light intensity distribution indicated by the distribution information to thereby determine the differential intensity distribution, and by subtracting the minimum MIN from the maximum MAX of the differential intensity distribution, for each pixel number contained in the width averaged when the moving average is determined.

Figure 18B:
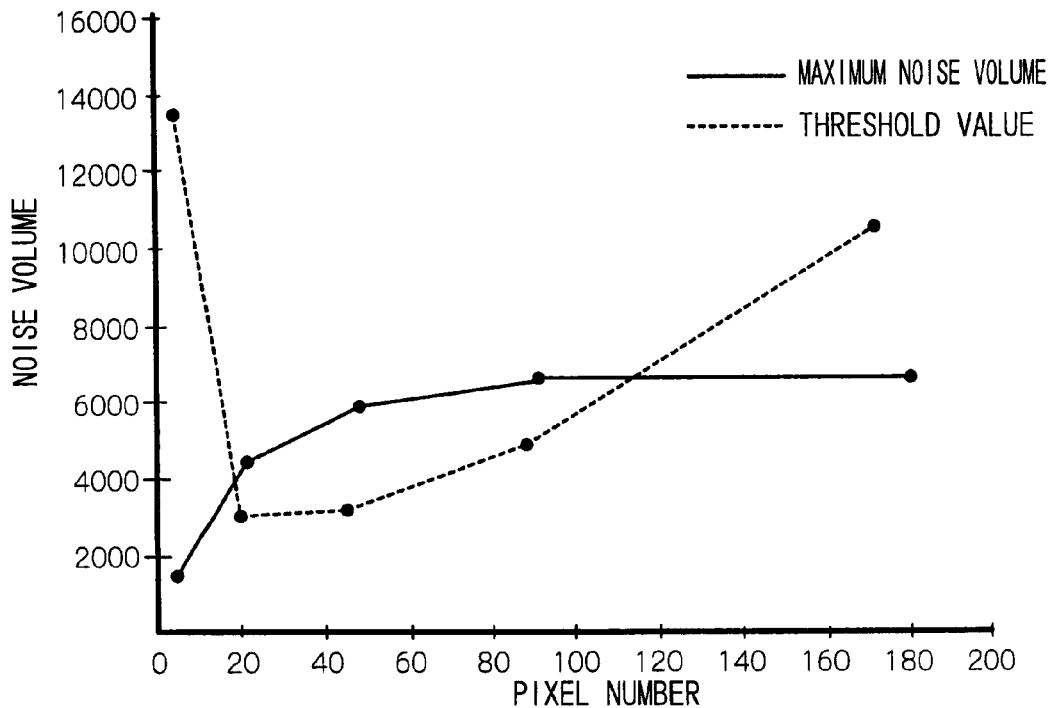
FIG. 18B is a graph presenting the comparison results of the maximum noise volume and the threshold value.

In FIG. 18B, a solid line indicates a graph plotting the maximum noise volume, which is determined by determining the difference between the light intensity distribution of each moving average, as shown in FIG. 18A, and the light intensity distribution indicated by the distribution information to thereby determine the differential intensity distribution, and by subtracting the minimum MIN from the maximum MAX of the differential intensity distribution, for each pixel number contained in the width averaged when the moving average is determined. Here, in each of FIG. 17B and FIG. 18B, a dashed line indicates the threshold values of each width (each pixel number contained in the width).

At the Step 104, it is decided whether or not the maximum noise volume of the light intensity distribution is equal to or less than the threshold value in all the pixel numbers in each read distribution information. In case the maximum noise volume is equal to or less than the threshold value in all the pixel numbers, the precision information indicating that the detection precision of the dark line position satisfies the desired precision is outputted. In case the maximum noise volume of the light intensity distribution is larger than the threshold value in any distribution information, the precision information indicating that the detection precision of the dark line position is lower than the desired precision is outputted to the change data deriving portion 88. Here, the processing of the Step 104 corresponds to the processing of the detection precision evaluating portion 86.

At next Step 106, for each of the measurement region E1 and the reference region E2, the difference is determined between the dark line position of the light intensity distribution indicated by the distribution information at the time of supplying the buffer liquid, and the dark line position of the light intensity distribution indicated by the distribution information at the time of supplying the sample, each as detected by the processing of the aforementioned Step 102. At the Step 106, moreover, the difference between the difference of the dark line positions in the measurement region E1 and the difference of the dark line positions in the reference region E2 is adopted as the refractive index change data, and the precision information is given to the refractive index change data and outputted to the control portion 70. Thus, the refractive index change data deriving process is ended. Here, the processing of the Step 106 corresponds to the processing of the change data deriving portion 88.

The control portion 70 is provided with the not-shown storing portion, which stores the refractive index change data and the precision information in a correlated manner. Moreover, the control portion 70 measures the reaction state between the protein Ta and the sample A on the basis of the difference between the difference of the dark line positions in the measurement region E1 and the difference of the dark line positions in the reference region E2, which is indicated by the refractive index change data stored in the storing portion, and causes the display 14 to display the measurement result and whether or not the detection precision satisfies the desired precision on the basis of the precision information.

Next, the procedure for determining the threshold value of each width is described in the following.

Figure 19A:
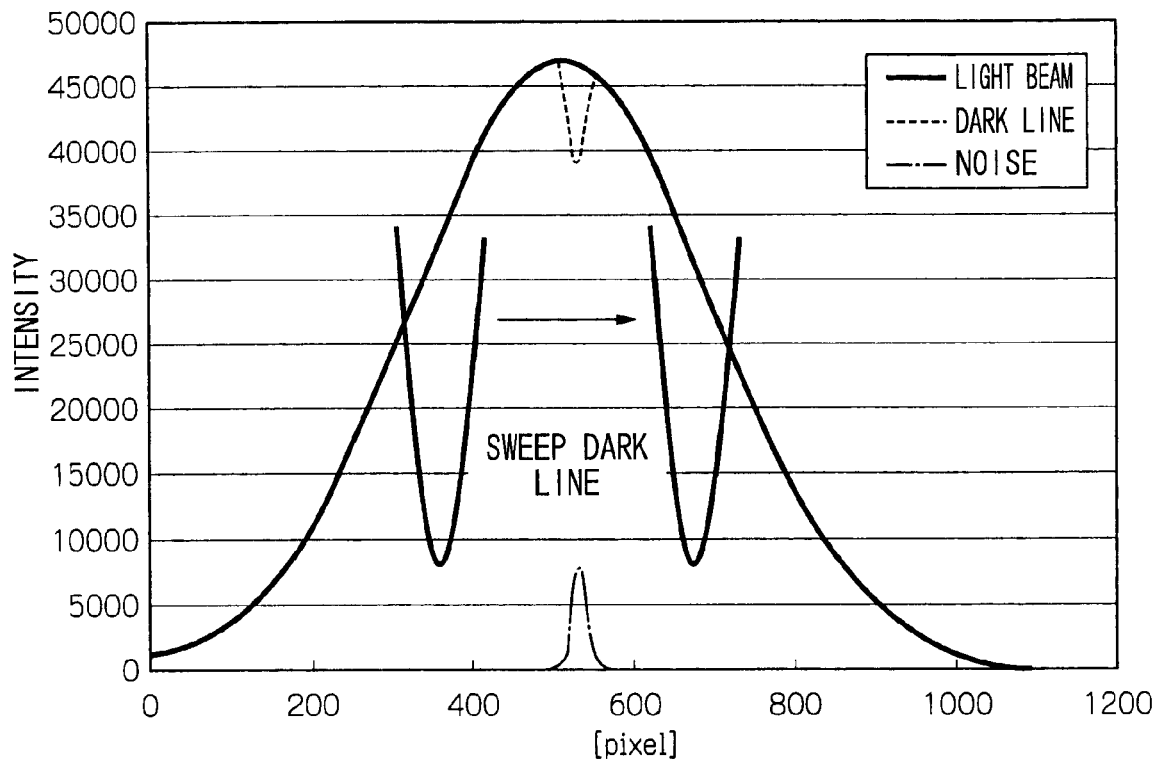
FIG. 19A is a graph presenting the light intensity distribution of a light beam in the case of a normal distribution.
Figure 20A:
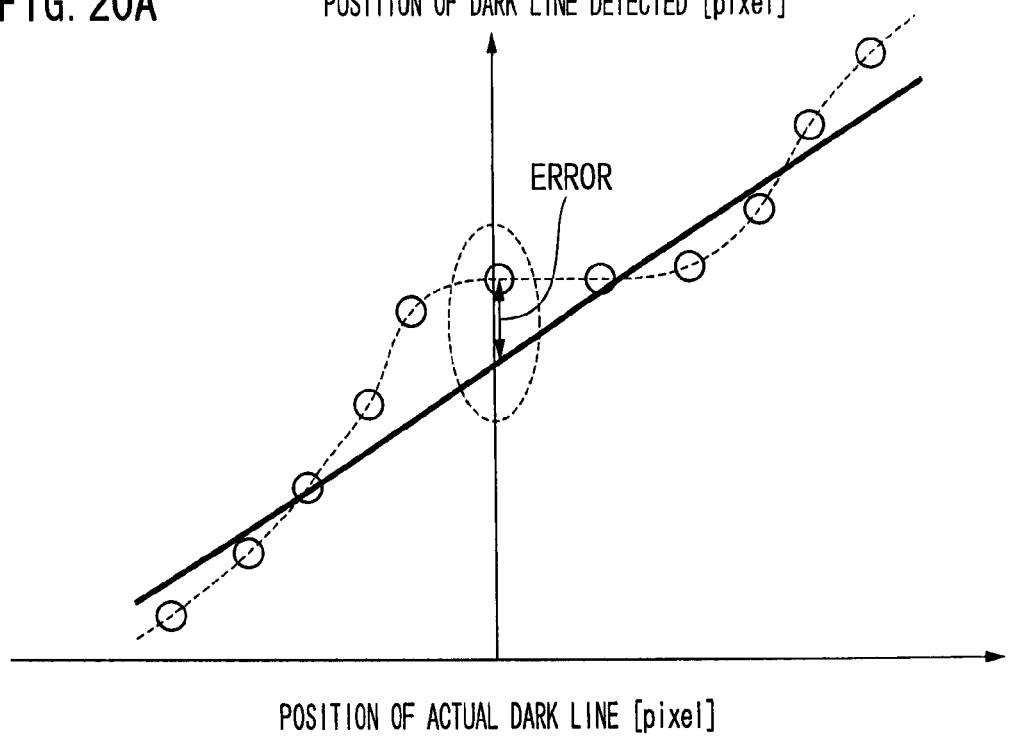
FIG. 20A is a graph presenting a relation between a dark line position detected and the center position of an actual dark line swept.

It is assumed that the light intensity distribution indicated by the distribution information is a normal distribution having a half-width of 400 pixels, an amplitude of 47000 and a center position of 500 pixels, as shown in FIG. 19A, for example. With this light intensity distribution, the dark line is swept from one side to the other of the light intensity distribution, and the dark line position is detected by the aforementioned method which has been described with reference to FIG. 14A to FIG. 14E. In this case, the dark line position detected and the center position of the actual dark line swept are in a proportional relation, as indicated by a solid line in FIG. 20A.

Figure 19B:
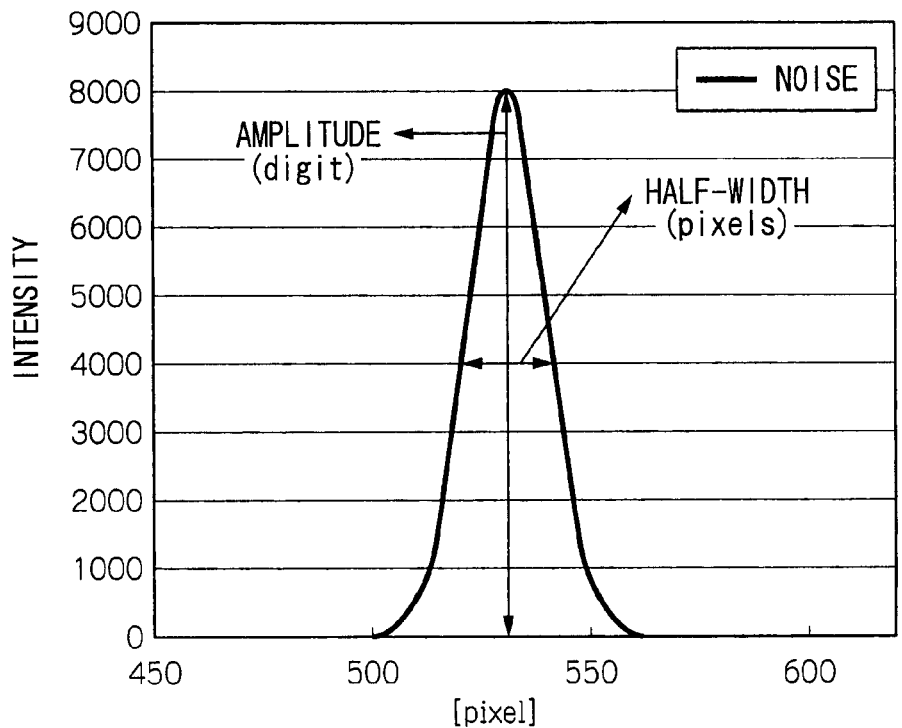
FIG. 19B is a graph presenting the light intensity distribution of noises.

In the light intensity distribution of the light beam, as shown in FIG. 19A, on the other hand, the dark line is swept from one side to the other side of the light intensity distribution. The noises, as shown in FIG. 19B, are added to the differential intensity distribution, to which a predetermined threshold value is added by the method described with reference to FIG. 14A to FIG. 14D. In this differential intensity distribution having the noises added, the dark line position is detected by the method described with reference to FIG. 14E. In this case, the position of the dark line detected and the center position of the actual dark line swept are in the relation, as indicated by a dashed line of FIG. 20A. In short, an error is caused in the detected dark line position due to the influences of noises.

Figure 20B:
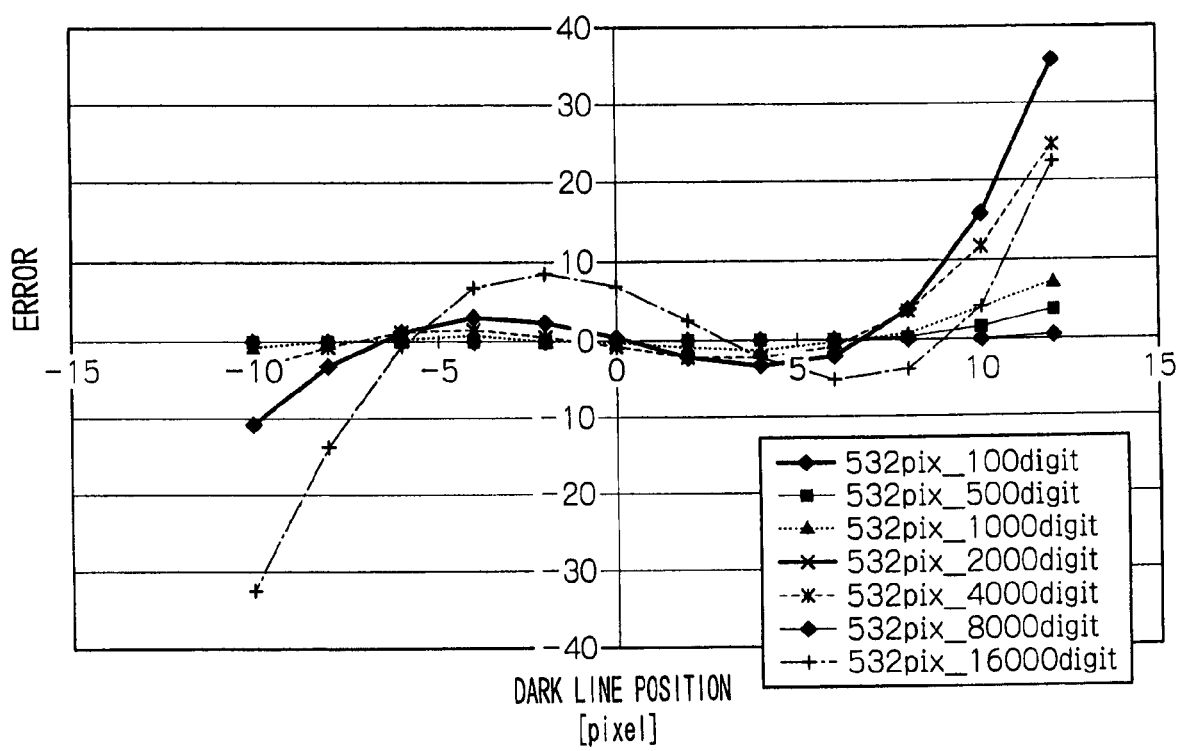
FIG. 20B is a graph presenting relations between the dark line positions and the errors with reference to the center position of noises.

FIG. 20B shows the relations between the dark line positions and the errors with reference to the center position of the noises, in case the dark line positions are detected with the center position of the noises added of 532 pixels and the noise half-width of 22 pixels and the noise amplitudes varied to 100, 500, 1000, 2000, 4000, 8000 and 16000.

Figure 21A:
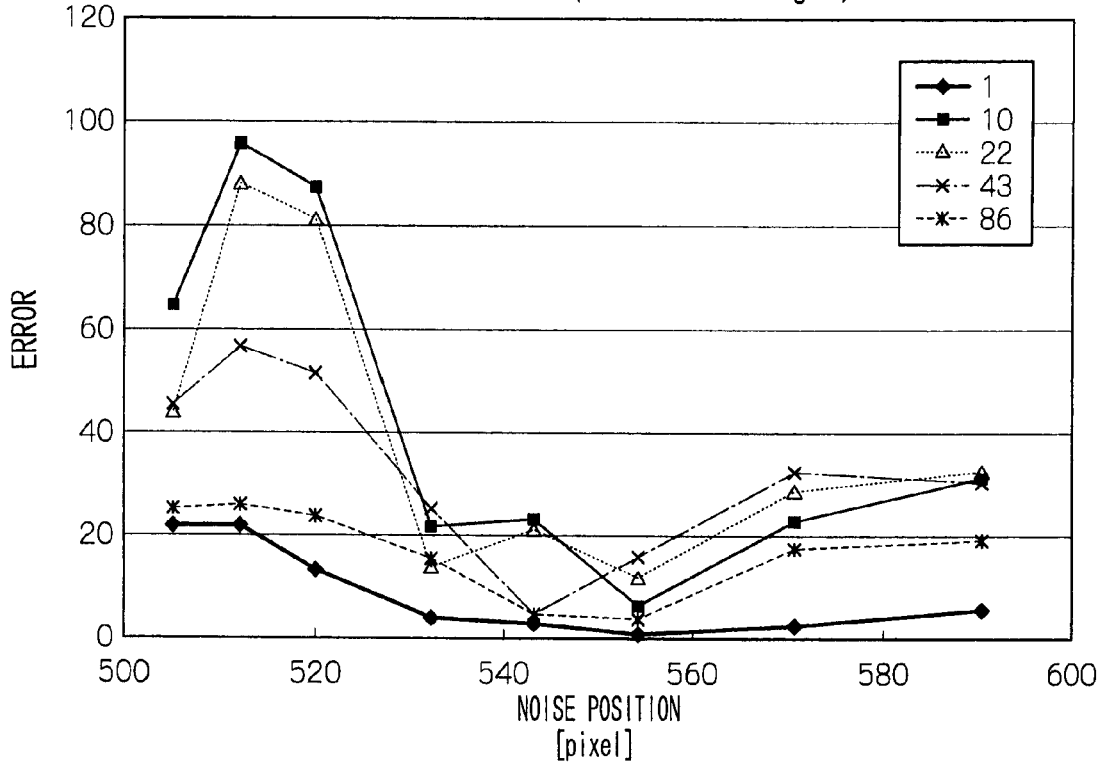
FIG. 21A is a graph presenting relations between the half-widths of noises and the errors of the cases in which the half-widths of noises are varied to detect the dark line positions.
Figure 22:
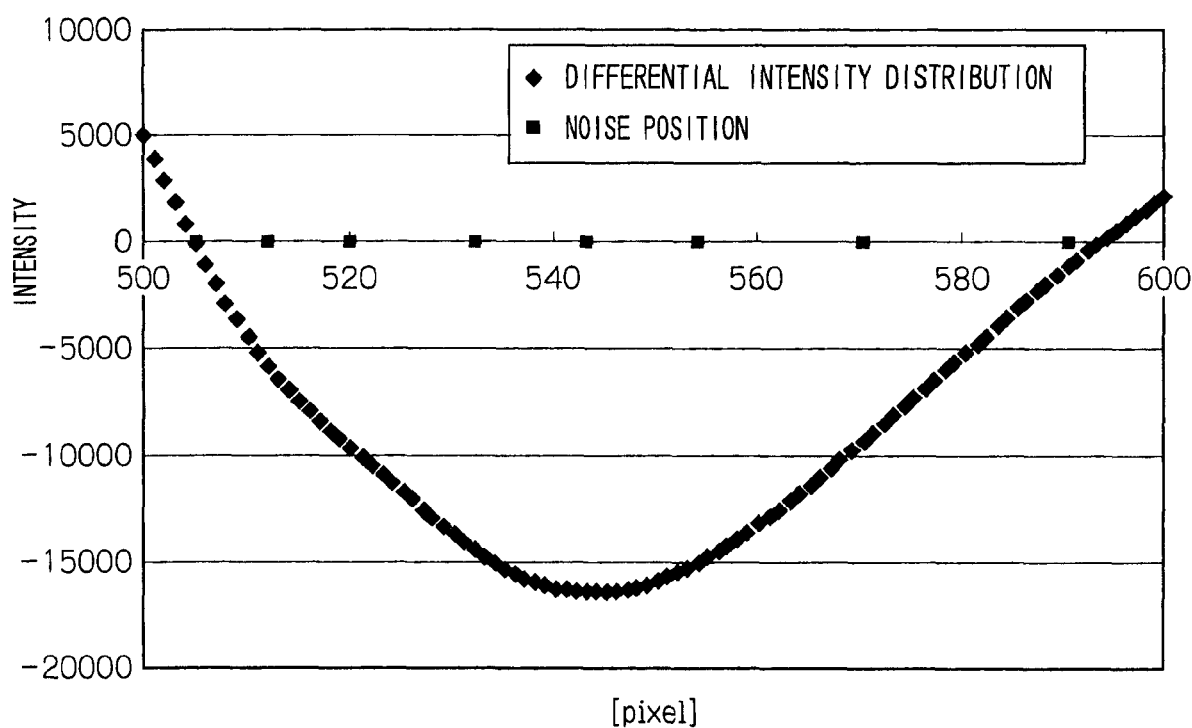
FIG. 22 is a graph presenting one example of a differential intensity distribution.

FIG. 21A shows the relations between the half-width of noises and the errors in the individual positions, in case the dark line positions are detected by positioning the noises individually in the individual positions of 505 pixels, 512 pixels, 520 pixels, 532 pixels, 543 pixels, 554 pixels, 570 pixels and 590 pixels of the differential intensity distributions as shown in FIG. 22, to which a predetermined threshold value (e.g., 3000) is added by the method described with reference to FIG. 14A to FIG. 14D, by setting the noise amplitude to 8000, and by varying the noise half-width to 1 pixel, 10 pixels, 22 pixels, 43 pixels and 86 pixels.

Figure 21B:
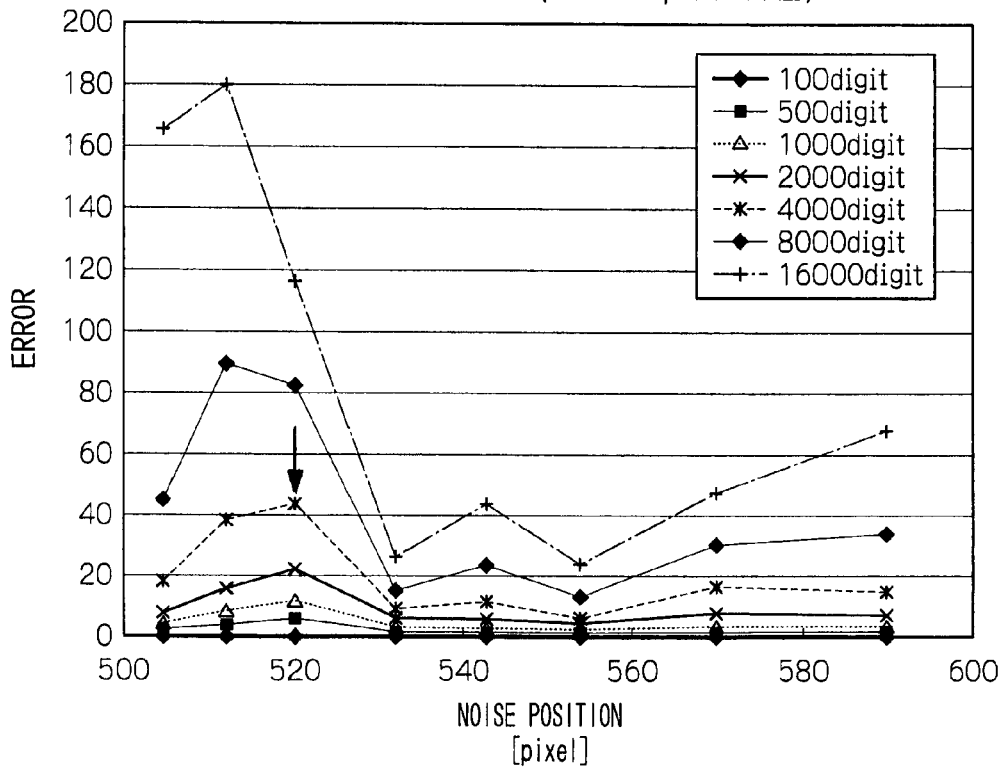
FIG. 21B is a graph presenting relations between the amplitudes of noises and the errors of the cases in which the amplitudes of noises are varied to detect the dark line positions.

FIG. 21B shows the relations between the half-width of noises and the errors in the individual positions, in case the dark line positions are detected by positioning the noises individually in the individual positions of 505 pixels, 512 pixels, 520 pixels, 532 pixels, 543 pixels, 554 pixels, 570 pixels and 590 pixels of the differential intensity distributions as shown in FIG. 22, by setting the half-width of noises to 22 pixels, and by varying the amplitude of noises to 100, 500, 1000, 2000, 4000, 8000 and 16000.

Because the dust sticks to the dielectric block 52 or because flaws occur in the optical paths of the lens unit 34B or the lens unit 36A, the amplitude of noises to actually occur in the light beam is generally 4000 or less. Thus, in case the amplitude of noises is 4000 or less, the errors become the largest in case the noise position is in the vicinity of 520 pixels, as indicated by an arrow in FIG. 21B. As shown in FIG. 21A, moreover, the errors become the largest in case the noise half-width is 10 pixels or 22 pixels.

Figure 23:
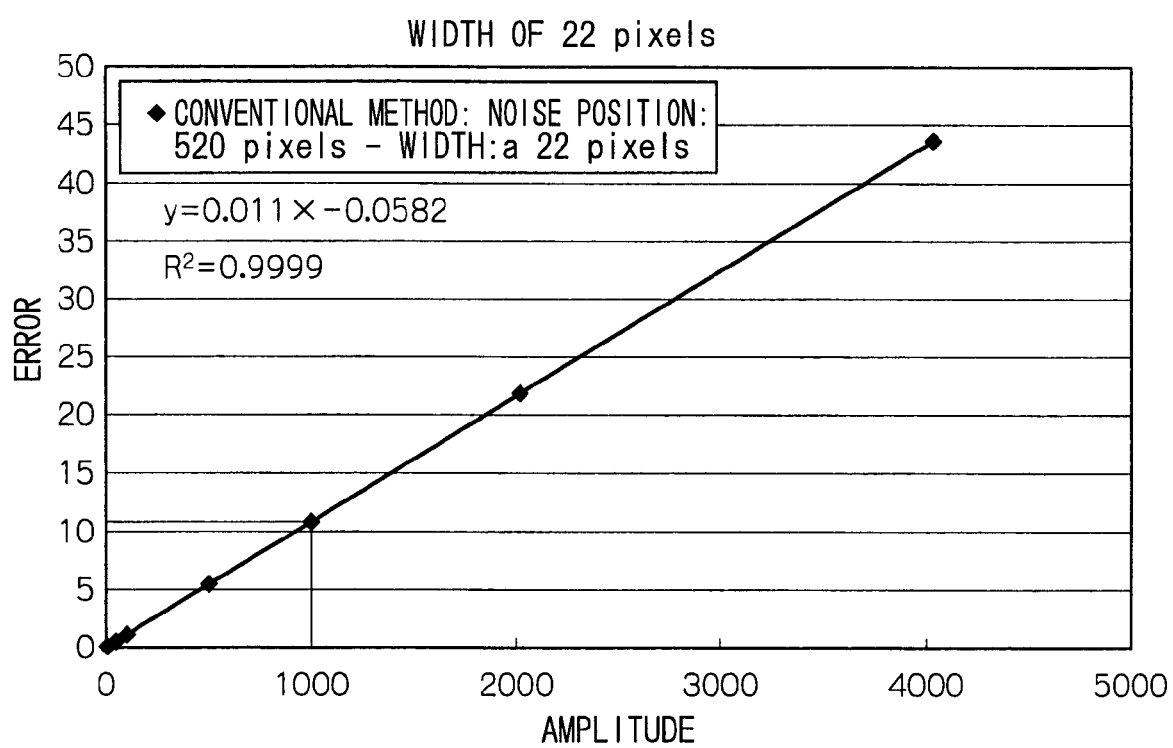
FIG. 23 is a graph presenting a relation between the amplitude and the error of the case in which the amplitude of noises is varied.

FIG. 23 shows a relation between the amplitude and the error of the case in which the noise position is 520 pixels and the noise half-width is 22 pixels and the noise amplitude is varied.

In the biosensor 10 according to this embodiment, the allowable noise amplitude is 1000 or less, in case the allowable errors are within 12 pixels, for example.

FIG. 24A shows the errors of the case in which the noise position is 520 pixels and the noise amplitude is 1000 and the noise half-width is varied.

As shown in FIG. 24A, the errors become the largest in case the noise half-width is 10 pixels. As shown in FIG. 24B, therefore, the amplitude of 1000 pixels is the threshold value, in case the noise half-width is 10 pixels. For the portion other than the noise half-width of 10 pixels, the threshold value of each noise width is determined by 1000×the error ("12" in this case) in case of the half-width of 10 pixels/the error in case of another half-width. In case the noise half-width is 86 pixels, for example, the errors are about 2, so that the threshold value is determined by 1000×12/2=6000. Here in FIG. 24B, in order to average the entire light intensity distribution of noises to be detected, the pixel number of the width to be averaged by the moving average is twice as large as the pixel number of the half-width.

In the biosensor 10 according to this embodiment, the threshold values thus obtained are stored in advance in the detection precision evaluating portion 86.

By using the threshold values indicated in FIG. 24B, the detection precision evaluating portion 86 according to this embodiment can detect the case, in which the errors become larger than 12 pixels because the noises are contained.

According to the embodiment thus far described, the convolution is performed by the convolution portion 80 to acquire the distribution information indicating the light intensity distribution of the light beam, which is incident at a plurality of angles to the dielectric block 52 so as to be totally reflected at the interface between the dielectric block 52 and the thin film 57. The spatial frequency resolution is performed on the light intensity distribution indicated by the acquired distribution information by the detection precision evaluating portion 86, to thereby derive the light intensity distribution of each spatial frequency of the light beam. The derived light intensity distribution is compared with the threshold value predetermined for each spatial frequency, to thereby detect the detection precision of the dark line position. As a result, it is possible to detect that the detection precision of the dark line position is decreased.

According to the embodiment, moreover, the light intensity distribution of each spatial frequency can be derived by the simple calculation to determine the light intensity distribution of the moving average of each predetermined width from the light intensity distribution indicated by the distribution information, and to determine the difference between the light intensity distribution of the moving average and the corresponding light intensity distribution indicated by the distribution information.

According to the embodiment, moreover, the precision information is added to the refractive index change data so that the precision of the measurement result determined on the basis of the refractive index change data can be decided.

Second Embodiment

The second embodiment is described on the case, in which the spatial frequency resolution is performed by performing the Fourier transformation on the light intensity distribution indicated by each distribution information, to derive the light intensity distribution of each spatial frequency of the light beam.

The constitution of the biosensor 10 and the constitution of the image processing portion 38 according to the second embodiment are omitted on their description, because they are identical to those of the first embodiment (refer to FIG. 1 to FIG. 11).

Here, the detection precision evaluating portion 86 (refer to FIG. 11) of the image processing portion 38 according to the second embodiment performs the fast Fourier transformation as the Fourier transformation on the light intensity distribution indicated by the distribution information, to thereby determine the light intensity distribution of each spatial frequency, and compares the light intensity distribution with the threshold value predetermined for each spatial frequency, to thereby detect the decrease in the detection precision of the dark line position.

FIG. 25 is a flow chart showing a flow of the refractive index change data deriving process to be executed by the image processing portion 38 according to the second embodiment. Here, the same processings of FIG. 25 as those of FIG. 13 are omitted on their description by designating them by the same reference numerals as those of FIG. 13.

At Step 105, the distribution information in the measurement region E1 and the reference region E2 at the time when the sample and the buffer liquid are individually supplied to the measurement chip 50 for the measurement, is read out from the distribution information storing portion 82. At Step 105, moreover, the fast Fourier transformation is performed on the light intensity distribution indicated by each distribution information read out, to thereby determine the light intensity distribution of each spatial frequency.

Figure 26A:
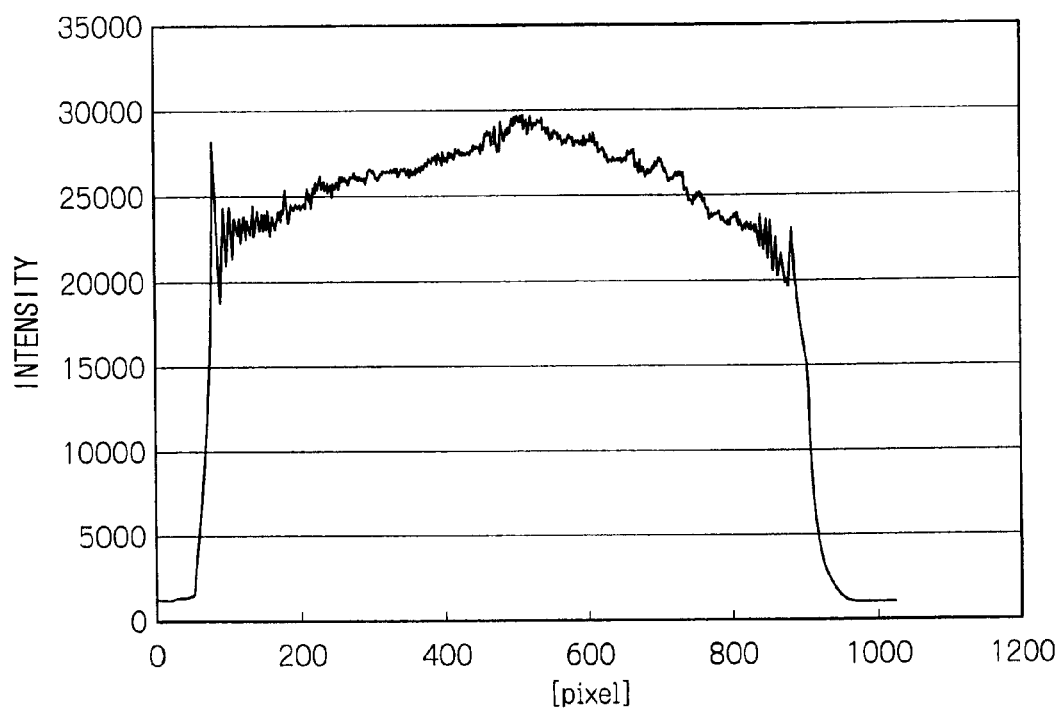
FIG. 26A is a graph presenting one example of the light intensity distribution of a light beam having low noises.
Figure 26B:
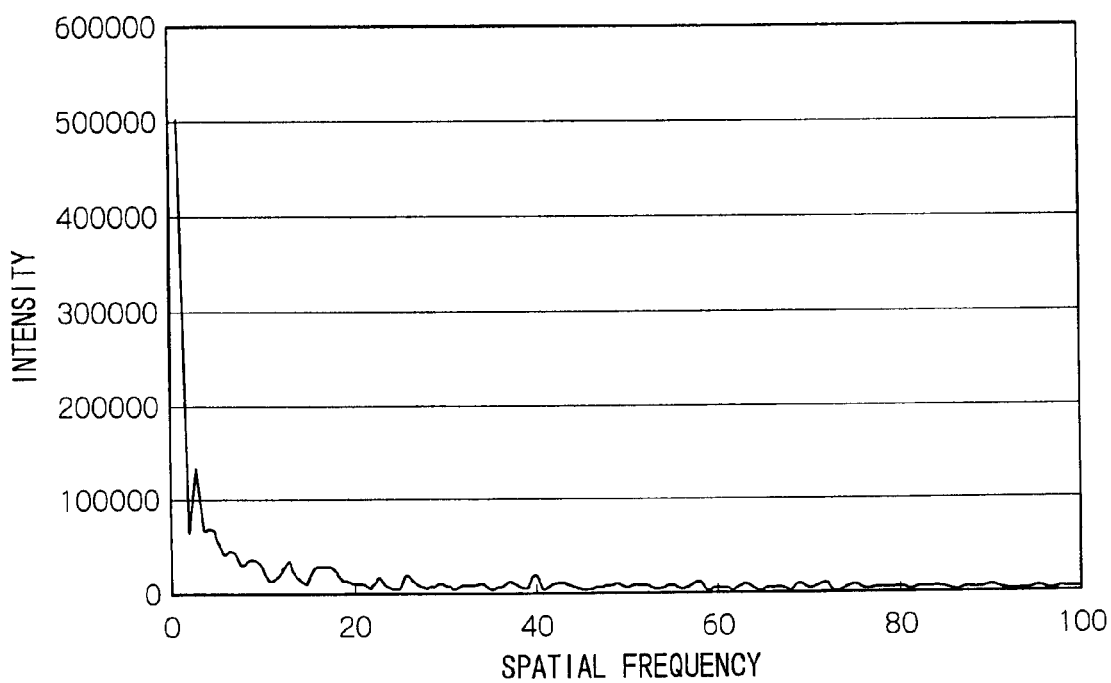
FIG. 26B is a graph presenting the light intensity distributions of every spatial frequencies.
Figure 27A:
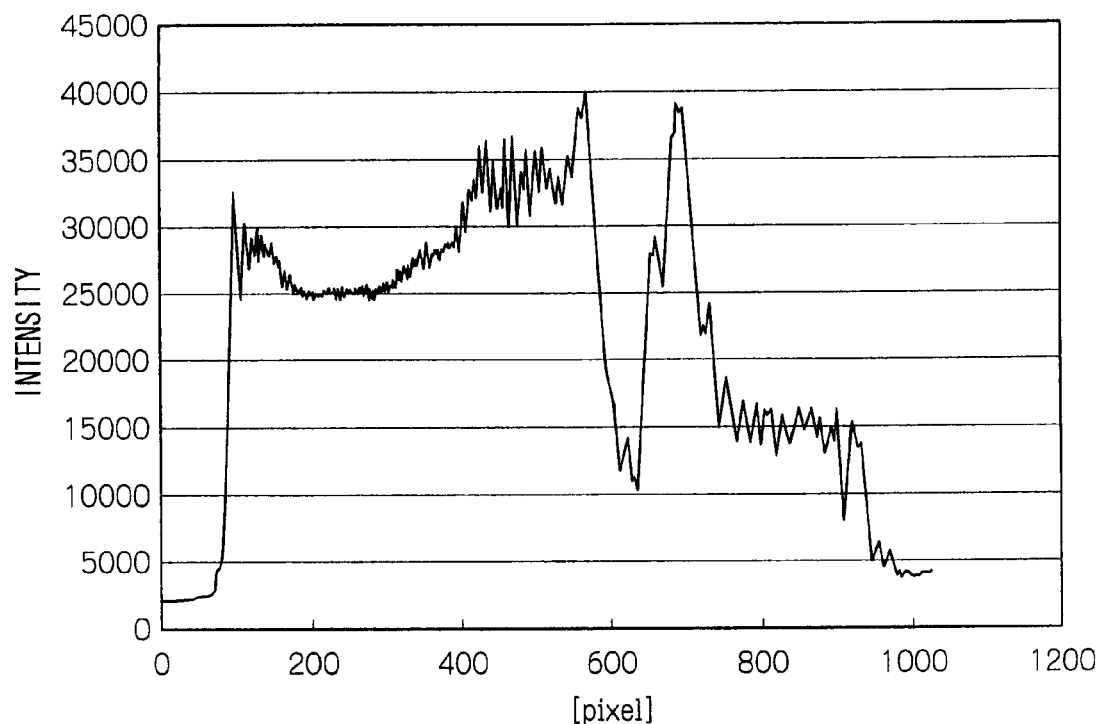
FIG. 27A is a graph presenting one example of the light intensity distribution of a light beam having high noises.
Figure 27B:
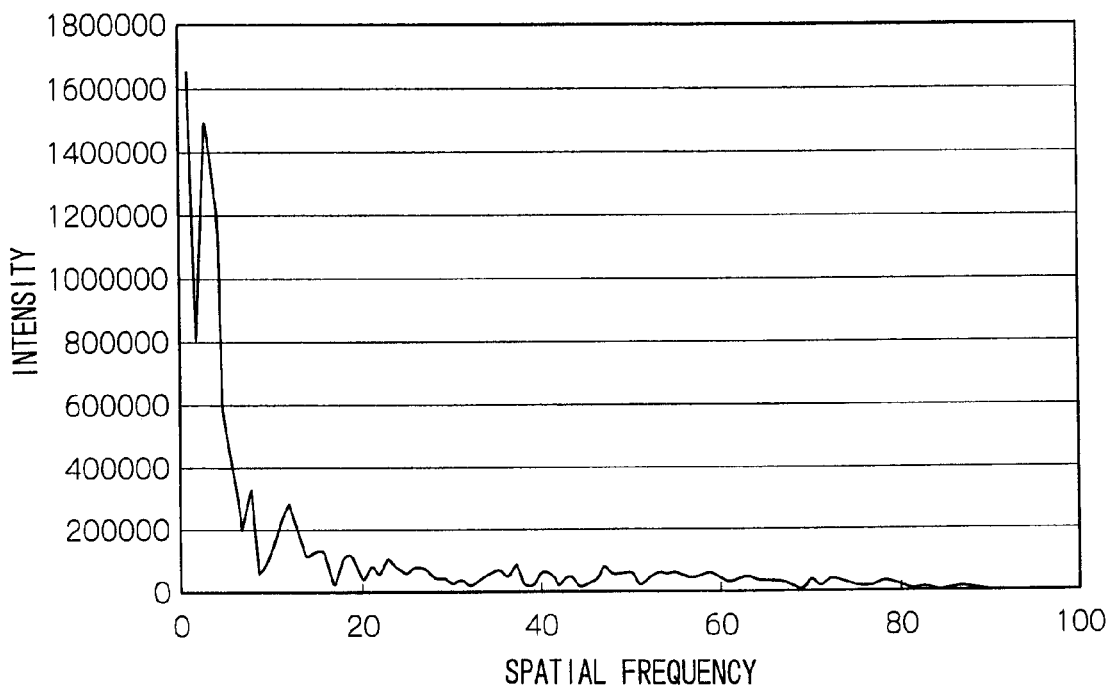
FIG. 27B is a graph presenting the light intensity distributions of every spatial frequencies.

As a result, the light intensity distribution indicated by the distribution information, as shown in FIG. 26A, for example, is transformed into the light intensity distribution of each spatial frequency as shown in FIG. 26B. The light intensity distribution indicated by the distribution information, as shown in FIG. 27A, is transformed into the light intensity distribution of each spatial frequency as shown in FIG. 27B.

At the Step 105, moreover, the light intensity distribution of each spatial frequency, in which each distribution information is subject to the fast Fourier transformation, is compared with a threshold value predetermined for each spatial frequency. In case the light intensity distribution of each spatial frequency is equal to or less than the threshold value in all the read distribution information, the precision information indicating that the detection precision of the dark line position satisfies the desired precision is outputted. In case any distribution information has a portion where the light intensity distribution of each spatial frequency is larger than the threshold value, the precision information indicating that the detection precision of the dark line position is lower than the desired precision is outputted.

Figure 28A:
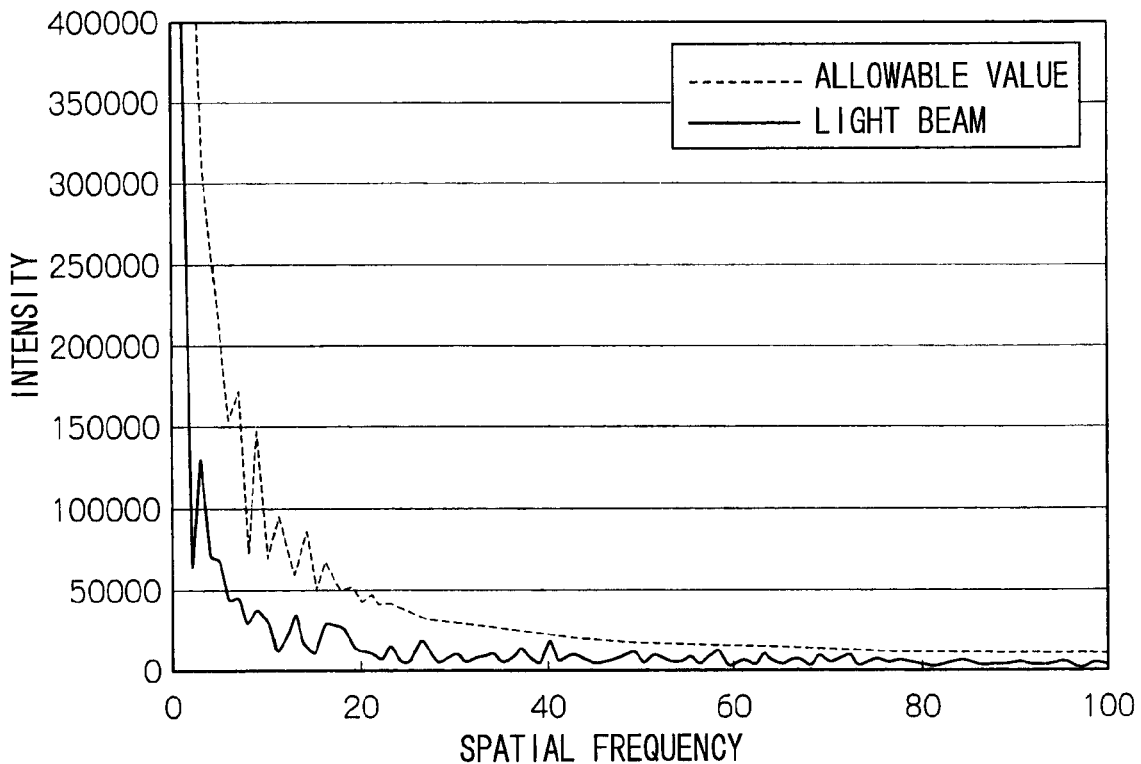
FIG. 28A is a graph presenting the comparison results of the light intensity distribution of every spatial frequencies presented in FIG. 26B and the threshold value.
Figure 28B:
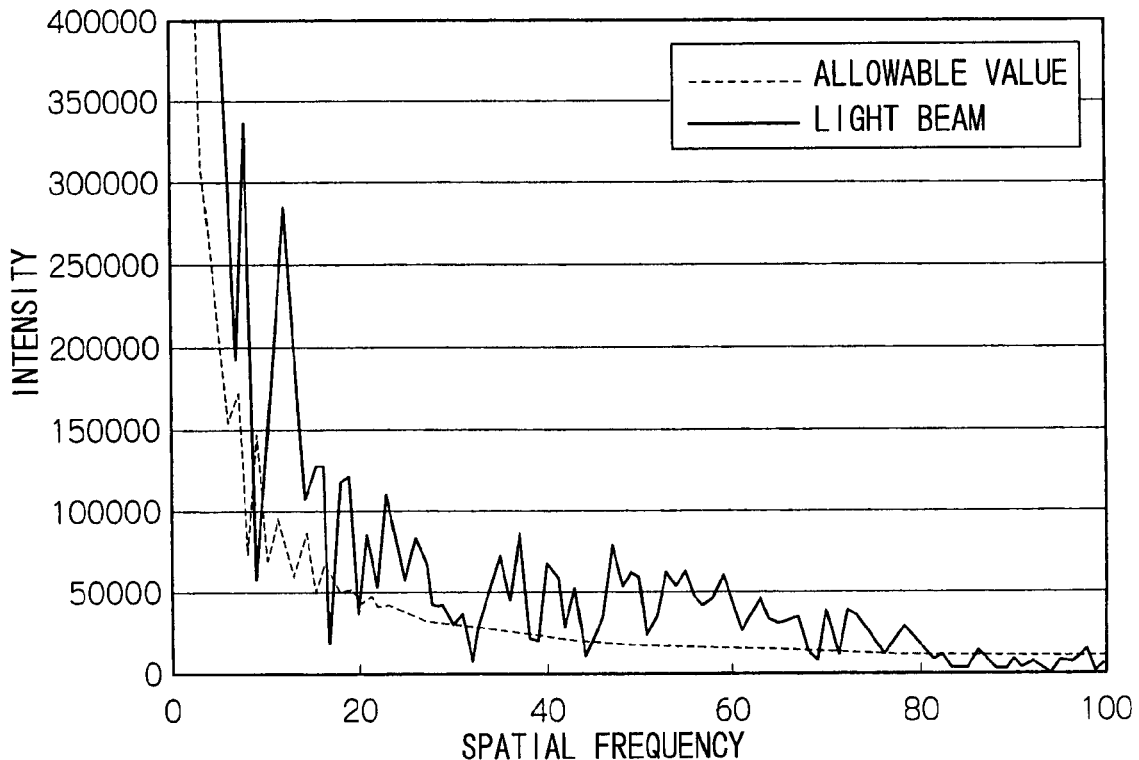
FIG. 28B is a graph presenting the comparison results of the light intensity distribution of every spatial frequencies presented in FIG. 27B and the threshold value.

FIG. 28A shows the comparison results, in which the light intensity distribution of each spatial frequency shown in FIG. 26B is compared with the threshold value predetermined for each spatial frequency. FIG. 28B shows the comparison results, in which the light intensity distribution of each spatial frequency shown in FIG. 27B is compared with the threshold value predetermined for each spatial frequency.

Next, the description is made on the procedure for determining the threshold value for each spatial frequency.

Figure 29A:
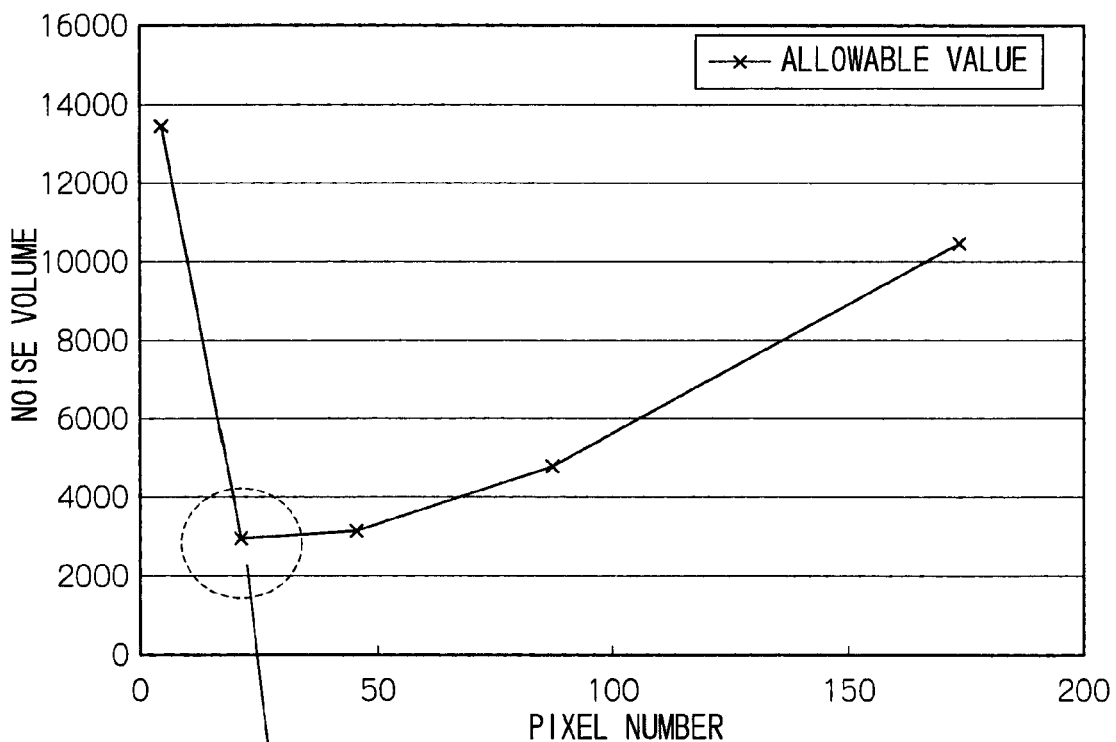
FIG. 29A is a graph presenting the threshold values of every pixel numbers at the time of averaging.
Figure 29B:
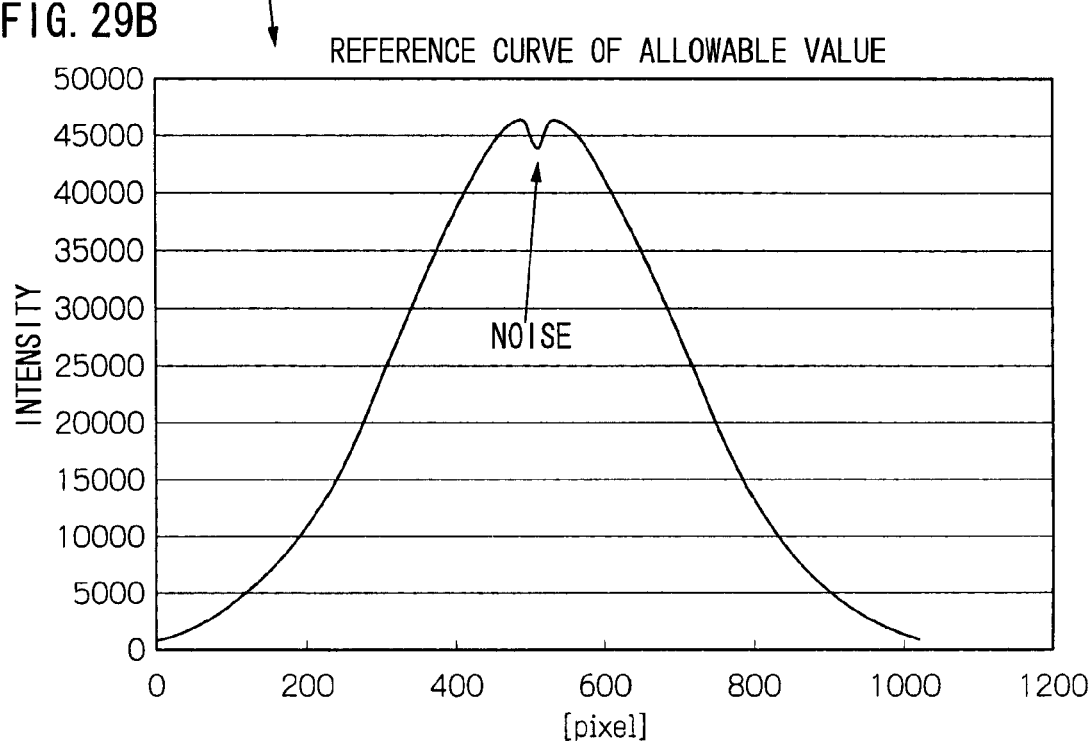
FIG. 29B is a graph presenting the light intensity distribution of a light beam, to which noises are added.
Figure 30:
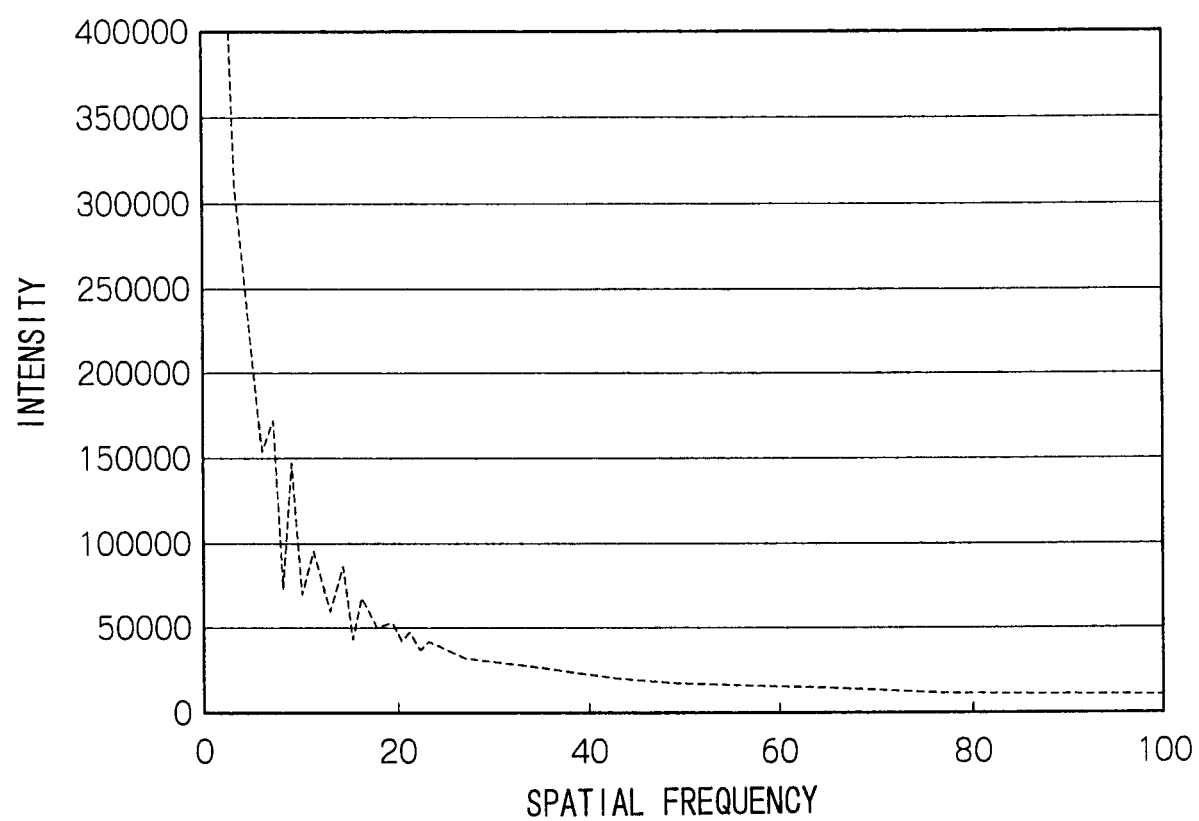
FIG. 30 is a graph presenting the threshold values of every spatial frequencies.

As shown in FIG. 29A, the errors become the largest in case the noises of the pixel number 20 (or the half-width of 10 pixels) are contained. Assuming that the light intensity distribution of the light beam is normal as shown in FIG. 29B, noises having an amplitude of 3000 are added to the position (512 pixels in this case) where the errors become the largest in that normal distribution, the light intensity distribution is subject to the fast Fourier transformation, to thereby acquire the light intensity distribution of each spatial frequency, as shown in FIG. 30.

In the biosensor 10 according to this embodiment, the light intensity distribution of each spatial frequency thus obtained is stored in advance in the detection precision evaluating portion 86.

Figure 31A:
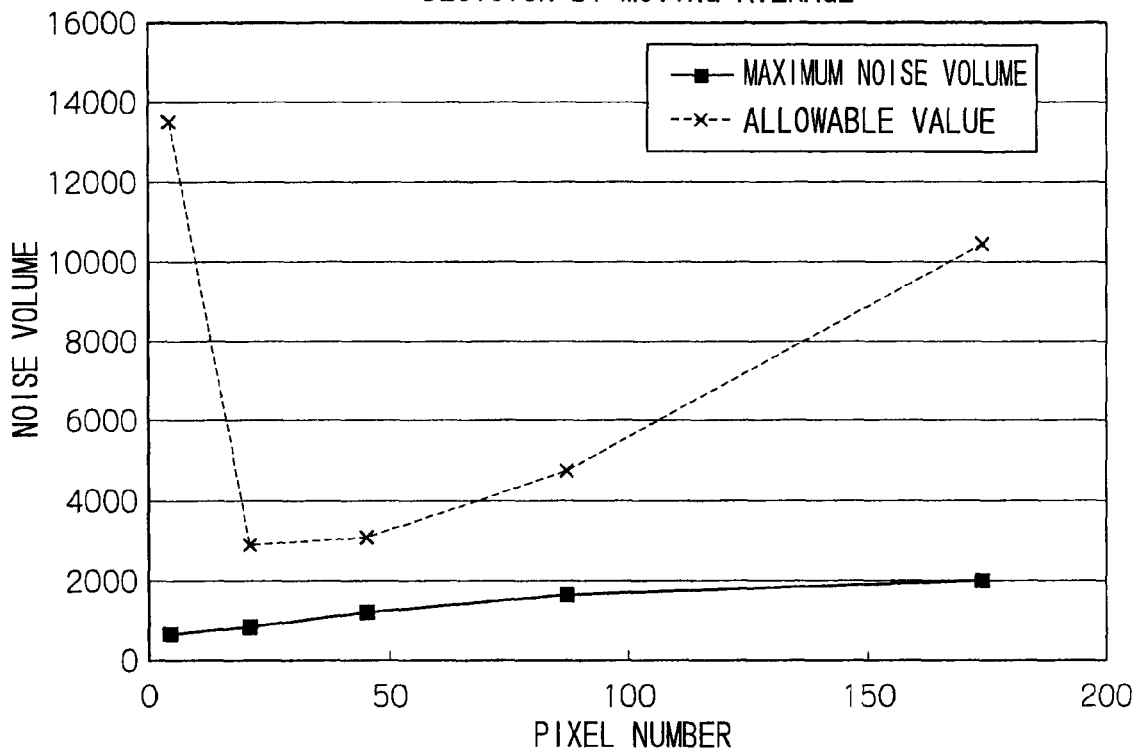
FIG. 31A is a result which is obtained by evaluating the light intensity distribution presented in FIG. 26A according to the method of the first embodiment.
Figure 31B:
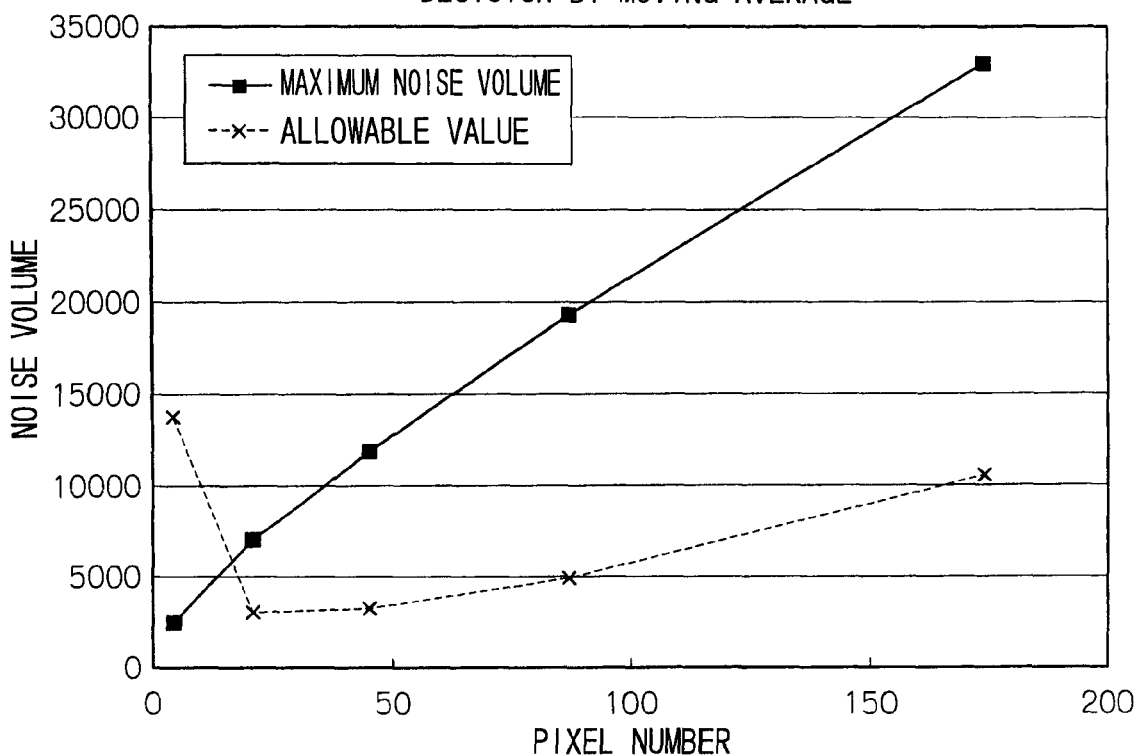
FIG. 31B is a result which is obtained by evaluating the light intensity distribution presented in FIG. 27A according to the method of the first embodiment.

Here, FIG. 31A shows the results, in which the light intensity distribution indicated by the distribution information shown in FIG. 26A is evaluated by the method according to the first embodiment, and FIG. 31B shows the results, in which the light intensity distribution indicated by the distribution information shown in FIG. 27A is evaluated by the method according to the first embodiment. Thus, both the first and second embodiments can acquire similar evaluation results.

According to this embodiment thus far described, the light intensity distribution indicated by the distribution information is subject to the Fourier transformation to thereby derive the light intensity distribution of each spatial frequency, so that only the noises of a specific spatial frequency can be precisely detected.

Third Embodiment

Here, it is expensive to manufacture the dielectric block 52 of the measurement chip 50 to be used in the biosensor 10, integrally of glass. It is, therefore, general that the dielectric block 52 is inexpensively manufactured by an injection mold using plastics or the like. As the optical material which has transparency to the light beam and which can be formed by being thermally melted and poured into a mold and then by being cooled, there may be optical glass such as BK7, or a synthetic resin such as polymethyl methacrylate, polyethylene terephthalate, polycarbonate or cycloolefin polymer, to which it should not be limited.

In case the dielectric block 52 is manufactured by the injection molding method, however, a foreign matter such as sand dust, including silicon oxide, iron oxide or alumina, or cellulose fibers coming from paper or cloths may migrate, unless the molding machine is disposed in the environment of a sufficiently clean room. Even in case the migration of the foreign matter can be prevented by disposing the molding machine in the clean room environment, the molding material is carbonized by the heat on the cylinder surface or the screw surface of the molding machine, so that the foreign matter of several 100 μm is produced and it is unable to avoid the migration of that foreign matter.

In the dielectric block 52, the noises occur in the light beam, if the foreign matter having migrated is on the optical path of the light beam. As a result, the detection precision of the biosensor 10 decreases.

Figure 32:
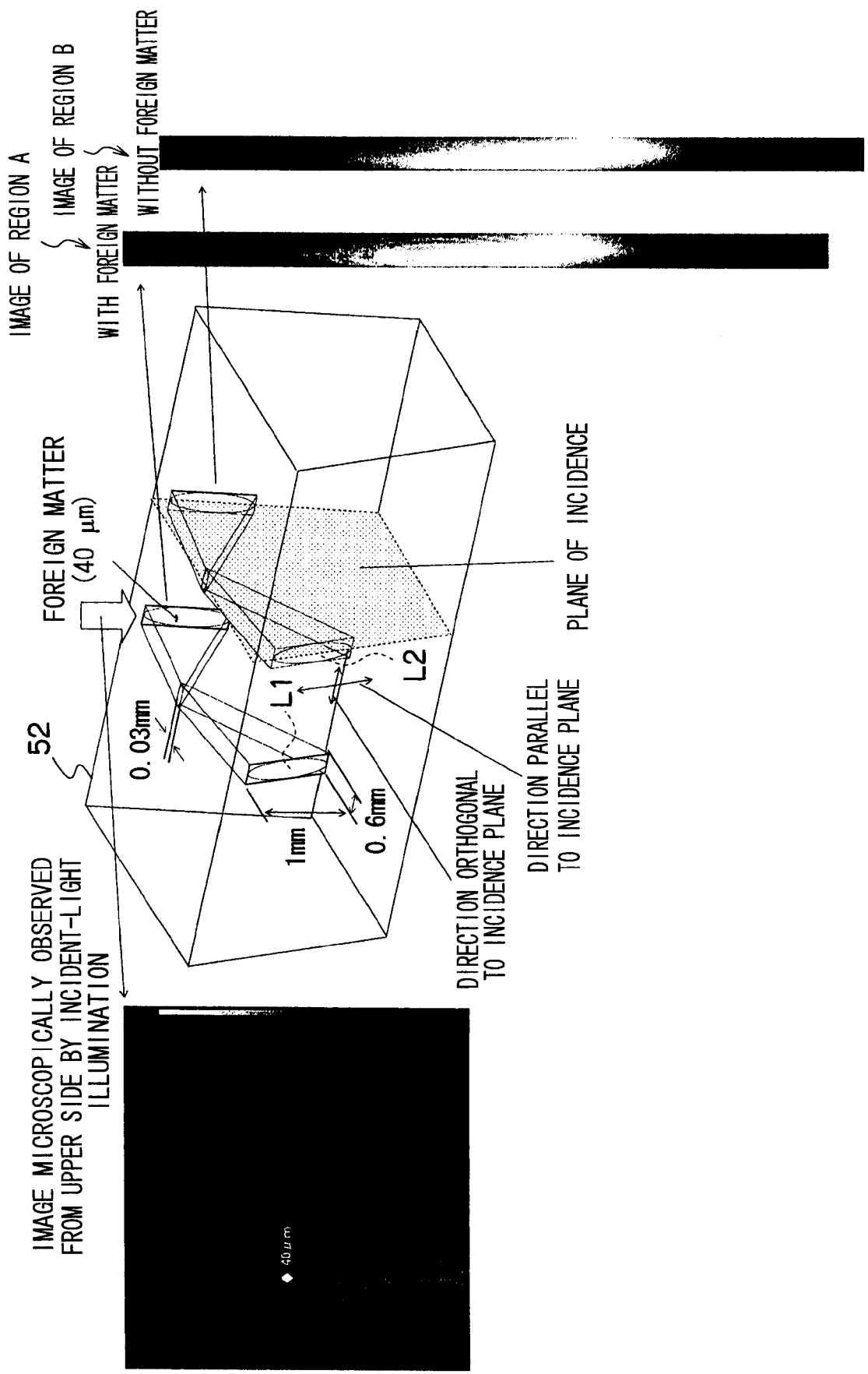
FIG. 32 is a view showing one example of the image, in which noises are generated due to a foreign matter contained in a dielectric block.

In the case of using the dielectric block 52 containing a foreign matter of a size of about 40 μm, as shown in FIG. 32, noises occur in the light beam in the dielectric block 52 and appear in the image (the image of the region A in FIG. 32) to be projected on the light-receiving surface of the CCD 36B. As a result, noises also occur in the light intensity distribution of the light beam so that the detection precision decreases.

Figure 33:
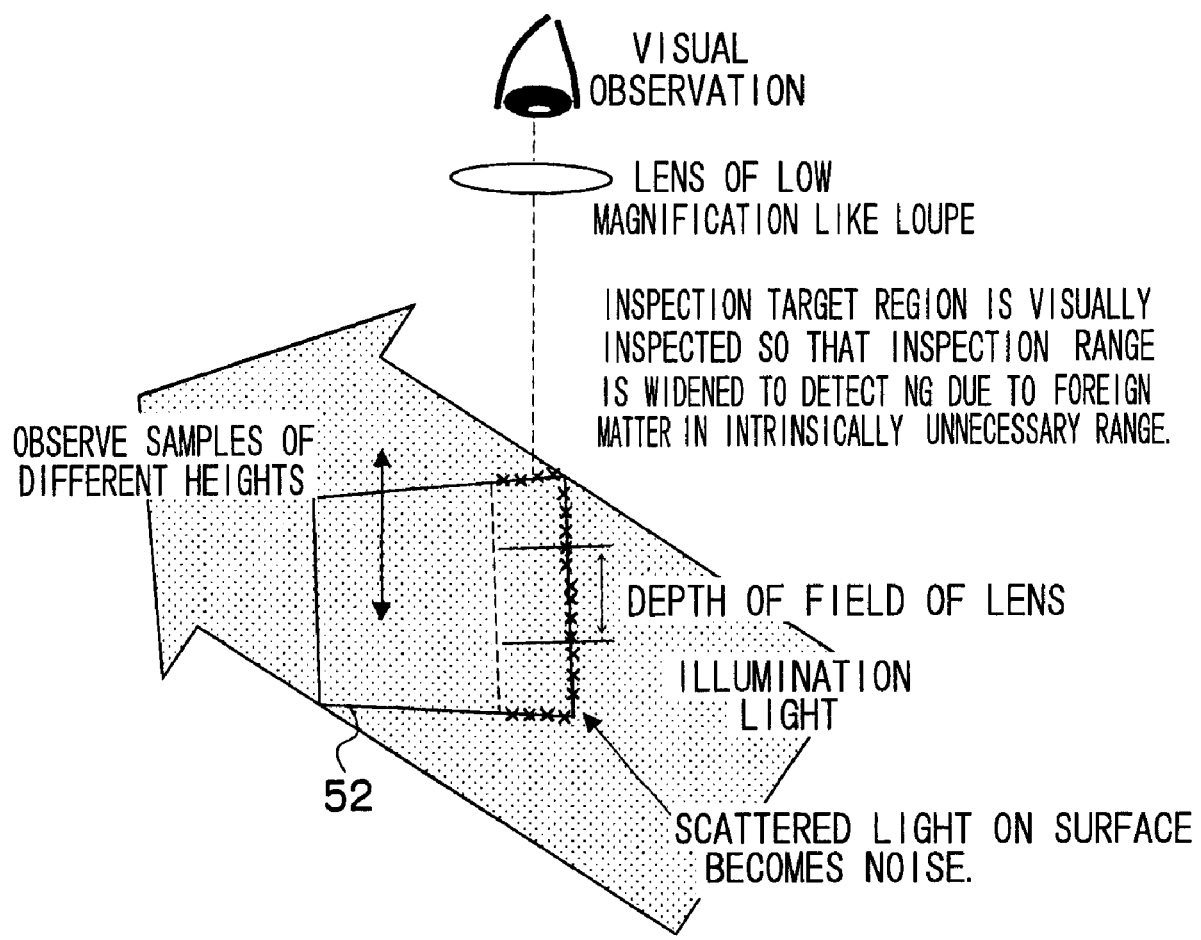
FIG. 33 is a schematic view showing one example of a conventional inspection method according to a visual inspection.
Figure 34:
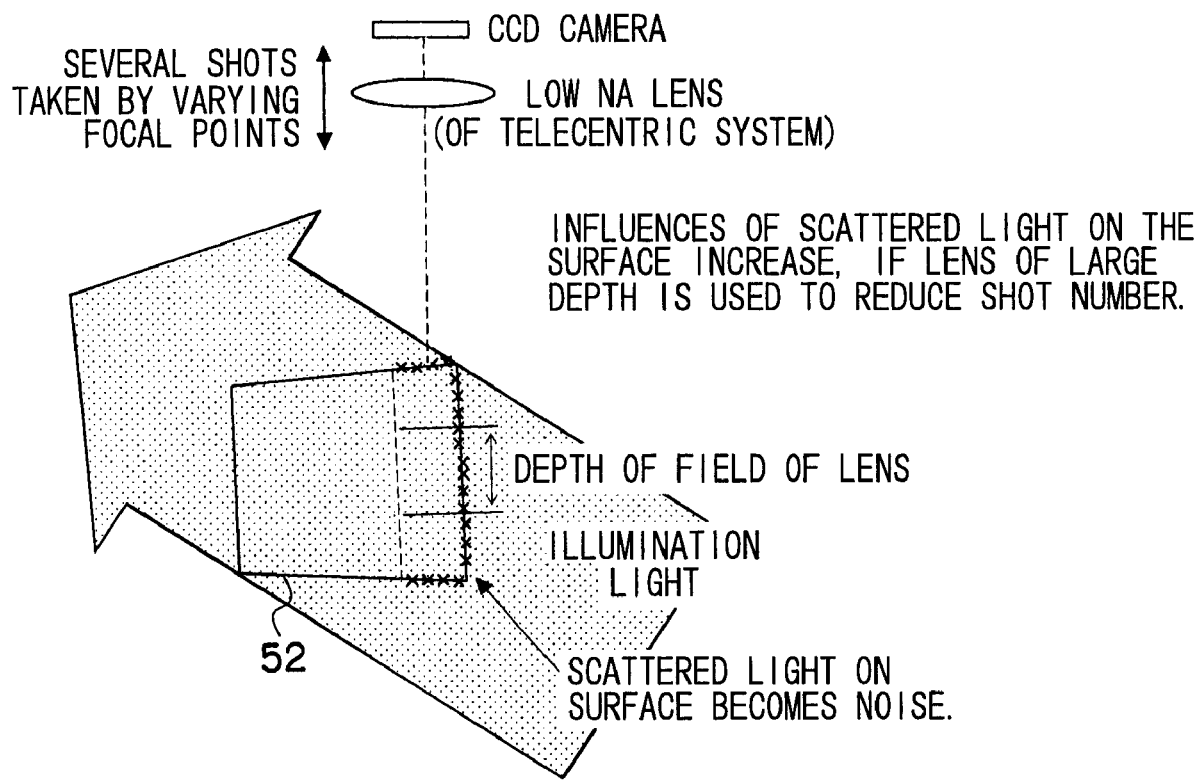
FIG. 34 is a schematic view showing one example of a conventional inspection method with a CCD camera using a low NA lens.
Figure 35:
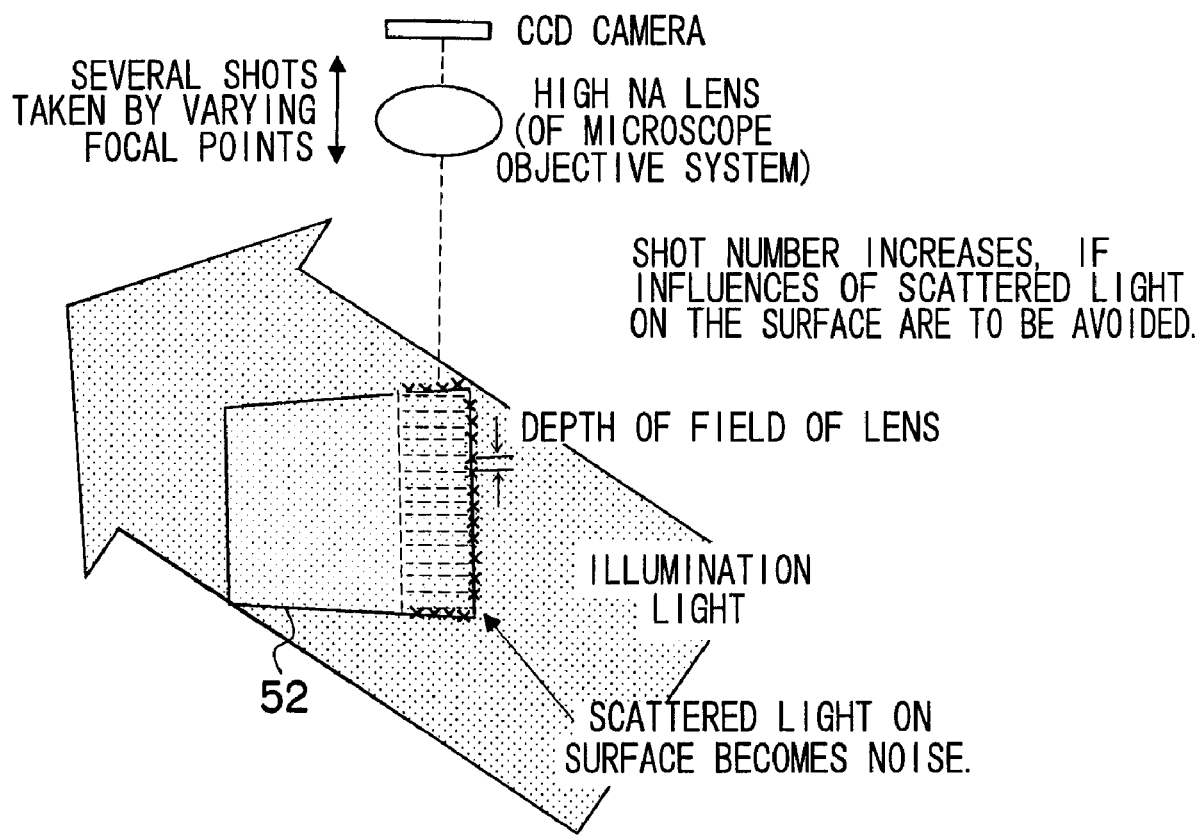
FIG. 35 is a schematic view showing one example of a conventional inspection method with a CCD camera using a high NA lens.

As the method for detecting the foreign matter having migrated in the dielectric block 52, there may be the method shown in FIG. 33 to FIG. 35. Here, the method shown in FIG. 33 to FIG. 35 is to observe the foreign matter through the lens from the upper side by illuminating the entire dielectric block 52 with the parallel or diverged dark field transmitted illumination.

For example, the method shown in FIG. 33 is a visual inspection using the human eyes. The foreign matter of several 10 μm is observed through a lens of a relatively low magnification such as a loupe. In this method, however, the target region to be inspected is roughly estimated. Therefore, a fine inspection range, such as only the range of the light beam transmission, cannot be set so that the inspection range is widened to detect even the foreign matter in the unnecessary range.

In the method shown in FIG. 34, the image is taken with the CCD camera or the like using a lens having a small NA (Numerical Aperture) and a large field depth. In this case, the range to be used for the decision can be varied in the taken image by the movement of the focal point, so that the inspection range can be more limited to the necessary range than the visual inspection. By using the lens of the large field depth, the range in the depth direction for one shot can be enlarged to perform the inspection with few shots for a short time period.

By the projections due to the dust on the surface of the dielectric block 52 or the flaws of the mold or by the depressions of the surface due to the attachments to the mold, the illumination light is scattered to become hard to discriminate from the inside foreign matter and to eliminate the internal foreign matter exclusively.

In the method shown in FIG. 35, in order to prevent the illumination light from being scattered by the projections due to the dust on the surface of the dielectric block 52 or the flaws of the mold or by the depressions of the surface due to the attachments to the mold, so that the discrimination from the inside foreign matter becomes hard, a lens having a large NA and a small field depth is used. The focal point is finely moved to take many images to thereby discriminate the foreign matter of several 10 μm. However, this method takes a long time period for inspecting one portion, through which the light beam transmit, because many images are taken by moving the focal point.

In the third embodiment, therefore, the mode of embodiment is described in case the foreign matter having migrated to the dielectric block 52 is detected on the basis of the light intensity distribution of the light beams which are incident at a plurality of angles so as to be totally reflected at the interface between the dielectric block 52 and the outside air layer and which are totally reflected at the interface.

Figure 36:
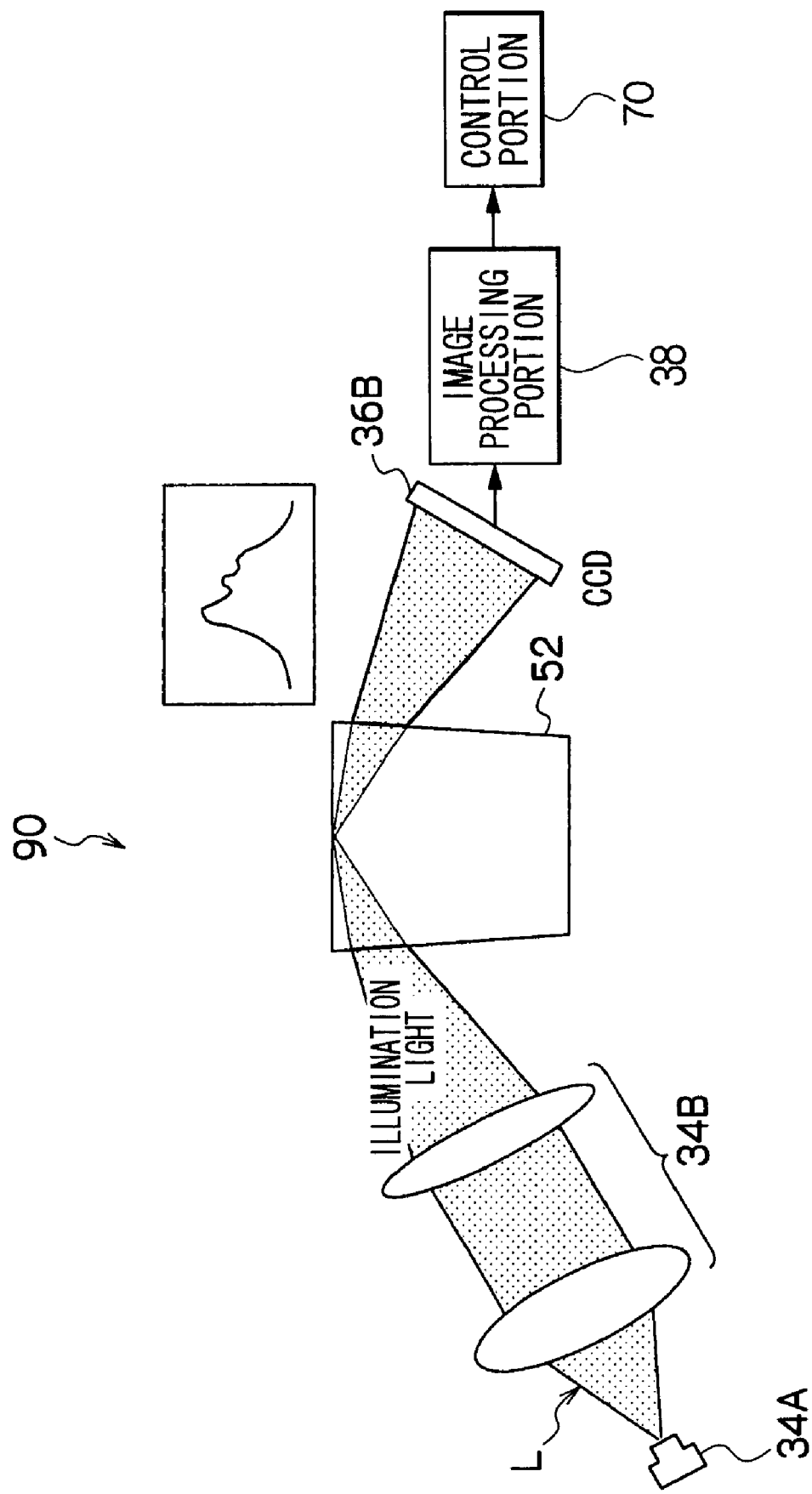
FIG. 36 is a configuration diagram showing a schematic configuration of an inspecting apparatus according to the third embodiment.

FIG. 36 shows a schematic configuration of an inspecting apparatus 90 for detecting a foreign matter according to the third embodiment. Here, the inspecting apparatus 90 has a configuration similar to that of the vicinity of the optical measurement portion, as shown in FIG. 10, of the aforementioned biosensor 10, and the same portions are omitted on their description by designating them by the same reference numerals as those of FIG. 10.

The lens unit 34B of this embodiment does not have the polarizing beam splitter. The light beam L incident from the light source 34A is one parallel, relatively thick light beam having a constant width in a Z-direction. This parallel light beam L is incident at various incidence angles larger than the total reflection angle with respect to the interface of the dielectric block 52 so as to be converged at the interface.

Figure 37:
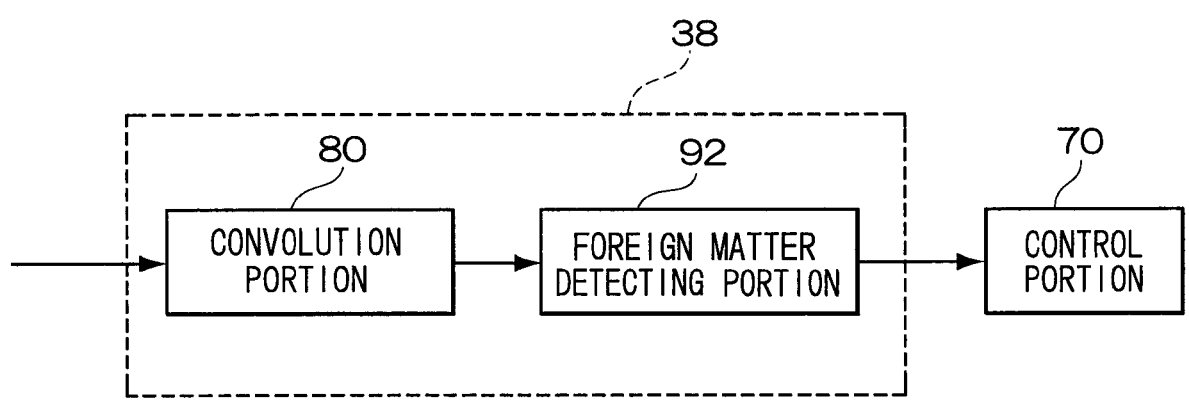
FIG. 37 is a block diagram showing a functional configuration of an image processing portion according to the third embodiment.

FIG. 37 is a block diagram showing a functional configuration of the image processing portion 38 according to this embodiment. Here, the same configuration components of FIG. 37 as those of FIG. 11 are omitted on their description by designating them by the same reference numerals as those of FIG. 11.

As shown in FIG. 37, the image processing portion 38 is constituted by: the convolution portion 80 for performing convolution of a two-dimensional image indicated by the image information, to thereby derive distribution information indicating one-dimensional light intensity distribution; and a foreign matter detecting portion 92 for detecting a foreign matter having migrated to the dielectric block 52 on the basis of the distribution information derived.

Next, the description is made on the operations of the inspecting apparatus 90 according to this embodiment.

In the inspecting apparatus 90 (refer to FIG. 36) according to this embodiment, the light-emitting portion 34 to be inspected is set at a predetermined position by the user.

In case the inspecting apparatus 90 according to this embodiment inspects the dielectric block 52 set, the light beam is emitted from the light-emitting portion 34 so that the dielectric block 52 to be inspected is irradiated with the light beam L. This light beam L is incident to the dielectric block 52, and is totally reflected at the interface between the dielectric block 52 and the outside (the air layer), so that the light beam L is emitted, while being diverged, to the outside through the prism surface of the dielectric block 52. The light beam L thus emitted to the outside is projected on the light-receiving surface of the CCD 36B so that the image information indicating the image projected on the light-receiving surface is generated and outputted to the image processing portion 38.

The convolution portion 80 (refer to FIG. 37) of the image processing portion 38 performs convolution of the image containing the image of the light beam L indicated by the input image information, and derives the distribution information indicating the one-dimensional light intensity distribution of the light beam L.

The foreign matter detecting portion 92 determines the light intensity distribution of the moving average of each predetermined width, from the light intensity distribution indicated by the derived distribution information, and determines the difference between the light intensity distribution of the moving average and the corresponding light intensity distribution indicated by the distribution information, to thereby derive the light intensity distribution of each spatial frequency. After this, the difference between the maximum and the minimum of the differences is determined. These processings are performed several times while varying the width, to thereby derive the noise volume of each spatial frequency contained in the light intensity distribution indicated by the distribution information.

Like the processing of the aforementioned detection precision evaluating portion 86 in the first embodiment, for example, the individual intensity values of the light intensity distribution indicated by the distribution information are averaged by each predetermined width to thereby determine the light intensity distribution of the moving average, and the difference is determined between the light intensity distribution of the moving average and the light intensity distribution indicated by the distribution information. These processings to determine the differential intensity distribution are performed several times while varying the predetermined width, to thereby determine the noise volume of the high-frequency component contained in the light intensity distribution indicated by the distribution information for every steps.

As a result, the high-frequency component due to the noises contained in the light intensity distribution indicated by the distribution information is extracted.

Figure 38:
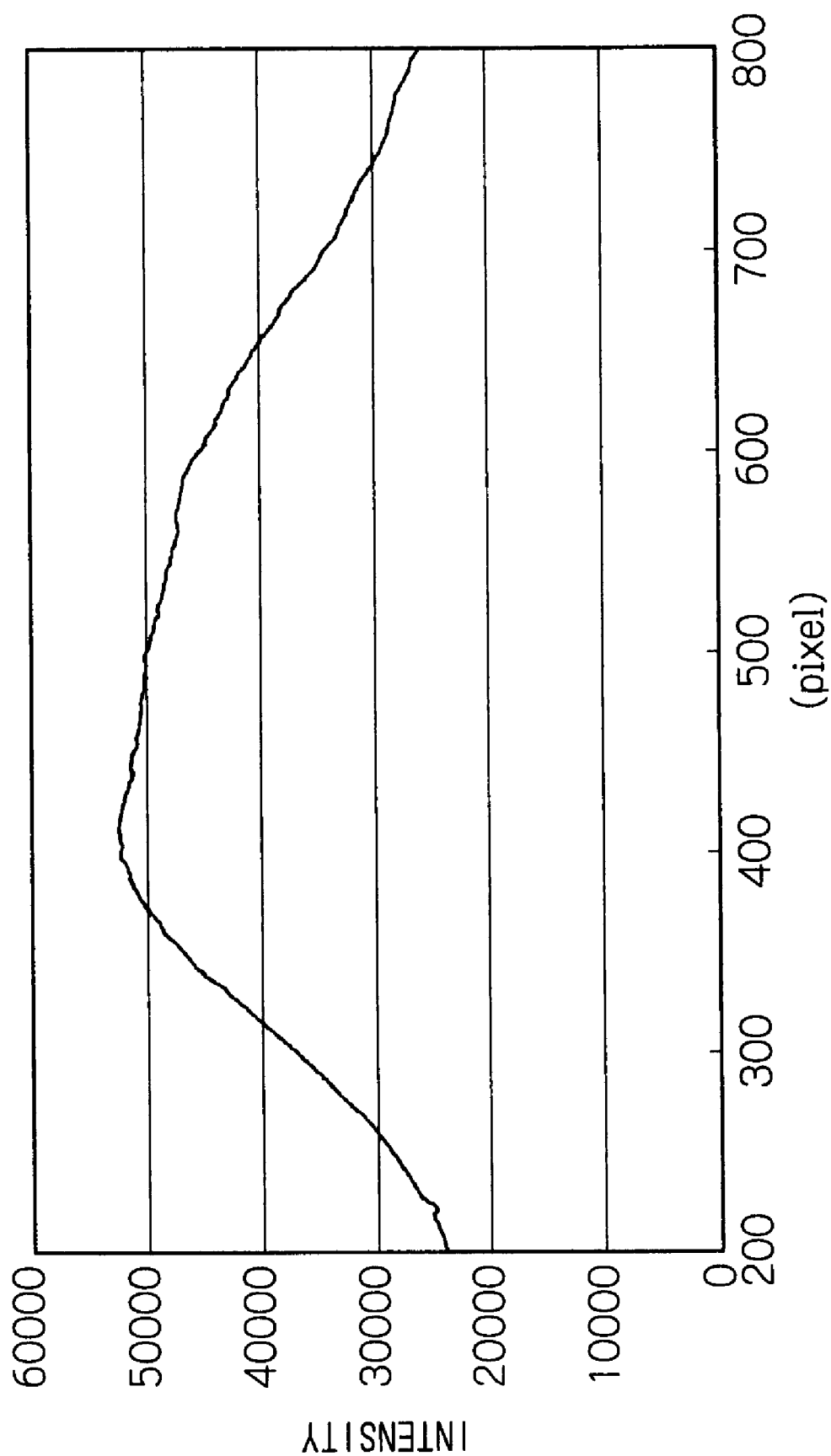
FIG. 38 is a graph presenting one example of the light intensity distribution of a light beam using a dielectric block having no migration of a foreign matter.

FIG. 38 shows one example of the light intensity distribution indicated by the distribution information which is obtained by irradiating the dielectric block 52 having no migration of the foreign matter, with the light beam L. FIG. 39A to FIG. 39D show the results, which are obtained by averaging the individual intensity values by 5 pixels, 21 pixels, 45 pixels and 87 pixels before and after the individual intensity values of the light intensity distribution shown in FIG. 38 to thereby determine the light intensity distribution of the moving average and by determining the difference between the light intensity distribution of the moving average and the light intensity distribution indicated by the distribution information to thereby determine the differential intensity distribution.

Figure 40:
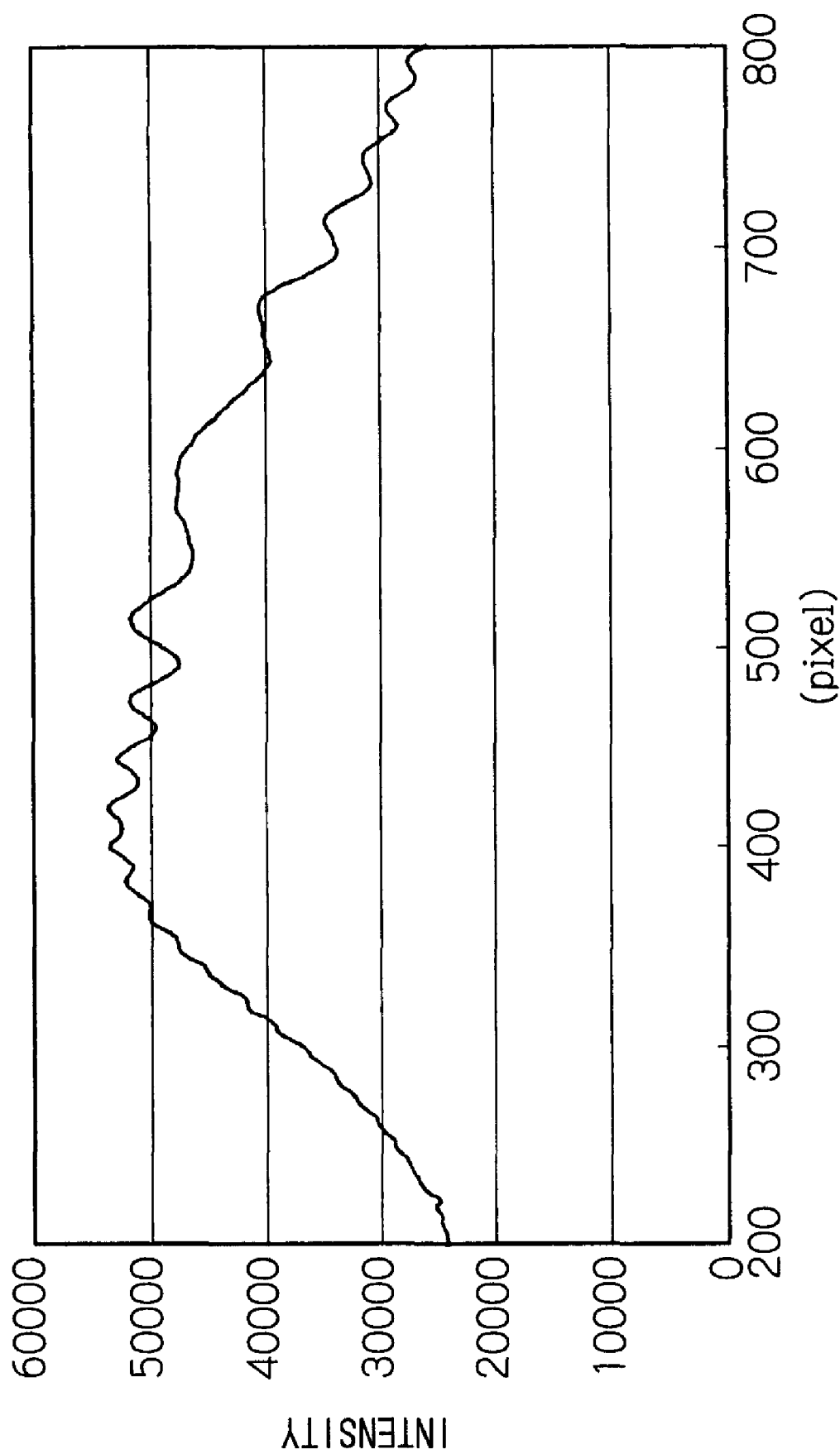
FIG. 40 is a graph presenting one example of the light intensity distribution of a light beam using a dielectric block having a migration of a foreign matter.

FIG. 40 shows one example of the light intensity distribution indicated by the distribution information which is obtained by irradiating the dielectric block 52 having a migration of the foreign matter, with the light beam L. FIG. 41A to FIG. 41D show the results, which are obtained by averaging the individual intensity values by 5 pixels, 21 pixels, 45 pixels and 87 pixels before and after the individual intensity values of the light intensity distribution shown in FIG. 40 to thereby determine the light intensity distribution of the moving average and by determining the difference between the light intensity distribution of the moving average and the light intensity distribution indicated by the distribution information to thereby determine the differential intensity distribution.

Then, the minimum MIN of each differential intensity distribution obtained is subtracted from the maximum MAX, to determine the maximum noise volume. The more the noise contained in the light beam L is increased due to the foreign matter migrating to the dielectric block 52, the larger the maximum noise volume becomes.

The foreign matter detecting portion 92 evaluates the detection precision of the dark line positions by comparing the maximum noise volume of each width with the threshold value predetermined for each width.

Figure 42:
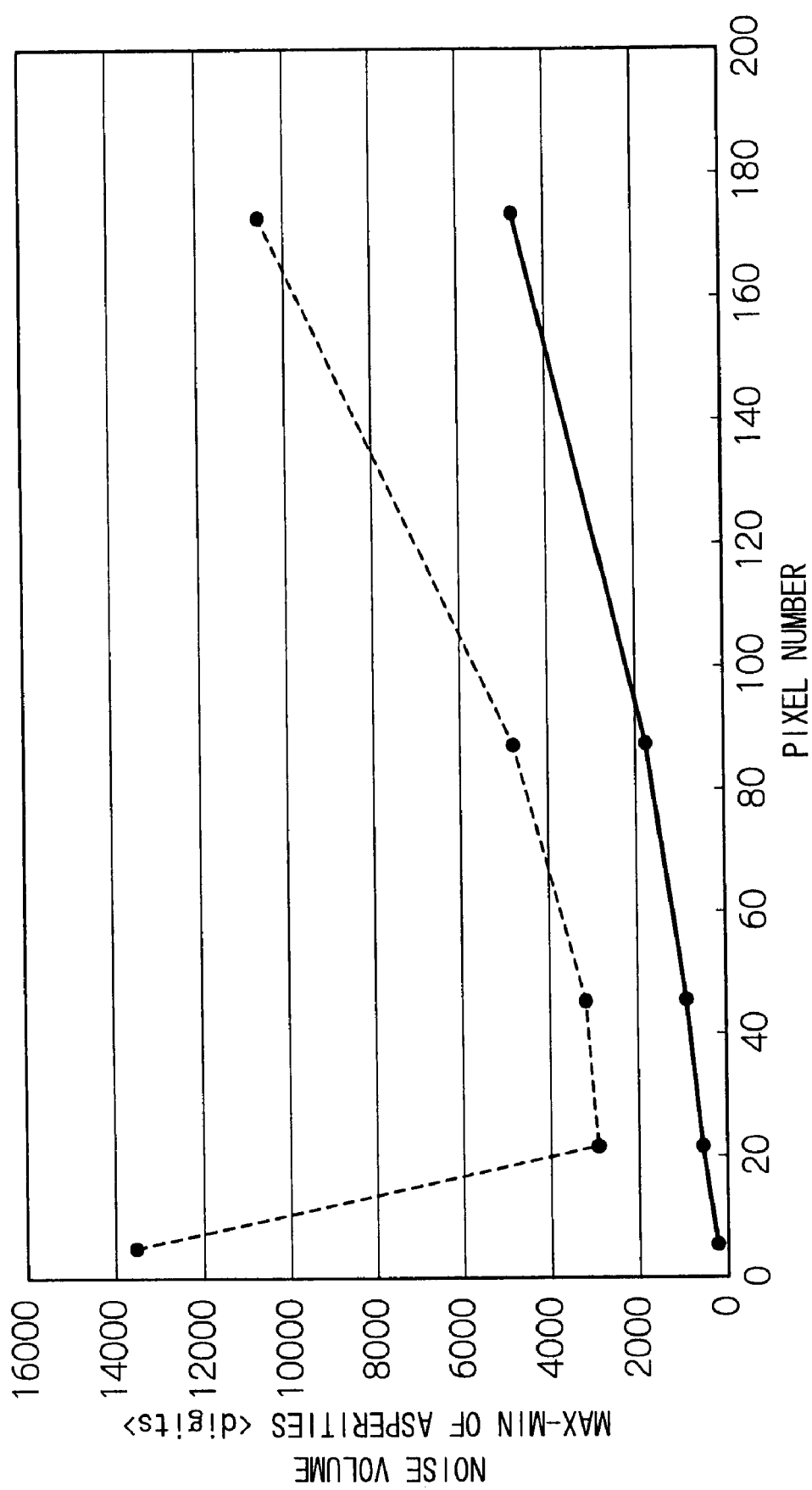
FIG. 42 is a graph presenting the results of comparisons between the maximum noise volume using a dielectric block having no migration of a foreign matter and the threshold value.
Figure 43:
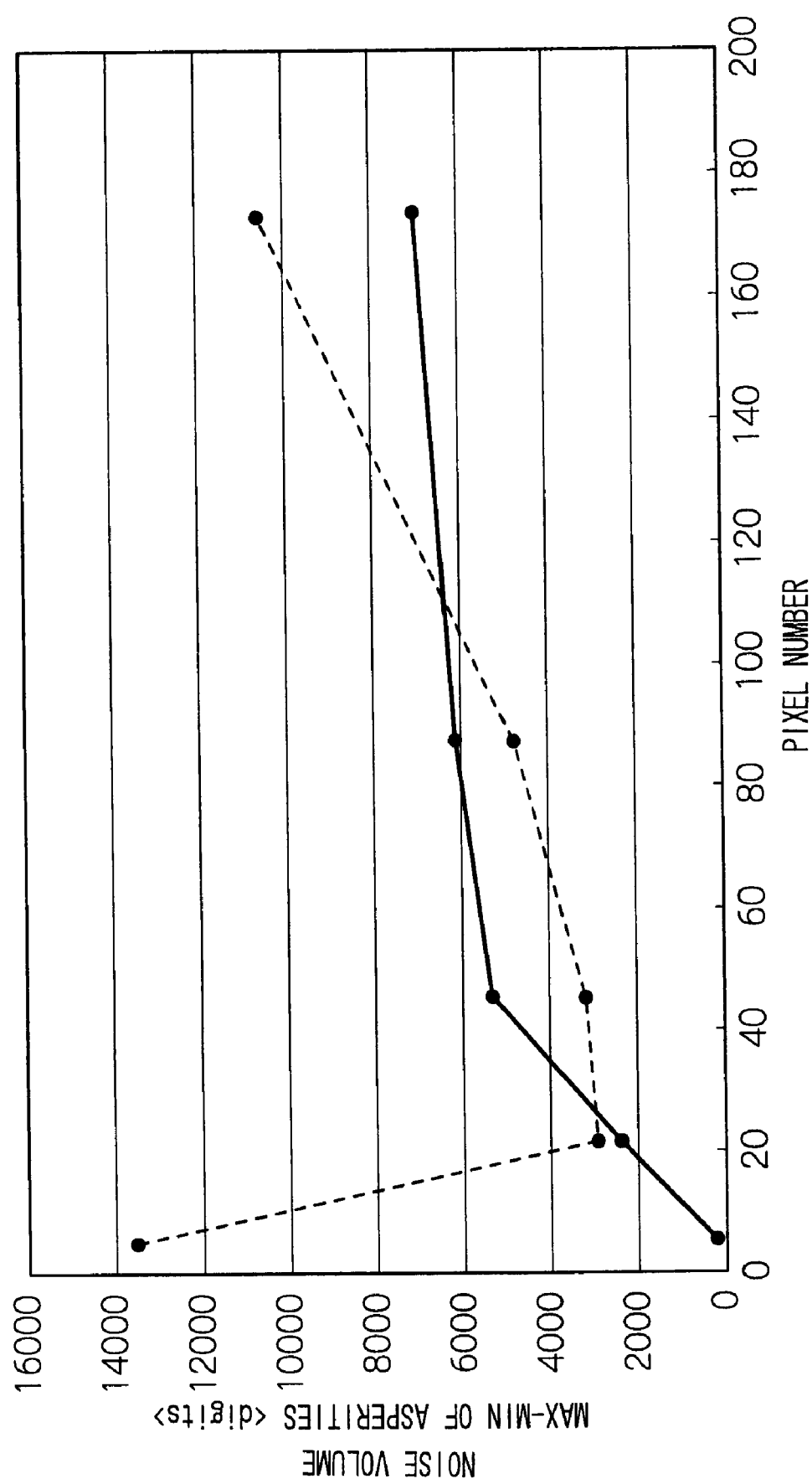
FIG. 43 is a graph presenting the results of comparisons between the maximum noise volume using a dielectric block having a migration of a foreign matter and the threshold value.

In FIG. 42, a solid-line indicates a graph plotting the maximum noise volume, which is determined by determining the aforementioned differential intensity distribution from the distribution information obtained by irradiating the dielectric block 52 having no migration of the foreign matter with the light beam L, and by subtracting the minimum MIN from the maximum MAX of the differential intensity distribution, for each pixel number contained in the width averaged when the moving average is determined. In FIG. 43, a solid-line indicates a graph plotting the maximum noise volume, which is likewise determined with respect to the dielectric block 52 having a migration of the foreign matter, for each pixel number contained in the width averaged when the moving average is determined. In each of FIG. 42 and FIG. 43, a dashed line indicates the threshold values of each width (each pixel number contained in the width).

The foreign matter detecting portion 92 decides whether or not the maximum noise volume is equal to or less than the threshold value in all the pixel numbers. In case the maximum noise volume is equal to or less than the threshold value in all the pixel numbers, the precision information indicating that no foreign matter migrates and that the detection precision of the dark line position satisfies the desired precision is outputted to the control portion 70. In case the maximum noise volume of the light intensity distribution in any distribution information is larger than the threshold value, the precision information indicating that a foreign matter migrates and the detection precision of the dark line position is lower than the desired precision is outputted to the control portion 70.

The inspecting apparatus 90 repeats the aforementioned processings with a plurality of light beams, or by moving the dielectric block 52 and the light beam L relatively to thereby perform the aforementioned decision in all the regions of the dielectric block 52, through which the light beam may transmit.

The control portion 70 passes the inspections of the dielectric block 52, if all the decisions are "without foreign matter".

Here, the following Table 1 shows one example of the inspection results according to the visual inspection method shown in FIG. 33, and the following Table 2 shows one example of the inspection result according to the inspection method using the inspecting apparatus 90.

Figure 44:
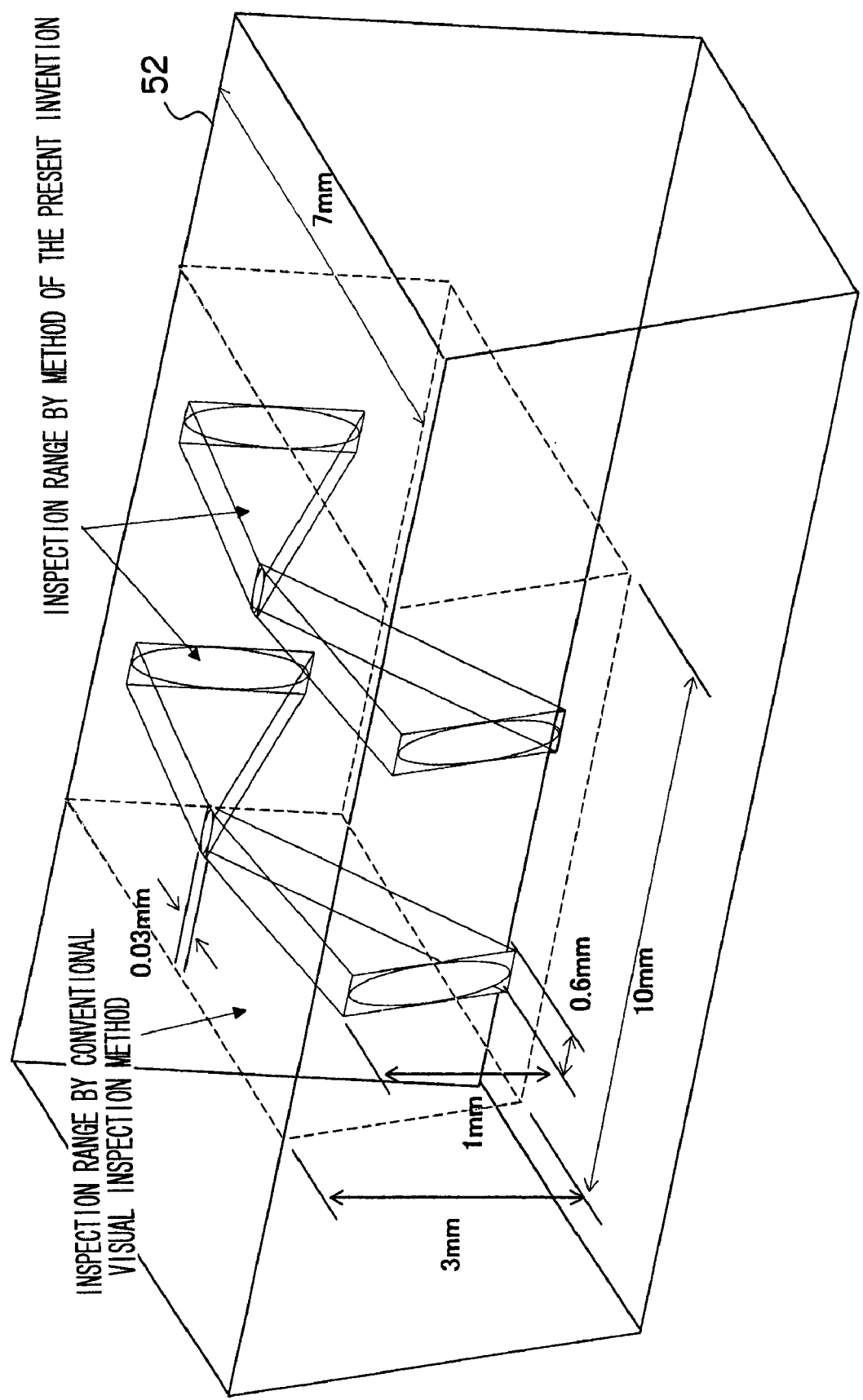
FIG. 44 is a view showing one example of the inspection ranges according to a visual inspection method and the inspection method of the third embodiment.

FIG. 44 shows one example of the inspection ranges according to the visual inspection method and the inspection method using the inspecting apparatus 90. In the conventional visual inspection, the inspections of the foreign matter are performed within the inspection ranges of $0.20\ cm^3 \times 6$ positions=$1.2\ cm^3$ for one dielectric block 52, and it is decided that a foreign matter exists if the foreign matter is larger than 50 μm. In the inspection method using the inspecting apparatus 90, the asperities are decided within the inspection range of $0.0012\ cm^3 \times 12$ positions=$0.014\ cm^3$ for one dielectric block 52.

TABLE 1

|  | Nos. of Inspection | Nos. of OK | OK Rate | NG Rate | Inspection Volume [cm³] | Foreign Matter Density [Nos./cm³] |
|---|---|---|---|---|---|---|
| Lot A | 96 | 20 | 21% | 79% | 117 | 0.6 |
| Lot B | 298 | 53 | 18% | 82% | 364 | 0.7 |
| Lot C | 272 | 80 | 29% | 71% | 332 | 0.6 |

OK: Without Foreign Matter
NG: With Foreign Matter

TABLE 2

|  | Nos. of Inspection | Nos. of OK | OK Rate | NG Rate | Inspection Volume [cm³] |
|---|---|---|---|---|---|
| Lot A | 95 | 95 | 100% | 0% | 1.3 |
| Lot B | 56 | 56 | 100% | 0% | 0.8 |
| Lot C | 120 | 119 | 99% | 1% | 1.7 |

OK: Without Foreign Matter
NG: With Foreign Matter

Thus in the inspection method using the inspecting apparatus 90, the volume of the inspection range to be inspected is suppressed to about 1/87 (≈0.014/1.2), as compared with the visual inspection method. It is, therefore, possible to prevent even the foreign matter, which is not needed for the detection precision, from being detected to decide the NG.

Figure 45A:
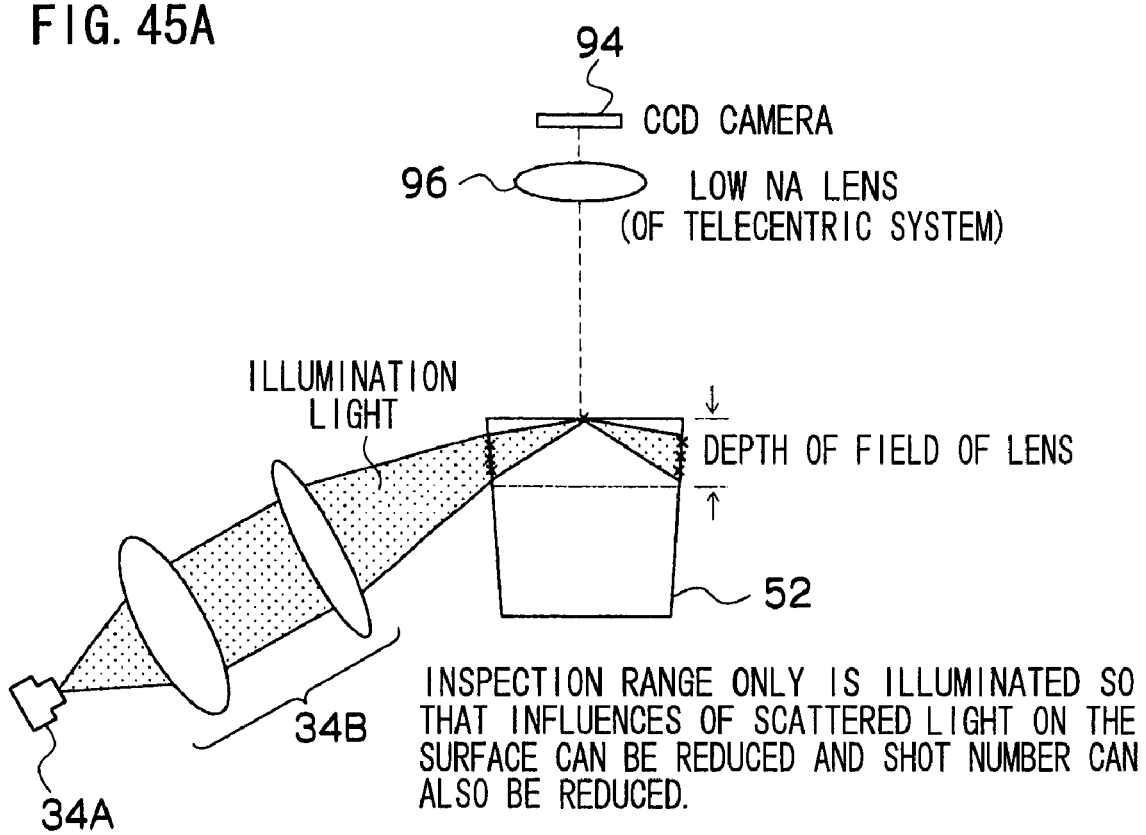
FIG. 45 is a configuration diagram showing a schematic configuration of another mode for detecting the migration of a foreign matter.

Here, the third embodiment has been described on the case, in which the inspections are performed on the basis of the light intensity distribution of the light beam L totally reflected at the interface. However, the present invention should not be limited thereto but may be modified for example, as shown in FIG. 45A, such that a CCD camera 94 is arranged above the interface, on which the light beam L is totally reflected, of the dielectric block 52. Of the scattered lights of the light beam scattered by the foreign matter, the scattered light having the angular component to be emitted upward may be imaged on the CCD camera 94 by a lens 96 of a low NA, to thereby take the image of the foreign matter of the light beam L. In this case, the angular component of the scattered light to contribute to the imaging is extremely small. It is, therefore, desired to use the cooled CCD as the detector.

Figure 45B:
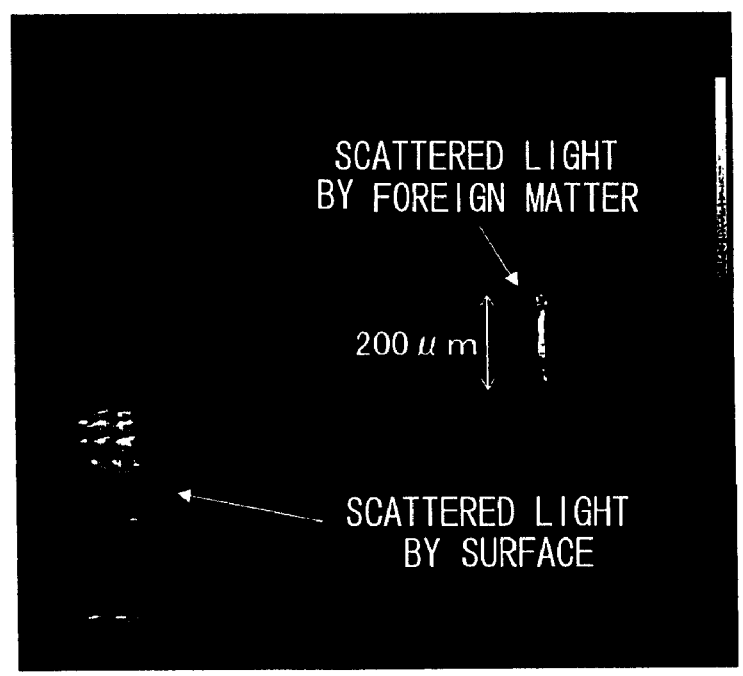

As shown in FIG. 45B, in the dielectric block 52, no light point appears in the space having no scatter due to the surface or the foreign matter, but a light point appears in case the foreign matter is contained. By thus arranging the CCD camera 94 above the interface, it is possible to take a foreign matter image of a high contrast.

In this case, the image of light and shade obtained by the CCD camera 94 is binarized with a predetermined threshold value to specify an assembly of light point pixels due to the foreign matter. The presence/absence of the influence of the foreign matter on the light beam in the inspection region can be inspected by deciding whether or not the assembly of light point pixels due to the specified foreign matter exceeds the pixel number of the assembly predetermined as an unallowable size of the foreign matter.

Moreover, the third embodiment has been described on the case, in which the noise volume of each spatial frequency is derived from the light intensity distribution to thereby detect the foreign matter. The present invention should not be limited thereto but may be modified for example, as described in the aforementioned second embodiment, such that the Fourier transformation is performed on the light intensity distribution to perform the spatial frequency resolution, so that the light intensity distribution of each spatial frequency of the light beam is derived to detect the foreign matter.

Moreover, the third embodiment has been described on the case, in which there is constituted the inspecting apparatus 90 for inspecting the foreign matter. The present invention should not be limited thereto, but may be modified for example such that the inspection of the foreign matter is performed in the biosensor 10 according to the first and second embodiments.

Moreover, the first and second embodiments have been described on the case, in which the lens unit 34B makes the two parallel light beams L1 and L2 incident at various angles to the measurement region E1 and the reference region E2 at the same time and in which the light beams L1 and L2 totally reflected at various reflection angles at the interface between the measurement region E1 and the reference region E2 are simultaneously received by the CCD 36B. However, the present invention should not be limited thereto, but may be modified for example such that the light beams are individually received by the CCD 36B.

Moreover, the individual embodiments have been described on the case, in which convolution is performed on the two-dimensional image indicated by the image information generated by the CCD 36B to acquire the distribution information indicating the one-dimensional light intensity distribution. However, the present invention should not be limited, but may be modified for example such that the relatively thin light beam is incident to the interface by varying its incidence angle, and such that the light beam having its reflection angle varied according to the variation of the incidence angle of the incident light beam is detected by the small light detector moving in synchronism with the variation of the reflection angles, to thereby acquire the distribution information indicating the light intensity distribution of the light beam.

Moreover, the individual embodiments have been described on the case, in which the P-polarized light beam is incident form the lens unit 34B to the measurement region E1 and the reference region E2. However, the present invention should not be limited thereto, but may also be modified for example such that the S-polarized light beam or the light beam which is not especially polarized but contains P-polarized component and the S-polarized component is used in case the noises contained in the light beam are detected.

In the case of detecting the noises, moreover, the refractive index may be varied by varying the concentration of the sample or buffer liquid to be supplied from the dispensing head 20 for the measurement or by supplying air, so that the dark line due to the total reflection attenuation may come outside of the light-receiving range of the light-receiving surface of the CCD 36B.

Moreover, the first and second embodiments have been described on the case, in which the dark line position is detected by subtracting the smoothed light intensity distribution from the light intensity distribution indicated by the distribution information. However, the present invention should not be limited thereto, but may be modified for example such that the reference data indicating the light intensity distribution of the light beam in the state of no total reflection attenuation is stored in advance in the dark line position detecting portion 84, so that the dark line position detecting portion 84 determines the difference between the light intensity distribution indicated by the distribution information and the light intensity distribution indicated by the stored reference data, to thereby derive the differential intensity distribution. In case the dark line position detecting portion 84 stores the reference data, the change data deriving portion may make control to update the reference data, when the detection precision evaluating portion 86 detects the decrease in the detection precision of the dark line position, with the distribution information derived at that time by the convolution portion 80.

Moreover, the first and second embodiments have described the case, in which the change data deriving portion 88 gives the information indicating the decrease in the detection precision to the detection result to thereby present the decrease in the detection precision. However, the present invention should not be limited thereto, but may be modified for example such that the change data deriving portion 88 stops the detection of the dark line position by the dark line position detecting portion 84 to thereby present the decrease in the detection precision.

Moreover, the first and second embodiments have been described on the case, in which the detection precision evaluating portion 86 performs the spatial frequency resolution on the light intensity distribution indicated by the distribution information, so that the light intensity distribution of each spatial frequency of the light beam is derived to detect the detection precision of the dark line position. However, the present invention should not be limited thereto, but may be modified for example such that the differential intensity distribution derived by the dark line position detecting portion 84 is subject to the spatial frequency resolution to derive the light intensity distribution of each spatial frequency of the light beam to thereby detect the detection precision of the dark line position. Alternatively, the difference between the light intensity distribution indicated by the distribution information and the light intensity distribution indicated by the aforementioned reference data may be determined and subject to the spatial frequency resolution to derive the light intensity distribution of each spatial frequency of the light beam to thereby detect the detection precision of the dark line position.

As another biosensor using total reflection attenuation, a leaky mode detector can be cited. The leaky mode sensor is constituted by a dielectric member and a thin film constituted by a clad layer and an optical waveguide layer sequentially stacked on the dielectric member. One surface of the thin film serves as a sensor surface, and the other surface serves as a light incident surface. When light is incident to the light incident surface to satisfy total reflection conditions, a part of the light passes through the clad layer and is received by the optical waveguide layer. When a waveguide mode is excited on the optical waveguide layer, reflected light on the light incident surface is largely attenuated. An incidence angle at which the waveguide mode is excited changes depending on a refractive index of a medium on the sensor surface like a surface plasmon resonance angle. The attenuation of the reflected light is detected to make it possible to measure reaction on the sensor surface.

The present invention has an object to provide a detection apparatus and a detection method, which can detect the decrease in a detection precision of a dark line position, and an optically transparent member which can suppress the decrease in the detection precision of the dark line position.

In order to achieve the aforementioned object, a first aspect of the present invention provides a detection apparatus comprising: an acquisition unit that acquires distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member; a derivation unit that performs a spatial frequency resolution on the light intensity distribution indicated by the distribution information acquired by the acquisition unit, to thereby derive the light intensity distribution of each spatial frequency of the light beam; and a detection unit that compares the light intensity distribution derived by the derivation unit, with a threshold value predetermined for each spatial frequency, to thereby detect a detection precision of a dark line position.

According to the above-described aspect, the acquisition unit acquires distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member. The derivation unit performs a spatial frequency resolution on the light intensity distribution indicated by the distribution information acquired by the acquisition unit, to thereby derive the light intensity distribution of each spatial frequency of the light beam. The detection unit compares the light intensity distribution derived by the derivation unit, with a threshold value predetermined for each spatial frequency, to thereby detect a detection precision of a dark line position. Here, the aforementioned interface is the surface, on which the optically transparent member contacts with another substance or an air layer.

According to the above-described aspect, the distribution information indicating the light intensity distribution of the light beam, which is incident at a plurality of angles to the optically transparent member so as to be totally reflected and which is totally reflected at the interface, is acquired. The spatial frequency resolution is performed on the light intensity distribution indicated by the acquired distribution information, to thereby derive the light intensity distribution of each spatial frequency of the light beam. The derived light intensity distribution is compared with the threshold value predetermined for each spatial frequency, to thereby detect the precision. As a result, it is possible to detect the decrease in the detection precision of the dark line position.

In the above-described aspect, the derivation unit may derive the light intensity distribution of each spatial frequency by determining the light intensity distribution of a moving average of each predetermined width from the light intensity distribution indicated by the distribution information and by determining a difference between the light intensity distribution of the moving average and the corresponding light intensity distribution indicated by the distribution information, and determine a difference between the maximum and the minimum of the difference, which processing is performed a plurality of times while varying the width, to thereby derive a noise volume of each spatial frequency contained in the light intensity distribution indicated by the distribution information; and the detection unit may compare each noise volume derived by the derivation unit with a threshold value that is predetermined for each width when the noise volume is derived, to thereby detect the detection precision of the dark line position.

In the above-described aspect, the derivation unit may derive the light intensity distribution of each spatial frequency of the light beam by performing a Fourier transformation on the light intensity distribution indicated by the distribution information.

In the above-described aspect, the optically transparent member may have a thin film layer formed at a part of the optically transparent member, and a sample may be contacted on the thin film layer; the acquisition unit may acquire distribution information indicating a light intensity distribution of a light beam which is totally reflected at an interface between the optically transparent member and the thin film layer, the light beam being incident at a plurality of angles to the optically transparent member so as to be totally reflected at the interface between the optically transparent member and the thin film layer; and the detection unit may compare the light intensity distribution derived by the derivation unit, with a threshold value predetermined for each spatial frequency, to thereby detect a detection precision of a dark line position.

In the above-described aspect, the light beam may be a P-polarized light beam; and the sample may be provided with a refractive index such that a dark line due to a total reflection attenuation is outside of the range of the light intensity distribution acquired by the acquisition unit, in the light intensity distribution of the P-polarized light beam totally reflected at the interface.

In the above-described aspect, the detection apparatus may further comprise a dark line position detection unit that detects the position of a dark line due to a total reflection attenuation, on the basis of the light intensity distribution indicated by the distribution information acquired by the acquisition unit; and a presentation unit that either stops the detection of the position of the dark line by the dark line position detection unit or adds information indicating a decrease in the detection precision to a detection result by the dark line position detection unit, when the light intensity distribution of each spatial frequency of the light beam derived by the derivation unit has a value larger than the threshold value predetermined for each spatial frequency, to thereby present the decrease in the detection precision, wherein the light beam is a P-polarized light beam.

In the above-described aspect, the detection apparatus may further comprise a dark line position detection unit that detects the position of a dark line due to a total reflection attenuation, on the basis of the light intensity distribution indicated by the distribution information acquired by the acquisition unit; and a presentation unit that either stops the detection of the position of the dark line by the dark line position detection unit or adds information indicating a decrease in the detection precision to a detection result by the dark line position detection unit, when the light intensity distribution of each spatial frequency of the light beam derived by the derivation unit has a value larger than the threshold value predetermined for each spatial frequency, to thereby present the decrease in the detection precision, wherein the light beam is a P-polarized light beam.

In the above-described aspect, the detection apparatus may further comprise an updating unit that updates the reference data, when the detection unit detects a decrease in the detection precision of the dark line position, with the distribution information acquired by the acquisition unit at the time of the detection of the decrease in the detection precision of the dark line position.

In the above-described aspect, the detection unit may compare the light intensity distribution derived by the derivation unit, with a threshold value predetermined for each spatial frequency, to thereby detect a foreign matter contained in the optically transparent member.

In the above-described aspect, the detection unit may detect the foreign matter contained in the optically transparent member on the basis of scattered light having an angular component emitted upward, from among the scattered light from the light beam scattered by the foreign matter contained in the optically transparent member.

In the above-described aspect, the detection unit may derive the light intensity distribution of each spatial frequency by performing a Fourier transformation on the light intensity distribution derived by the derivation unit, to thereby detect a foreign matter contained in the optically transparent member.

A second aspect of the present invention provides a detection method comprising: acquiring distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member; performing a spatial frequency resolution on the light intensity distribution indicated by the distribution information acquired, to thereby derive the light intensity distribution of each spatial frequency of the light beam; and comparing the light intensity distribution derived, with a threshold value predetermined for each spatial frequency, to thereby detect a detection precision of a dark line position.

According to the above-described aspect, the operations are similar to those of the present invention of the first embodiment so that the decrease in the detection precision of the dark line position can be detected as in the present invention of the first embodiment.

A third aspect of the present invention provides an optically transparent member having transparency to a light beam, wherein: distribution information indicating a light intensity distribution of the light beam which is totally reflected at an interface, and which is incident at a plurality of angles so as to be totally reflected at the interface, is acquired; a spatial frequency resolution is performed on the light intensity distribution indicated by the distribution information so that the light intensity distribution of each spatial frequency of the light beam is derived; and the light intensity distribution is compared with a threshold value predetermined for each spatial frequency so that a detection precision of a dark line position is detected.

According to the above-described aspect, it is possible to detect whether or not the foreign matter is contained in the optically transparent member. As a result, the manufacturing precision of the optically transparent member can be detected so that the decrease in the detection precision of the dark line position can be suppressed in case the optically transparent member is used for detecting the dark line position.

Thus, according to the detection apparatus and the detection method of an aspect of the present invention, it is possible to obtain the following effect. The distribution information indicating the light intensity distribution of the light beam, which is incident at a plurality of angles to the optically transparent member so as to be totally reflected and which is totally reflected at the interface, is acquired. The spatial frequency resolution is performed on the light intensity distribution indicated by the acquired distribution information, to thereby derive the light intensity distribution of each spatial frequency of the light beam. The derived light intensity distribution is compared with the threshold value predetermined for each spatial frequency, to thereby detect the detection precision of the dark line position. As a result, it is possible to detect the decrease in the detection precision of the dark line position.

According to the optically transparent member of an aspect of the present invention, it is possible to obtain the following effect. The decrease in the detection precision of the dark line position can be suppressed in case the optically transparent member is used for detecting the dark line position.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The exemplary embodiments were chosen and described in order to best explain the principles of the invention and its applications, thereby enabling others skilled in the art to understand the invention for various embodiments and with the various modifications as are suited for the particular use contemplated. It is intended that the scope of the invention be defined by the following claims and their equivalents.

What is claimed is:

1. A detection apparatus comprising:
   an acquisition unit that acquires distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member;
   a derivation unit that performs a spatial frequency resolution on the light intensity distribution indicated by the distribution information acquired by the acquisition unit, to thereby derive the light intensity distribution of each spatial frequency of the light beam; and
   a detection unit that compares the light intensity distribution derived by the derivation unit, with a threshold value predetermined for each spatial frequency, to thereby detect a detection precision of a dark line position, wherein:
   the derivation unit derives the light intensity distribution of each spatial frequency by determining the light intensity distribution of a moving average of each predetermined width from the light intensity distribution indicated by the distribution information and by determining a difference between the light intensity distribution of the moving average and the corresponding light intensity distribution indicated by the distribution information, and determines a difference between the maximum and the minimum of the difference, which processing is performed a plurality of times while varying the width, to thereby derive a noise volume of each spatial frequency contained in the light intensity distribution indicated by the distribution information; and
   the detection unit compares each noise volume derived by the derivation unit with a threshold value that is predetermined for each width when the noise volume is derived, to thereby detect the detection precision of the dark line position.

2. The detection apparatus according to claim 1, wherein:
   the derivation unit derives the light intensity distribution of each spatial frequency of the light beam by performing a Fourier transformation on the light intensity distribution indicated by the distribution information.

3. The detection apparatus according to claim 1, wherein:
   the optically transparent member has a thin film layer formed at a part of the optically transparent member, and a sample is contacted on the thin film layer;
   the acquisition unit acquires distribution information indicating a light intensity distribution of a light beam which is totally reflected at an interface between the optically transparent member and the thin film layer, the light beam being incident at a plurality of angles to the optically transparent member so as to be totally reflected at the interface between the optically transparent member and the thin film layer; and
   the detection unit compares the light intensity distribution derived by the derivation unit, with a threshold value predetermined for each spatial frequency, to thereby detect a detection precision of a dark line position.

4. The detection apparatus according to claim 2, wherein:
   the optically transparent member has a thin film layer formed at a part of the optically transparent member, and a sample is contacted on the thin film layer;
   the acquisition unit acquires distribution information indicating a light intensity distribution of a light beam which is totally reflected at an interface between the optically transparent member and the thin film layer, the light beam being incident at a plurality of angles to the optically transparent member so as to be totally reflected at the interface between the optically transparent member and the thin film layer; and
   the detection unit compares the light intensity distribution derived by the derivation unit, with a threshold value predetermined for each spatial frequency, to thereby detect a detection precision of a dark line position.

5. The detection apparatus according to claim 3, wherein:
   the light beam is a P-polarized light beam; and
   the sample is provided with a refractive index such that a dark line due to a total reflection attenuation is outside of the range of the light intensity distribution acquired by the acquisition unit, in the light intensity distribution of the P-polarized light beam totally reflected at the interface.

6. A detection apparatus comprising:
an acquisition unit that acquires distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member;
a derivation unit that performs a spatial frequency resolution on the light intensity distribution indicated by the distribution information acquired by the acquisition unit, to thereby derive the light intensity distribution of each spatial frequency of the light beam; and
a detection unit that compares the light intensity distribution derived by the derivation unit, with a threshold value predetermined for each spatial frequency, to thereby detect a detection precision of a dark line position, wherein:
the optically transparent member has a thin film layer formed at a part of the optically transparent member, and a sample is contacted on the thin film layer;
the acquisition unit acquires distribution information indicating a light intensity distribution of a light beam which is totally reflected at an interface between the optically transparent member and the thin film layer, the light beam being incident at a plurality of angles to the optically transparent member so as to be totally reflected at the interface between the optically transparent member and the thin film layer; and
the detection unit compares the light intensity distribution derived by the derivation unit, with a threshold value predetermined for each spatial frequency, to thereby detect a detection precision of a dark line position;
a dark line position detection unit that detects the position of a dark line due to a total reflection attenuation, on the basis of the light intensity distribution indicated by the distribution information acquired by the acquisition unit; and
a presentation unit that either stops the detection of the position of the dark line by the dark line position detection unit or adds information indicating a decrease in the detection precision to a detection result by the dark line position detection unit, when the light intensity distribution of each spatial frequency of the light beam derived by the derivation unit has a value larger than the threshold value predetermined for each spatial frequency, to thereby present the decrease in the detection precision, wherein the light beam is a P-polarized light beam.

7. The detection apparatus according to claim 3, further comprising:
a storage unit that stores in advance reference data indicating the light intensity distribution of the light beam in a state in which no total reflection attenuation occurs,
wherein the derivation unit performs the spatial frequency resolution on a light intensity distribution which is determined as the difference between the light intensity distribution indicated by the distribution information acquired by the acquisition unit and the light intensity distribution indicated by the reference data stored in the storage unit, to thereby derive the light intensity distribution of each spatial frequency.

8. A detection apparatus comprising:
an acquisition unit that acquires distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member;
a derivation unit that performs a spatial frequency resolution on the light intensity distribution indicated by the distribution information acquired by the acquisition unit, to thereby derive the light intensity distribution of each spatial frequency of the light beam; and
a detection unit that compares the light intensity distribution derived by the derivation unit, with a threshold value predetermined for each spatial frequency, to thereby detect a detection precision of a dark line position, wherein:
the optically transparent member has a thin film layer formed at a part of the optically transparent member, and a sample is contacted on the thin film layer;
the acquisition unit acquires distribution information indicating a light intensity distribution of a light beam which is totally reflected at an interface between the optically transparent member and the thin film layer, the light beam being incident at a plurality of angles to the optically transparent member so as to be totally reflected at the interface between the optically transparent member and the thin film layer;
the detection unit compares the light intensity distribution derived by the derivation unit, with a threshold value predetermined for each spatial frequency, to thereby detect a detection precision of a dark line position,
an updating unit that updates the reference data, when the detection unit detects a decrease in the detection precision of the dark line position, with the distribution information acquired by the acquisition unit at the time of the detection of the decrease in the detection precision of the dark line position, and
a storage unit that stores in advance reference data indicating the light intensity distribution of the light beam in a state in which no total reflection attenuation occurs,
wherein the derivation unit performs the spatial frequency resolution on a light intensity distribution which is determined as the difference between the light intensity distribution indicated by the distribution information acquired by the acquisition unit and the light intensity distribution indicated by the reference data stored in the storage unit, to thereby derive the light intensity distribution of each spatial frequency.

9. A detection apparatus comprising:
an acquisition unit that acquires distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member;
a derivation unit that performs a spatial frequency resolution on the light intensity distribution indicated by the distribution information acquired by the acquisition unit, to thereby derive the light intensity distribution of each spatial frequency of the light beam; and
a detection unit that compares the light intensity distribution derived by the derivation unit, with a threshold value predetermined for each spatial frequency, to thereby detect a detection precision of a dark line position,
the detection unit compares the light intensity distribution derived by the derivation unit, with a threshold value predetermined for each spatial frequency, to thereby detect a foreign matter contained in the optically transparent member.

10. The detection apparatus according to claim 2, wherein:
the detection unit compares the light intensity distribution derived by the derivation unit, with a threshold value predetermined for each spatial frequency, to thereby detect a foreign matter contained in the optically transparent member.

11. The detection apparatus according to claim 9, wherein:
the detection unit detects the foreign matter contained in the optically transparent member on the basis of scattered light having an angular component emitted upward, from among the scattered light from the light beam scattered by the foreign matter contained in the optically transparent member.

12. The detection apparatus according to claim 1, wherein:
the detection unit derives the light intensity distribution of each spatial frequency by performing a Fourier transformation on the light intensity distribution derived by the derivation unit, to thereby detect a foreign matter contained in the optically transparent member.

13. A detection method comprising:
acquiring distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member;

performing a spatial frequency resolution on the light intensity distribution indicated by the distribution information acquired, to thereby derive the light intensity distribution of each spatial frequency of the light beam by determining the light intensity distribution of a moving average of each predetermined width from the light intensity distribution indicated by the distribution information and by determining a difference between the light intensity distribution of the moving average and the corresponding light intensity distribution indicated by the distribution information, and determines a difference between the maximum and the minimum of the difference, which processing is performed a plurality of times while varying the width, to thereby derive a noise volume of each spatial frequency contained in the light intensity distribution indicated by the distribution information; and comparing the light intensity distribution derived, with a threshold value predetermined for each spatial frequency, to thereby detect a detection precision of a dark line position, the comparing being done by comparing each noise volume derived by the derivation unit with a threshold value that is predetermined for each width when the noise volume is derived, to thereby detect the detection precision of the dark line position.

14. A detection apparatus according to claim 1, wherein the optically transparent member has transparency to the light beam, wherein: distribution information indicating the light intensity distribution of the light beam which is totally reflected at the interface, and which is incident at a plurality of angles so as to be totally reflected at the interface, is acquired; a spatial frequency resolution is performed on the light intensity distribution indicated by the distribution information so that the light intensity distribution of each spatial frequency of the light beam is derived; and the light intensity distribution is compared with the threshold value predetermined for each spatial frequency so that a detection precision of a dark line position is detected.

15. A detection method comprising:
acquiring distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member;

performing a spatial frequency resolution on the light intensity distribution indicated by the distribution information acquired, to thereby derive the light intensity distribution of each spatial frequency of the light beam; and comparing the light intensity distribution derived, with a threshold value predetermined for each spatial frequency, to thereby detect a detection precision of a dark line position;

wherein:
the optically transparent member has a thin film layer formed at a part of the optically transparent member, and a sample is contacted on the thin film layer;

wherein acquiring the distribution information comprises acquiring a light intensity distribution of a light beam which is totally reflected at an interface between the optically transparent member and the thin film layer, the light beam being incident at a plurality of angles to the optically transparent film so as to be totally reflected at the interface between the optically transparent member and the thin film layer, and detecting a position of a dark line due to a total reflection attenuation is performed on the basis of the light intensity distribution indicated by the distribution information; and either stopping the detection of the position of the dark line by the dark line position or adding information indicating a decrease in the detection precision to a detection result by the dark line position detection, when the light intensity distribution of each spatial frequency of the light beam has a value larger than the threshold value predetermined for each spatial frequency, to thereby present the decrease in the detection precision, wherein the light beam is a P-polarized light beam.

16. A detection method comprising:
acquiring distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member;

performing a spatial frequency resolution on the light intensity distribution indicated by the distribution information acquired, to thereby derive the light intensity distribution of each spatial frequency of the light beam; and comparing the light intensity distribution derived, with a threshold value predetermined for each spatial frequency, to thereby detect a detection precision of a dark line position;

wherein:

the optically transparent member has a thin film layer formed at a part of the optically transparent member, and a sample is contacted on the thin film layer;

wherein acquiring the distribution information indicating a light intensity distribution of a light beam is performed at the interface between the optically transparent member and the thin film layer, the light beam being incident at a plurality of angles to the optically transparent film so as to be totally reflected at the interface between the optically transparent member and the thin film layer; and detecting a position of a dark line due to a total reflection attenuation is performed on the basis of the light intensity distribution indicated by the distribution information; further comprising:

storing in advance reference data indicating the light intensity distribution of the light beam in a state in which no total reflection attenuation occurs, wherein performing the spatial frequency resolution on a light intensity distribution which is determined as the difference between the light intensity distribution indicated by the distribution information acquired by the acquiring step and the light intensity distribution indicated by the reference data stored in advance, to thereby derive the light intensity distribution of each spatial frequency; further comprising:

updating the reference data, when detecting a decrease in the detection precision of the dark line position, with the distribution information acquired by the acquiring step at the time of the detecting the decrease in the detection precision of the dark line position.

17. A detection method comprising:

acquiring distribution information indicating a light intensity distribution of a light beam which is totally reflected at an interface of an optically transparent member, the light beam being incident at a plurality of angles to the optically transparent member, which has transparency to the light beam, such that the light beam is totally reflected at the interface of the optically transparent member;

performing a spatial frequency resolution on the light intensity distribution indicated by the distribution information acquired, to thereby derive the light intensity distribution of each spatial frequency of the light beam; and comparing the light intensity distribution derived, with a threshold value predetermined for each spatial frequency, to thereby detect a detection precision of a dark line position;

further comprising comparing the light intensity distribution derived with a threshold value predetermined for each spatial frequency, to thereby detect a foreign matter contained in the optically transparent member.

18. A detection apparatus according to claim 6, wherein the optically transparent member has transparency to the light beam, wherein: distribution information indicating the light intensity distribution of the light beam which is totally reflected at the interface, and which is incident at the plurality of angles so as to be totally reflected at the interface, is acquired; the spatial frequency resolution is performed on the light intensity distribution indicated by the distribution information so that the light intensity distribution of each spatial frequency of the light beam is derived; and the light intensity distribution is compared with the threshold value predetermined for each spatial frequency so that the detection precision of a dark line position is detected.

19. A detection apparatus according to claim 8, wherein the optically transparent member has transparency to the light beam, wherein: distribution information indicating the light intensity distribution of the light beam which is totally reflected at the interface, and which is incident at the plurality of angles so as to be totally reflected at the interface, is acquired; the spatial frequency resolution is performed on the light intensity distribution indicated by the distribution information so that the light intensity distribution of each spatial frequency of the light beam is derived; and the light intensity distribution is compared with the threshold value predetermined for each spatial frequency so that a detection precision of a dark line position is detected.

20. A detection apparatus according to claim 9, wherein the optically transparent member has transparency to the light beam, wherein: distribution information indicating the light intensity distribution of the light beam which is totally reflected at the interface, and which is incident at the plurality of angles so as to be totally reflected at the interface, is acquired; the spatial frequency resolution is performed on the light intensity distribution indicated by the distribution information so that the light intensity distribution of each spatial frequency of the light beam is derived; and the light intensity distribution is compared with the threshold value predetermined for each spatial frequency so that a detection precision of a dark line position is detected.

21. An optically transparent member having transparency to a light beam, wherein: distribution information indicating a light intensity distribution of the light beam which is totally reflected at an interface, and which is incident at a plurality of angles so as to be totally reflected at the interface, is acquired; a spatial frequency resolution is performed on the light intensity distribution indicated by the distribution information so that the light intensity distribution of each spatial frequency of the light beam is derived; and the light intensity distribution is compared with a threshold value predetermined for each spatial frequency so that a detection precision of a dark line position is detected used in the method of claim 13.

22. An optically transparent member having transparency to a light beam, wherein: distribution information indicating a light intensity distribution of the light beam which is totally reflected at an interface, and which is incident at a plurality of angles so as to be totally reflected at the interface, is acquired; a spatial frequency resolution is performed on the light intensity distribution indicated by the distribution information so that the light intensity distribution of each spatial frequency of the light beam is derived; and the light intensity distribution is compared with a threshold value predetermined for each spatial frequency so that a detection precision of a dark line position is detected used in the method of claim 15.

23. An optically transparent member having transparency to a light beam, wherein: distribution information indicating a light intensity distribution of the light beam which is totally reflected at an interface, and which is incident at a plurality of angles so as to be totally reflected at the interface, is acquired; a spatial frequency resolution is performed on the light intensity distribution indicated by the distribution information so that the light intensity distribution of each spatial frequency of the light beam is derived; and the light intensity distribution is compared with a threshold value predetermined for each spatial frequency so that a detection precision of a dark line position is detected used in the method of claim 16.

24. An optically transparent member having transparency to a light beam, wherein: distribution information indicating a light intensity distribution of the light beam which is totally reflected at an interface, and which is incident at a plurality of angles so as to be totally reflected at the interface, is acquired; a spatial frequency resolution is performed on the light intensity distribution indicated by the distribution information so that the light intensity distribution of each spatial frequency of the light beam is derived; and the light intensity distribution is compared with a threshold value predetermined for each spatial frequency so that a detection precision of a dark line position is detected used in the method of claim 17.

25. The detection apparatus according to claim 6, wherein:
the derivation unit derives the light intensity distribution of each spatial frequency of the light beam by performing a Fourier transformation on the light intensity distribution indicated by the distribution information.

26. The detection apparatus according to claim 6, wherein:
the sample is provided with a refractive index such that a dark line due to a total reflection attenuation is outside of the range of the light intensity distribution acquired by the acquisition unit, in the light intensity distribution of the P-polarized light beam totally reflected at the interface.

27. The detection apparatus according to claim 6, further comprising:
a storage unit that stores in advance reference data indicating the light intensity distribution of the light beam in a state in which no total reflection attenuation occurs,
wherein the derivation unit performs the spatial frequency resolution on a light intensity distribution which is determined as the difference between the light intensity distribution indicated by the distribution information acquired by the acquisition unit and the light intensity distribution indicated by the reference data stored in the storage unit, to thereby derive the light intensity distribution of each spatial frequency.

28. The detection apparatus according to claim 25, wherein:
the detection unit compares the light intensity distribution derived by the derivation unit, with a threshold value predetermined for each spatial frequency, to thereby detect a foreign matter contained in the optically transparent member.

29. The detection apparatus according to claim 6, wherein:
the detection unit derives the light intensity distribution of each spatial frequency by performing a Fourier transformation on the light intensity distribution derived by the derivation unit, to thereby detect a foreign matter contained in the optically transparent member.

30. The detection apparatus according to claim 8, wherein:
the derivation unit derives the light intensity distribution of each spatial frequency of the light beam by performing a Fourier transformation on the light intensity distribution indicated by the distribution information.

31. The detection apparatus according to claim 8, wherein:
the light beam is a P-polarized light beam; and
the sample is provided with a refractive index such that a dark line due to a total reflection attenuation is outside of the range of the light intensity distribution acquired by the acquisition unit, in the light intensity distribution of the P-polarized light beam totally reflected at the interface.

32. The detection apparatus according to claim 30, wherein:
the detection unit compares the light intensity distribution derived by the derivation unit, with a threshold value predetermined for each spatial frequency, to thereby detect a foreign matter contained in the optically transparent member.

33. The detection apparatus according to claim 8, wherein:
the detection unit derives the light intensity distribution of each spatial frequency by performing a Fourier transformation on the light intensity distribution derived by the derivation unit, to thereby detect a foreign matter contained in the optically transparent member.

34. The detection apparatus according to claim 9, wherein:
the derivation unit derives the light intensity distribution of each spatial frequency of the light beam by performing a Fourier transformation on the light intensity distribution indicated by the distribution information.

35. The detection apparatus according to claim 9, wherein:
the optically transparent member has a thin film layer formed at a part of the optically transparent member, and a sample is contacted on the thin film layer;
the acquisition unit acquires distribution information indicating a light intensity distribution of a light beam which is totally reflected at an interface between the optically transparent member and the thin film layer, the light beam being incident at a plurality of angles to the optically transparent member so as to be totally reflected at the interface between the optically transparent member and the thin film layer; and
the detection unit compares the light intensity distribution derived by the derivation unit, with a threshold value predetermined for each spatial frequency, to thereby detect a detection precision of a dark line position.

36. The detection apparatus according to claim 34, wherein:
the optically transparent member has a thin film layer formed at a part of the optically transparent member, and a sample is contacted on the thin film layer;
the acquisition unit acquires distribution information indicating a light intensity distribution of a light beam which is totally reflected at an interface between the optically transparent member and the thin film layer, the light beam being incident at a plurality of angles to the optically transparent member so as to be totally reflected at the interface between the optically transparent member and the thin film layer; and
the detection unit compares the light intensity distribution derived by the derivation unit, with a threshold value predetermined for each spatial frequency, to thereby detect a detection precision of a dark line position.

37. The detection apparatus according to claim 9, wherein:
the light beam is a P-polarized light beam; and
the sample is provided with a refractive index such that a dark line due to a total reflection attenuation is outside of the range of the light intensity distribution acquired by the acquisition unit, in the light intensity distribution of the P-polarized light beam totally reflected at the interface.

38. The detection apparatus according to claim 9, further comprising:

a storage unit that stores in advance reference data indicating the light intensity distribution of the light beam in a state in which no total reflection attenuation occurs, wherein the derivation unit performs the spatial frequency resolution on a light intensity distribution which is determined as the difference between the light intensity distribution indicated by the distribution information acquired by the acquisition unit and the light intensity distribution indicated by the reference data stored in the storage unit, to thereby derive the light intensity distribution of each spatial frequency.

39. The detection apparatus according to claim 9, wherein:

the detection unit compares the light intensity distribution derived by the derivation unit, with a threshold value predetermined for each spatial frequency, to thereby detect a foreign matter contained in the optically transparent member.

40. The detection apparatus according to claim 9, wherein:

the detection unit derives the light intensity distribution of each spatial frequency by performing a Fourier transformation on the light intensity distribution derived by the derivation unit, to thereby detect a foreign matter contained in the optically transparent member.

* * * * *